United States Patent
Schinazi et al.

(10) Patent No.: US 12,318,393 B2
(45) Date of Patent: Jun. 3, 2025

(54) MODULATORS OF ORPHAN NUCLEAR RECEPTORS FOR NASH AND OTHER METABOLIC DISORDERS

(71) Applicants: Emory University, Atlanta, GA (US); Hadasit Medical Research Services and Development Ltd., Jerusalem (IL)

(72) Inventors: Raymond F. Schinazi, Miami, FL (US); Bryan Cox, Atlanta, GA (US); Chofit Chai, Jerusalem (IL); Hilla Giladi, Jerusalem (IL); Eithan Galun, Jerusalem (IL); Franck Amblard, Atlanta, GA (US)

(*) Notice: Subject to any disclaimer, the term of this patent is extended or adjusted under 35 U.S.C. 154(b) by 1143 days.

(21) Appl. No.: 17/051,332

(22) PCT Filed: May 3, 2019

(86) PCT No.: PCT/US2019/030680
§ 371 (c)(1),
(2) Date: Oct. 28, 2020

(87) PCT Pub. No.: WO2019/213584
PCT Pub. Date: Nov. 7, 2019

(65) Prior Publication Data
US 2021/0052603 A1    Feb. 25, 2021

Related U.S. Application Data

(60) Provisional application No. 62/666,288, filed on May 3, 2018.

(51) Int. Cl.
| | |
|---|---|
| *A61K 31/5513* | (2006.01) |
| *A61K 31/015* | (2006.01) |
| *A61K 31/131* | (2006.01) |
| *A61K 31/475* | (2006.01) |
| *A61K 33/243* | (2019.01) |
| *A61K 45/06* | (2006.01) |
| *C07D 401/10* | (2006.01) |
| *C07D 401/12* | (2006.01) |
| *C07D 403/10* | (2006.01) |
| *C07D 413/10* | (2006.01) |

(52) U.S. Cl.
CPC ........ *A61K 31/5513* (2013.01); *A61K 31/015* (2013.01); *A61K 31/131* (2013.01); *A61K 31/475* (2013.01); *A61K 33/243* (2019.01); *A61K 45/06* (2013.01); *C07D 401/10* (2013.01); *C07D 401/12* (2013.01); *C07D 403/10* (2013.01); *C07D 413/10* (2013.01)

(58) Field of Classification Search
None
See application file for complete search history.

(56) References Cited

U.S. PATENT DOCUMENTS

| | | | |
|---|---|---|---|
| 8,202,989 B2 | 6/2012 | Meshram et al. | |
| 2004/0254159 A1* | 12/2004 | Hasvold | C07D 491/10 514/212.04 |
| 2007/0105835 A1* | 5/2007 | Kazantsev | A61K 31/365 514/450 |
| 2010/0006937 A1 | 3/2010 | Kasantsev et al. | |
| 2010/0069372 A1 | 3/2010 | Kasantsev et al. | |
| 2020/0247819 A1† | 8/2020 | He | |

FOREIGN PATENT DOCUMENTS

| | | | |
|---|---|---|---|
| CA | 3054324 A1 | 8/2018 | |
| WO | 2004076424 A1 | 9/2004 | |
| WO | 2007056388 A2 | 5/2007 | |
| WO | 2015138895 A1 | 9/2015 | |
| WO | WO-2018138254 A1 * | 8/2018 | H04L 25/4921 |

OTHER PUBLICATIONS

International Search Report and Written Opinion issued in counterpart PCT Application No. PCT/US2019/030680 dated Sep. 30, 2019 (eleven (11) pages).
PubChem-CID-22588425, Create Date: Dec. 5, 2007.
Indian Examination Report issued in Indian Patent Application No. 202047049933 dated May 5, 2022 (seven (7) pages).

* cited by examiner
† cited by third party

*Primary Examiner* — Jeffrey S Lundgren
*Assistant Examiner* — Michael J Schmitt
(74) *Attorney, Agent, or Firm* — David Bradin; Maynard Nexsen, PC

(57) ABSTRACT

Compounds, compositions and methods for modulating retinoic acid receptor-like orphan receptors (ROR) and associated diseases. Methods for treatment or prophylaxis of metabolic disorders, liver disorders or diseases, including NASH, immune disorders, central nervous system disorders, or cancer are disclosed.

14 Claims, 19 Drawing Sheets
Specification includes a Sequence Listing.

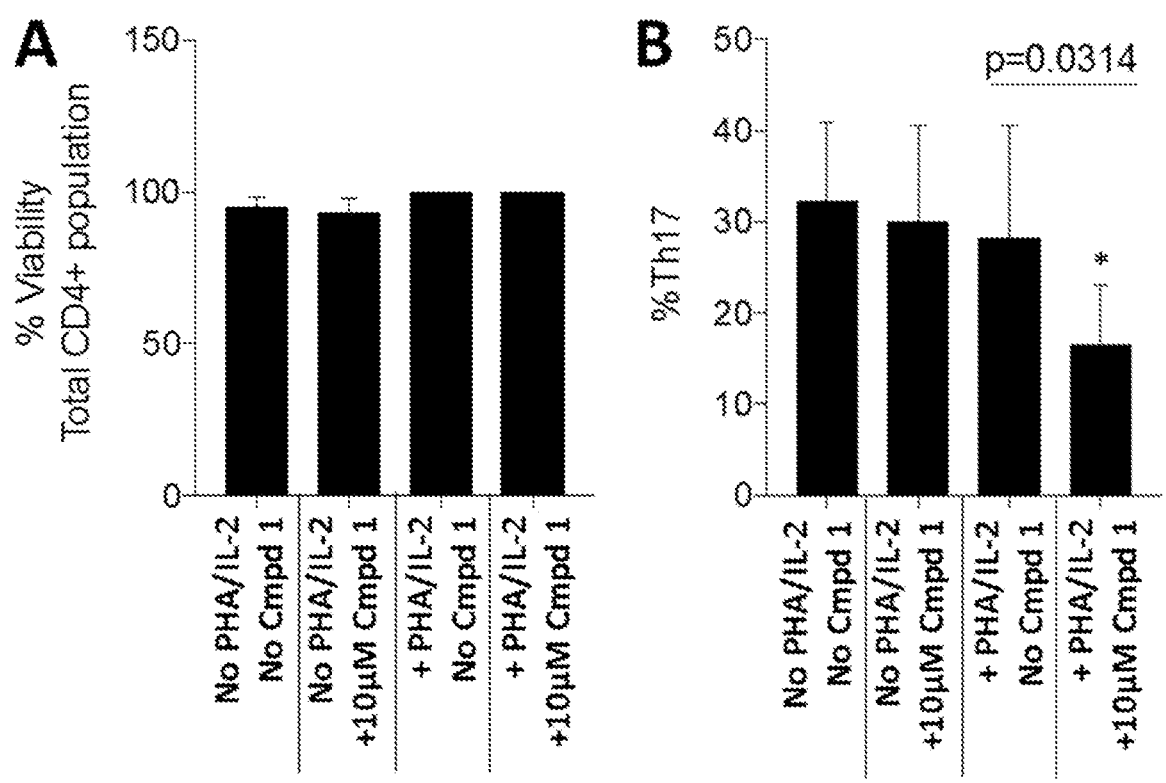
FIGURES 3A-B

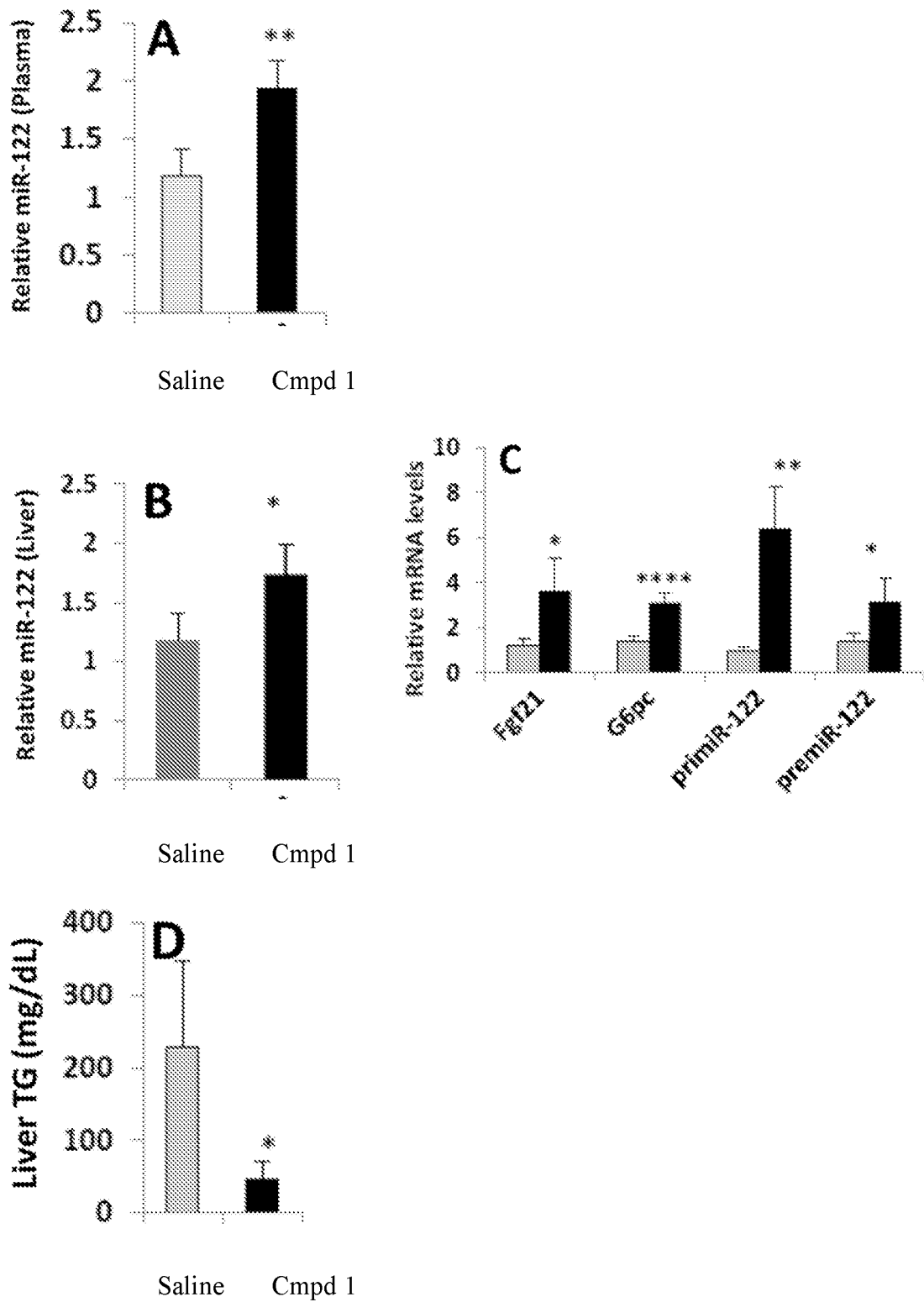
Figures 7A-D

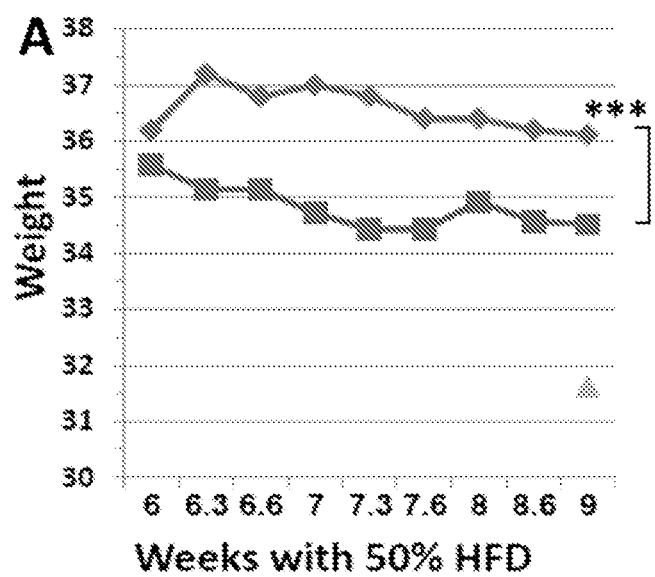
Figure 8A
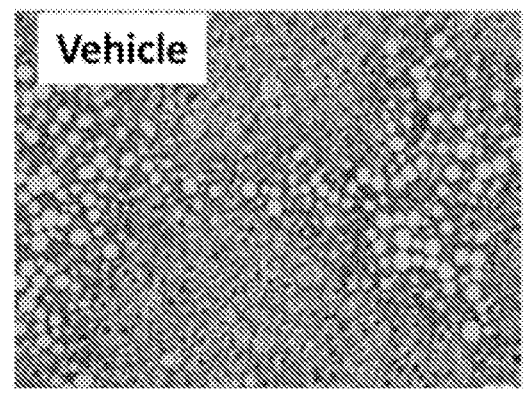
Compound 1
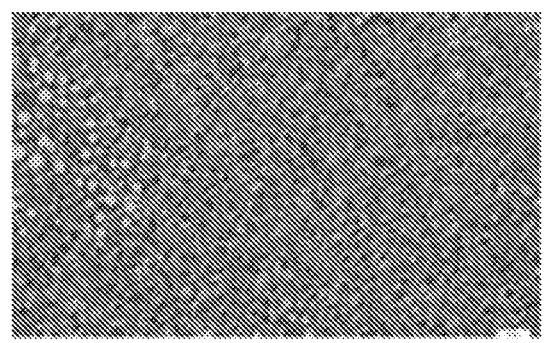
Figure 8B

Vehicle   Compound 1

Vehicle   Compound 1

Masson Trichrome
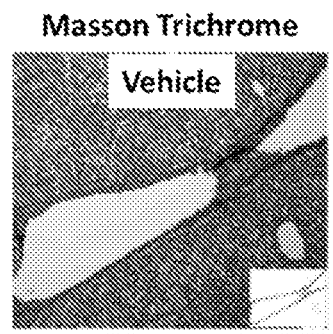
Compound 1
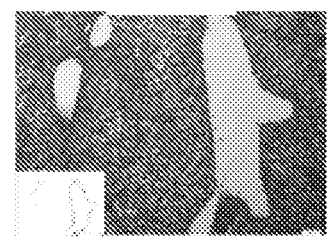
Figure 13A
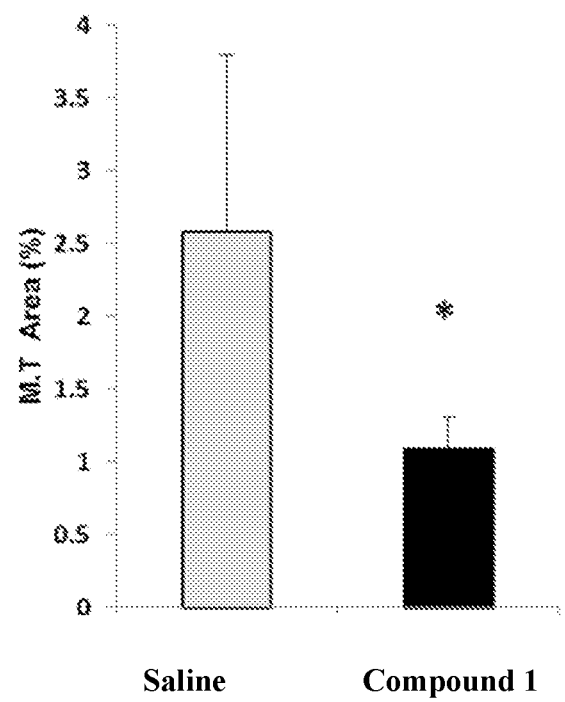
Figure 13B

MODULATORS OF ORPHAN NUCLEAR RECEPTORS FOR NASH AND OTHER METABOLIC DISORDERS

CROSS REFERENCE TO RELATED APPLICATIONS

This application is a 35 U.S.C. § 371 U.S. national phase entry of International Application No. PCT/US2019/030680 filed May 3, 2019, which is related to and claims priority under 35 U.S.C. § 119 (e) to U.S. Provisional Patent App. No. 62/666,288, filed on May 3, 2018; the entire disclosure of which is incorporated herein by reference.

FIELD OF THE INVENTION

The invention claims small molecule modulators of retinoic acid receptor-related orphan receptors (ROR) such as RORα, RORβ, or RORγ. The invention provides use of ROR modulators for cancer, liver disease (including NASH), dyslipidemia, autoimmune, and metabolic diseases.

BACKGROUND OF THE INVENTION

Type II nuclear receptor proteins are hormone-regulated transcription factors. Retinoic acid receptor-related orphan receptors (RORs) are type II nuclear receptors that exist in the nucleus of the cell sequestered to DNA. There are three major ROR isoforms RORα, RORβ, or RORγ with several variants identified based on sequentially similarity to the retinoic acid receptor. The ROR isoforms differ primarily in expression pattern. RORα is expressed in many tissues like liver, muscle, skin, adipose, and immune cells. RORβ is expressed specifically in the brain, retina, and pineal gland. RORγ shares a similar expression pattern as RORα, but with very high levels in the thymus. The major ROR isoforms possess a common structural motif composed of an N-terminal A/B domain containing an activation function 1 (AF-1), a C domain also called the DNA binding domain (DBD), a variable linker domain D, and a C-terminal E domain also called the ligand binding domain (LBD) that holds a ligand-dependent activation function 2 (AF-2). The DBD anchors RORs to specific DNA sequences, the ROR response element (RORE). Modulator binding to the LBD induces a conformational change that results in binding of transcriptional proteins to the AF-1 and AF-2. Some modulators decrease transcription at the RORE by inducing binding of co-repressor proteins to ROR. Alternatively, other modulators induce recruitment of co-activator proteins to ROR leading to enhanced transcription. Based on the genes regulated by RORs, these proteins play roles in circadian rhythm, metabolism, immune function, development, and brain function. [Kojetin, D J and Burris, T P. *Nature Reviews Drug Discovery* (2014) 13: 197-216]

ROR is involved in cancer development, progression, and severity [Qiu and Wang. Retinoic Acid Receptor-Related Orphan Receptor γt (RORγt) Agonists as Potential Small Molecule Therapeutics for Cancer Immunotherapy. *Journal of Medicinal Chemistry* (2018)]. Mice lacking RORγ rapidly develop metastatic T-cell lymphomas. Higher levels of RORγ correlate with improved outcomes in breast cancer. Several cancers show decreased RORα expression such as breast, colorectal, and prostate. Restoration of RORα expression inhibits cancer proliferation and metastasis. [Cook, D N, Kang H S, and Jetten, A M. *Nuclear Receptor Research* (2015) 2] Further, treatment with an ROR modulator induces apoptosis in cancer cells [Wand, Y, et. al. *PloS ONE* (2012) 7: e34921]. It follows that ROR modulators can be considered for cancer chemotherapy as monotherapy or in combination approaches.

CD4$^+$ T helper cells that secrete interleukin 17 (IL-17) are called Th17 cells. Th17 cells have a biological role in host defense against bacterial, fungal, parasitic, and viral infection. Dysregulation or Th17 cells is related to several immunological disorders. Th17 cells are involved in rheumatic diseases (psoriasis, arthritis, systemic sclerosis, and systemic lupus erythematosus), autoimmune disorders (multiple sclerosis, autoimmune myocarditis, diabetes, and autoimmune thyroiditis), asthma, allergic diseases, and other immune-mediated diseases like inflammatory bowel disease and periodontal disease. Th17 cells are also involved in cancer survival, proliferation, and survival. [Tesmer, L A, et. al. *Immunological Reviews* (2008) 223:87-113] It has been shown that ROR-targeting compounds modulate Th17 levels and IL-17 secretion, [Solt, L A, et. al. *Nature* (2011): 472: 491-494], and compounds of this class are therefore considered for treatment of Th17-related diseases and disorders.

ROR regulates energy homeostasis including lipid and glucose metabolism. Mice lacking ROR (staggerer) mice were shown to be protected against high fat diet (HFD)-induced metabolic syndrome as indicated by reduced weight gain, adiposity and hepatic steatosis, and improved insulin sensitivity and lipid metabolism/glucose metabolism. Conversely, adenovirus-mediated overexpression of ROR in liver also reduced triglyceride levels in mice fed a high fat diet. RORα cistrome data revealed that in liver, RORα was recruited to ROREs in several genes important in glucose homeostasis and lipid metabolism indicating that RORα positively regulates the transcription of these metabolic genes by binding ROREs in their regulatory region. A role for RORα in the regulation of insulin sensitivity is supported by a study showing an association between a single nucleotide polymorphism in RORα (rs7164773) and an increased risk for type 2 diabetes in the Mexico Mestizo population. Mice lacking the RORγ isoform had improved insulin sensitivity compared to control. A role for RORγ in the regulation of insulin resistance is supported by studies showing that the level of RORγ expression positively correlates with adiposity and insulin resistance in human obese patients. [Cook, D N, Kang H S, and Jetten, A M. *Nuclear Receptor Research* (2015) 2]

It would be advantageous to provide ROR modulators, and methods of treatment, particularly to treat metabolic diseases, diabetes, dyslipidemia, and liver diseases. The present invention provides such agents, compositions and methods.

SUMMARY OF THE INVENTION

In one embodiment, compounds, methods and compositions for treating conditions associated with ROR nuclear receptors in particular cancer, Th17-associated disease, or liver disease, are disclosed.

In one embodiment, methods are provided for modulating the bioactivity of ROR. The methods involve contacting the ROR with an effective amount of a compound of formula (A) as shown below, wherein the compound is an agonist or an activator, or is a repressor, inverse agonist, or antagonist, of a receptor comprising any sequence variant of any isoform of the ROR subfamily, including RORα, RORβ, or RORγ.

The invention provides novel compounds for performing the methods of the invention. The present invention provides stereoisomers and polymorphisms for conducting the methods of the invention. The invention provides salt or prodrug formulations for performing the methods of the invention.

In various embodiments, pharmaceutical compositions and formulations with an effective compound of formula (A) are provided to treat conditions associated with ROR nuclear receptors.

The invention provides pharmaceutical combinations comprising a compound of the invention and one or more other medicaments.

The present invention will be better understood with reference to the following Detailed Description.

BRIEF DESCRIPTION OF THE DRAWINGS

FIGS. 3A-B are charts showing how Compound 1 modulates Th17 populations in human peripheral mononuclear cells (PBMCs). FIG. 3A shows how the viability of CD4+ T cells was determined by LIVE/DEAD fixable aqua dead cell staining, shown as % viability over the total CD4+Th17 cell population. FIG. 3B shows the total percent composition of CD4+ Th17 cells (in terms of % Th17 cells) as determined by gating on CD3+/CD4+/CD45RA−/CXCR3−/CCR4+ CXCR5−/CCR6+ cells. These results show that Compound 1 decreases the CD4+ Th17 population selectively under stimulating conditions.

FIG. 4A shows plasma levels, and FIG. 4B shows liver levels, of miR-122 levels measured over 7 days. FIG. 4C shows mRNA levels of miR-122 and RORα target genes (Aldoa and Gpase6, respectively), and miR-122 precursor were measured over 7 days. The data show that secreted miR-122 enters periphery tissues. FIGS. 4D and 4E show miR-122 levels in skeletal muscle (4D) and white adipose tissues ("WAT") (4E) were measured over 7 days. The data show that miR-18 and miR-126 were not affected following treatment with Compound 1. Data are presented as error bars=SD. *P<0.05, P<0.01, *P<0.001 compare to saline. White bars are control (saline), red bars are results from Day 1, pink bars are results from Day 3, and purple bars are results from Day 7.

FIG. 5A shows the change in body weight (grams) before (blue) and after (red) 3 weeks of treatment. FIG. 5B shows the qRT-PCR analysis of relative miR-122 levels in plasma at the final time point. FIG. 5C is a chart showing the colorimetric quantification of β-hydroxybutyrate plasma levels (in nM) 3 weeks after treatment.

FIG. 5D is a photograph of representative lipid accumulation visualized by H&E staining of liver sections. Antagomirs are used to silence endogenous microRNA. An antagomir is a small synthetic RNA with certain modifications that are perfectly complementary to a specific miRNA, and block it from binding to its mRNA targets. In the top two photographs, an antagomir was used as a negative control (mimiccon), known as antagomir-con (RiboBio Company, China), both with Compound 1 (right side), and without Compound 1 (left side). In the bottom two photographs, an antagomir was used that is substantially complementary to miR-122 (antagomiR-122), both with Compound 1 (right side), and without Compound 1 (left side). The photographs show reduced lipid droplets accumulation when Compound 1 is administered.

FIGS. 6A-6B show the qRT-PCR analysis of miR-122 levels in plasma (6A), and in the livers (6B) after 4 weeks treatment with saline (as a control) and Compound 1. MicroRNA-18 was used as a negative control and its plasma and liver levels were not affected following treatment with Compound 1. The effect seen on this microRNA in FIG. 6A is not significant compared to the significant effect seen on miR-122. FIG. 6C is a chart showing a colorimetric quantification of triglycerides (TG) in liver (mg/g) following administration of saline (as control) and Compound 1. Data are presented as error bars=S.D. *P<0.05.

FIGS. 7A and B show the results of qRT-PCR analysis of miR-122 extracted from plasma and liver, respectively, in mice treated with Compound 1 or saline. FIG. 7C shows the qRT-PCR analysis of Fgf21 and G6pc, as well as RORα target genes, pri- and pre-miR-122 mRNA, extracted from mice livers. FIG. 7D is a chart showing the quantification of liver triglyceride (TG) levels (mg/dL) for mice administered saline or Compound 1.

FIG. 8A shows the weight of C57BL/6 mice fed for 6 weeks with a high fat diet (HFD), and were injected with 15 mg/kg Compound 1 (squares) or control (saline+DMSO) (diamonds) 3 times a week for 3 weeks (n=6). FIG. 8B is a microphotograph of liver, with H&E (hematein/eosin Y) staining, of a mouse treated with Compound 1, or control.

FIG. 11C is a chart that shows ALT and AST plasma levels measured at the end of the experiment. FIG. 11D is a chart showing qRT-PCR analysis of mRNA of genes involved in fibrosis and RORα target gene (Fgf21) extracted from mice livers. microRNA levels in the plasma were normalized to spiked *C. elegans* miR-39; microRNA levels in the tissues were normalized to RNU6. mRNA levels were normalized to HPRT. Data are presented as error bars=SD. *P<0.05, P<0.01. *P<0.001, ****P<0.0001.

DETAILED DESCRIPTION

Figure 1:
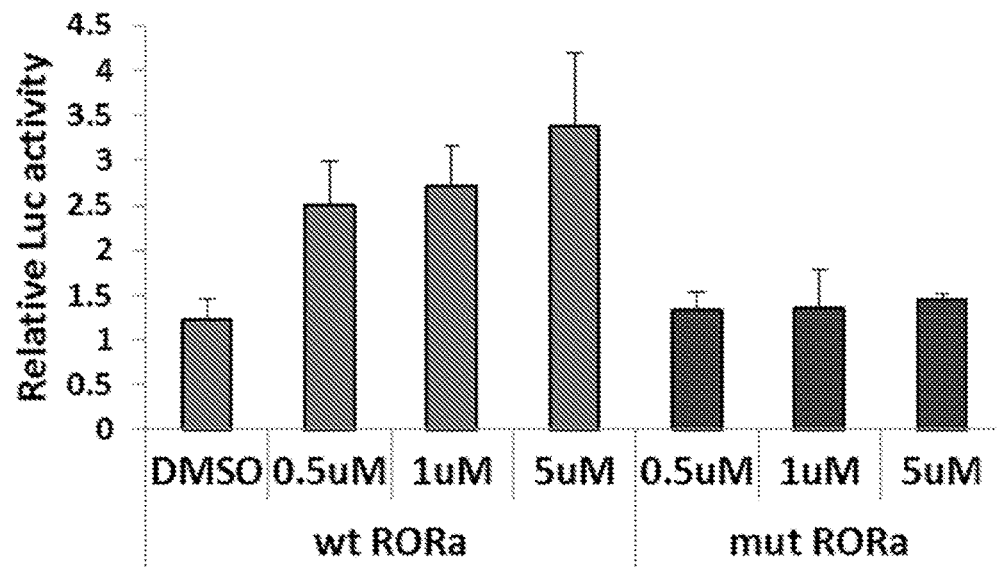
FIG. 1 is a chart showing how Compound 1 induces expression of RORα-regulated luciferase with a WT RORE but has no activity when the RORE is mutated. Data are presented in terms of relative lucerifase activity versus concentration, with error bars=SD. *P<0.05 compared to DMSO.

The compounds described herein of Formula (A) modulate expression of ROR target genes in hepatocyte cells, particularly those related to metabolism and liver disease. Therefore, the compounds can be used to treat or prevent liver disease such as, but not limited to, cirrhosis, liver fibrosis, non-alcoholic fatty liver disease (NAFLD), non-alcoholic steatohepatitis (NASH), alcoholic steatohepatitis (ASH), hepatic ischemia reperfusion injury, primary biliary cirrhosis (PBC), and hepatitis, including both viral and alcoholic hepatitis. The compounds can be used to treat or prevent metabolic disease such as, but not limited to, dyslipidemia, obesity, insulin resistance, or diabetes mellitus.

The compounds described herein modulate the population of Th17 cells in cultures of human peripheral mononuclear cells. Therefore, the compounds can be used to treat or prevent Th17-related conditions or diseases such as, but not limited to, rheumatic diseases (psoriasis, arthritis, systemic sclerosis, and systemic lupus erythematosus), auto-immune disorders (multiple sclerosis, autoimmune myocarditis, diabetes, and autoimmune thyroiditis), asthma, allergic diseases, and other immune-mediated diseases like inflammatory bowel disease and periodontal disease The compounds described herein show inhibitory activity against lymphoblastic leukemia and hepatocellular carcinoma cell lines, CCRF-CEM and Huh-7, respectively. Therefore, the compounds can be used to treat or prevent cancer and related diseases or disorders. More specifically, cancer can comprise prostate cancer, colon cancer, breast cancer, lung cancer, etc.

Pharmaceutical formulations including one or more compounds described herein, in combination with a pharmaceutically acceptable carrier or excipient, are also disclosed. In one embodiment, the formulations include at least one compound described herein and at least one further therapeutic agent.

The present invention will be better understood with reference to the following definitions:

I. Definitions

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

The term "modulator" includes antagonists, allosteric inhibitors, agonists, and partial agonists. Certain modulators can shut down ROR expression (antagonists and allosteric inhibitors directly, and partial agonists in a dose-dependent manner), and others (agonists and partial agonists, the latter in a dose-dependent manner) can increase ROR expression.

As used herein, the term "enantiomerically pure" refers to a compound composition that comprises at least approximately 95%, and, preferably, approximately 97%, 98%, 99% or 100% of a single enantiomer of that compound.

As used herein, the term "substantially free of" or "substantially in the absence of" refers to a compound composition that includes at least 85 to 90% by weight, preferably 95% to 98% by weight, and, even more preferably, 99% to 100% by weight, of the designated enantiomer of that compound. In a preferred embodiment, the compounds described herein are substantially free of enantiomers.

Similarly, the term "isolated" refers to a compound composition that includes at least 85 to 90% by weight, preferably 95% to 98% by weight and, even more preferably, 99% to 100% by weight, of the compound, the remainder comprising other chemical species or enantiomers.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included are $CF_3$ and $CH_2CF_3$. Where the alkyl moiety is substituted at both ends, it is an "alkylene" moiety, such as a methylene moiety, and such are intended to be encompassed herein.

In the text, whenever the term C(alkyl range) is used, the term independently includes each member of that class as if specifically and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

As used herein, a "bridged alkyl" refers to a bicyclo- or tricycloalkane, for example, a 2:1:1 bicyclohexane.

As used herein, a "spiro alkyl" refers to two rings that are attached at a single (quaternary) carbon atom.

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moeities. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methyl-butyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "fatty alcohol" as used herein refers to straight-chain primary alcohols with between 4 and 26 carbons in the chain, preferably between 8 and 26 carbons in the chain, and most preferably, between 10 and 22 carbons in the chain. The precise chain length varies with the source. Representative fatty alcohols include lauryl, stearyl, and oleyl alcohols. They are colorless oily liquids (for smaller carbon numbers) or waxy solids, although impure samples may appear yellow. Fatty alcohols usually have an even number of carbon atoms and a single alcohol group (—OH) attached to the terminal carbon. Some are unsaturated and some are branched. They are widely used in industry. As with fatty acids, they are often referred to generically by the number of carbon atoms in the molecule, such as "a $C_{12}$ alcohol", that is an alcohol having 12 carbons, for example dodecanol.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydoxyheteroaralkyl, haloalkoxyalkyl, aryl, aralkyl, aryloxy, arylkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from the group consisting of straight, branched, or cyclic alkyl or lower alkyl, alkoxyalkyl, including, but not limited to methoxymethyl, aralkyl, including, but not limited to, benzyl, aryloxyalkyl, such as phenoxymethyl, aryl, including, but not limited to, phenyl, optionally substituted with halogen (F, Cl, Br, or I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic," "heterocyclyl," and cycloheteroalkyl refer to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituents selected from the group consisting of halogen, haloalkyl, alkyl, alkoxy, hydroxy, carboxyl derivatives, amido, amino, alkylamino, and dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluene sulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and, preferably, humans. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human being. Veterinary applications, in certain indications, however, are clearly contemplated by the present invention (such as for use in treating chimpanzees).

The term "peptide" refers to a natural or synthetic compound containing two to one hundred amino acids linked by the carboxyl group of one amino acid to the amino group of another.

The term "pharmaceutically acceptable salt or prodrug" is used throughout the specification to describe any pharmaceutically acceptable form (such as an ester) compound which, upon administration to a patient, provides the compound. Pharmaceutically-acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art.

Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

Non-limiting examples of phosphate/phosponate prodrugs are described in the following references: Ho, D. H. W. (1973) "Distribution of Kinase and deaminase of 1-beta-D-arabinofuranosylcytosine in tissues of man and muse." Cancer Res. 33, 2816-2820; Holy, A. (1993) Isopolar phosphorous-modified nucleotide analogues," In: De Clercq (Ed.), Advances in Antiviral Drug Design, Vol. I, JAI Press, pp. 179-231; Hong, C. I., Nechaev, A., and West, C. R. (1979a) "Synthesis and antitumor activity of 1-beta-D-arabino-furanosylcytosine conjugates of cortisol and cortisone." Bicohem. Biophys. Rs. Commun. 88, 1223-1229; Hong, C. I., Nechaev, A., Kirisits, A. J. Buchheit, D. J. and West, C. R. (1980) "Nucleoside conjugates as potential antitumor agents. 3. Synthesis and antitumor activity of 1-(beta-D-arabinofuranosyl)cytosine conjugates of corticosteroids and selected lipophilic alcohols." J. Med. Chem. 28, 171-177; Hosteller, K. Y., Stuhmiller, L. M., Lenting, H. B. M. van den Bosch, H. and Richman J. Biol. Chem. 265, 6112-6117; Hosteller, K. Y., Carson, D. A. and Richman, D. D. (1991); "Phosphatidylazidothymidine: mechanism of antiretroviral action in CEM cells." J. Biol Chem. 266, 11714-11717; Hosteller, K. Y., Korba, B. Sridhar, C., Gardener, M. (1994a) "Antiviral activity of phosphatidyl-dideoxycytidine in hepatitis B-infected cells and enhanced hepatic uptake in mice." Antiviral Res. 24, 59-67; Hosteller, K. Y., Richman, D. D., Sridhar. C. N. Felgner, P. L. Felgner, J., Ricci, J., Gardener, M. F. Selleseth, D. W. and Ellis, M. N. (1994b) "Phosphatidylazidothymidine and phosphatidyl-ddC: Assessment of uptake in mouse lymphoid tissues and antiviral activities in human immunodeficiency virus-infected cells and in rauscher leukemia virus-infected mice." Antimicrobial Agents Chemother. 38, 2792-2797; Hunston, R. N., Jones, A. A. McGuigan, C., Walker, R. T., Balzarini, J., and DeClercq, E. (1984) "Synthesis and biological properties of some cyclic phosphotriesters derived from 2'-deoxy-5-flourouridine." J. Med. Chem. 27, 440-444; Ji, Y. H., Moog, C., Schmitt, G., Bischoff, P. and Luu, B. (1990); "Monophosphoric acid esters of 7-.beta.-hydroxycholesterol and of pyrimidine nucleoside as potential antitumor agents: synthesis and preliminary evaluation of antitumor activity." J. Med. Chem. 33 2264-2270; Jones, A. S., McGuigan, C., Walker, R. T., Balzarini, J. and DeClercq, E. (1984) "Synthesis, properties, and biological activity of some nucleoside cyclic phosphoramidates." J. Chem. Soc. Perkin Trans. I, 1471-1474; Juodka, B. A. and Smrt, J. (1974) "Synthesis of diribonucleoside phosph (P.fwdarw.N) amino acid derivatives." Coll. Czech. Chem. Comm. 39, 363-968; Kataoka, S., Imai, J., Yamaji, N., Kato, M., Saito, M., Kawada, T. and Imai, S. (1989) "Alkylated cAMP derivatives; selective synthesis and biological activities." Nucleic Acids Res. Sym. Ser. 21, 1-2; Kataoka, S., Uchida, "(cAMP) benzyl and methyl triesters." Heterocycles 32, 1351-1356; Kinchington, D., Harvey, J. J., O'Connor, T. J., Jones, B. C. N. M., Devine, K. G., Taylor-Robinson D., Jeffries, D. J. and McGuigan, C. (1992) "Comparison of antiviral effects of zidovudine phosphoramidate an dphosphorodiamidate derivates against HIV and ULV in vitro." Antiviral Chem. Chemother. 3, 107-112; Kodama, K., Morozumi, M., Saithoh, K. I., Kuninaka, H., Yosino, H. and Saneyoshi, M. (1989) "Antitumor activity and pharmacology of 1-.beta.-D-arabinofuranosylcytosine-5'-stearylphosphate; an orally active derivative of 1-.beta.-D-arabinofuranosylcytosine." Jpn. J. Cancer Res. 80, 679-685; Korty, M. and Engels, J. (1979) "The effects of adenosine- and guanosine 3',5' phosphoric and acid benzyl esters on guinea-pig ventricular myocardium." Naunyn-Schmiedeberg's Arch. Pharmacol. 310, 103-111; Kumar, A., Goe, P. L., Jones, A. S. Walker, R. T. Balzarini, J. and DeClercq, E. (1990) "Synthesis and biological evaluation of some cyclic phosphoramidate nucleoside derivatives." J. Med. Chem, 33, 2368-2375; LeBec, C., and Huynh-Dinh, T. (1991) "Synthesis of lipophilic phosphate triester derivatives of 5-fluorouridine an arabinocytidine as anticancer prodrugs." Tetrahedron Lett. 32, 6553-6556; Lichtenstein, J., Barner, H. D. and Cohen, S. S. (1960) "The metabolism of exogenously supplied nucleotides by Escherichia coli.," J. Biol. Chem. 235, 457-465; Lucthy, J., Von Daeniken, A., Friederich, J. Manthey, B., Zweifel, J., Schlatter, C. and Benn, M. H. (1981) "Synthesis and toxicological properties of three naturally occurring cyanoepithioalkanes". Mitt. Geg. Lebensmittelunters. Hyg. 72, 131-133 (Chem. Abstr. 95, 127093); McGigan, C. Tollerfield, S. M. and Riley, P.a. (1989) "Synthesis and biological evaluation of some phosphate triester derivatives of the antiviral drug Ara." Nucleic Acids Res. 17, 6065-6075; McGuigan, C., Devine, K. G., O'Connor, T. J., Galpin, S. A., Jeffries, D. J. and Kinchington, D. (1990a) "Synthesis and evaluation of some novel phosphoramidate derivatives of 3'-azido-3'-deoxythymidine (AZT) as anti-HIV compounds." Antiviral Chem. Chemother. 1 107-113; McGuigan, C., O'Connor, T. J., Nicholls, S. R. Nickson, C. and Kinchington, D. (1990b) "Synthesis and anti-HIV activity of some novel substituted dialkyl phosphate derivatives of AZT and ddCyd." Antiviral Chem. Chemother. 1, 355-360; McGuigan, C., Nicholls, S. R., O'Connor, T. J., and Kinchington, D. (1990c) "Synthesis of some novel dialkyl phosphate derivative of 3'-modified nucleosides as potential anti-AIDS drugs." Antiviral Chem. Chemother. 1, 25-33; McGuigan, C., Devin, K. G., O'Connor, T. J., and Kinchington, D. (1991) "Synthesis and anti-HIV activity of some haloalkyl phosphoramidate derivatives of 3'-azido-3'-deoxythylmidine (AZT); potent activity of the trichloroethyl methoxyalaninyl compound." Antiviral Res. 15, 255-263; McGuigan, C., Pathirana, R. N., Balzarini, J. and DeClercq, E. (1993b) "Intracellular delivery of bioactive AZT nucleotides by aryl phosphate derivatives of AZT." J. Med. Chem. 36, 1048-1052.

II. Active Compounds

In one embodiment, the compounds have the following formula:

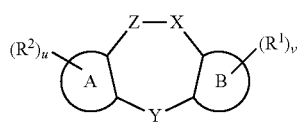

Formula A or a pharmaceutically acceptable salt or prodrug thereof.

In this formula:

one of X and Z is selected from the group consisting of —NH—, —N(NH$_2$)—, —NH(OH)—, —N(C$_{1-10}$ alkyl)-, —N(C$_{3-10}$ cycloalkyl)-, —N(C$_{2-10}$alkenyl)-, —N(C$_{2-10}$alkynyl)-, —N(aryl)-, or —N(heteroaryl)-, —O—, —CH$_2$—, —CH(C$_{1-10}$alkyl)-, C(C$_{1-10}$alkyl)$_2$-, —CH(C$_{3-10}$ cycloalkyl)-, —CH(C$_{2-10}$ alkenyl, —CH(C$_{2-10}$alkynyl)-, —CH(aryl)-, —CH(heteroaryl)-, —CF$_2$—, —CCl$_2$—, —CH(CF$_3$)—, —CH(OH)—, —CH(O—C$_{1-10}$ Alkyl)-, —CH(NH$_2$)—, —CH(NH—C$_{1-10}$ Alkyl)-, and —CH(C(O)NH$_2$)—, and the other one of X and Z is selected from the group consisting of —C(O)—, —SO$_2$—, —N(C(O)—, —CH$_2$—, —CH(C$_{1-10}$alkyl)-, C(C$_{1-10}$alkyl)$_2$-, —CH(C$_{3-10}$ cycloalkyl)-, —CH(C$_{2-10}$alkenyl, —CH(C$_{2-10}$ alkynyl)-, —CH(aryl)-, —CH(heteroaryl)-, —CF$_2$—, —CCl$_2$—, —CH(CF$_3$)—, —CH(OH)—, —CH(OAlkyl)-, —CH(NH$_2$)—, —CH(NHC$_{1-10}$ Alkyl)-, and —CH(C(O)NH$_2$)—, Y is selected from the group consisting of —NH, —N(NH$_2$)—, —NH(OH)—, N(C$_{1-10}$ alkyl)-, —N(C$_{3-10}$ cycloalkyl)-, —N(C$_{2-10}$alkenyl)-, —N(C$_{2-10}$alkynyl)-, —N(aryl)-, or —N(heteroaryl)-, —O—, —CH$_2$—, —CH(C$_{1-10}$alkyl)-, —CH(C$_{3-10}$ cycloalkyl)-, —CH(C$_{2-10}$alkenyl, —CH(C$_{2-10}$alkynyl)-, —CH(aryl)-, —CH(heteroaryl)-, —C(C$_{1-10}$ alkyl)$_2$-, —CF$_2$—, —CCl$_2$—, —CH(CF$_3$)—, —CH(OH)—, —CH(O—C$_{1-10}$ Alkyl)-, —C(O)—, —SO$_2$—, —N(C(O)—C$_{1-10}$ Alkyl)-, —N(C(O)O—C$_{1-10}$ Alkyl)-, —CH(NH$_2$)—, —CH(NH—C$_{1-10}$ Alkyl)-, and —CH(C(O)NH$_2$)—, A and B are, independently, phenyl, a five-membered heteroaromatic ring containing one, two or three nitrogen, oxygen, or sulfur atoms, or a six-membered heteroaromatic ring containing one, two or three nitrogen atoms;

u and v are independently 0, 1, 2, 3 or 4; with the proviso that at least one of u and v is 1, 2, 3, or 4;

each $R^1$ and $R^2$ are independently $R^3$, OH, OR$^3$, SR$^3$, S(O)R$^3$, SO$_2$R$^3$, C(O)R$^3$, C(O)OR$^3$, OC(O)R$^3$, OC(O)OR$^3$, NH$_2$, NHR$^3$, NHC(O)R$^3$, NR$^3$C(O)R$^3$, NHS(O)$_2$R$^3$, NR$^3$S(O)$_2$R$^3$, NHC(O)OR$^3$, NR$^3$C(O)OR$^3$, NHC(O)NH$_2$, NHC(O)NHR$^3$, NHC(O)N(R$^3$)$_2$, NR$^3$C(O)N(R$^3$)$_2$, C(O)NH$_2$, C(O)NHR$^3$, C(O)N(R$^3$)$_2$, C(O)NHOH, C(O)NHOR$^3$, C(O)NHSO$_2$R$^3$, C(O)NR$^3$SO$_2$R$^3$, SO$_2$NH$_2$, SO$_2$NHR$^3$, SO$_2$N(R$^3$)$_2$, COOH, C(O)H, C(N)NH$_2$, C(N)NHR$^3$, C(N)N(R$^3$)$_2$, C(N)OH, C(N)OCH$_3$, CN, N$^3$, NO$_2$, CF$_3$, CF$_2$CF$_3$, OCF$_3$, OCF$_2$CF$_3$, halo (F, Cl, Br, or I), —CH$_2$-phosphonate, —CH$_2$O-phosphate, CH$_2$P(O)(OH)$_2$, CH$_2$P(O)(OR$^3$)$_2$, CH$_2$P(O)(OR$^3$)(NR$^3$), CH$_2$P(O)(NR$^3$)$_2$, CH$_2$P(O)(OH) (OC$_{1-10}$ alkyl-O—C$_{1-20}$ alkyl), or CH$_2$-cycloSal monophosphate prodrug, wherein the term phosphate includes monophosphate, diphosphate, triphosphate, and stabilized phosphate prodrugs, and the term phosphonate includes the same prodrugs that are present in the phosphate prodrugs, and when $R^1$ and $R^2$ are on adjacent carbon, they can come together to form an saturated or unsaturated alkyl, an aromatic or a heteroaromatic ring;

each $R^3$ is, independently, aryl, heteroaryl, C$_{3-10}$ cycloalkyl, C$_{3-10}$ cycloalkenyl, heterocycloalkyl, heterocycloalkenyl, C$_{1-10}$ alkyl, C$_{2-10}$ alkenyl or C$_{2-10}$ alkynyl, each of which is unsubstituted or independently substituted with one or more substituents selected from the group consisting of R$^4$, OH, OR$^4$, SR$^4$, S(O)R$^4$, SO$_2$R$^4$, C(O)R$^4$, C(O)OR$^4$, OC(O)R$^4$, OC(O)OR$^4$, NH$_2$, NHR$^4$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, COOH, C(O)H, C(N)NH$_2$, C(N)NHR$^4$, C(N)N(R$^4$)$_2$, C(N)OH, C(N)OCH$^4$, CN, N$^3$, NO$_2$, CF$_3$, CF$_2$CF$_3$, OCF$_3$, OCF$_2$CF$_3$, halo (F, Cl, Br, or I), P(O)(OH)$_2$, P(O)(OR$^4$)$_2$, P(O)(OR$^4$)(NR$^4$), P(O)(NR$^4$)$_2$, P(O)(OH)(OC$_{1-10}$ alkyl-O—C$_{1-20}$ alkyl), cycloSal monophosphate prodrugs, CH$_2$P(O)(OH)$_2$, CH$_2$P(O)(OR$^4$)$_2$, CH$_2$P(O)(OR$^4$)(NR$^4$), CH$_2$P(O)(NR$^4$)$_2$, CH$_2$P(O)(OH)(OC$_{1-10}$ alkyl-O—C$_{1-20}$ alkyl), and CH$_2$-cycloSal monophosphate prodrugs, each R$^4$ are independently selected from aryl, heteroaryl, arylalkyl, alkylaryl, C$_{3-10}$ cycloalkyl, C$_{3-10}$ cycloalkenyl, heterocycloalkyl, heterocycloalkenyl, C$_{1-10}$ alkyl, C$_{2-10}$ alkenyl, and C$_{2-10}$ alkynyl, each of which is unsubstituted or independently substituted with one or more substituents selected from the group consisting of R$^5$, OH, OR$^5$, SR$^5$, S(O)R$^5$, SO$_2$R$^5$, C(O)R$^5$, C(O)OR$^5$, OC(O)R$^5$, OC(O)OR$^5$, NH$_2$, NHR$^5$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, COOH, C(O)H, C(N)NH$_2$, C(N)NHR$^5$, C(N)N(R$^5$)$_2$, C(N)OH, C(N)OCH$_3$, CN, N$^3$, NO$_2$, CF$_3$, CF$_2$CF$_3$, OCF$_3$, OCF$_2$CF$_3$, halo (F, Cl, Br, or I), P(O)(OH)$_2$, P(O)(OR$^4$)$_2$, P(O)(OR$^4$)(NR$^4$), P(O)(NR$^4$)$_2$, P(O)(OH)(OC$_{1-10}$ alkyl-O—C$_{1-20}$ alkyl), and cycloSal monophosphate prodrugs, each R$^5$ are independently aryl, heteroaryl, C$_{3-10}$ cycloalkyl, C$_{3-10}$ cycloalkenyl, heterocycloalkyl, heterocycloalkenyl, C$_{1-10}$ alkyl, C$_{2-10}$ alkenyl or C$_{2-10}$ alkynyl, each of which is unsubstituted or independently substituted with one or more substituents selected from the group consisting of R$^6$, OH, OR$^6$, SR$^6$, S(O)R$^6$, SO$_2$R$^6$, C(O)R$^6$, C(O)OR$^6$, OC(O)R$^6$, OC(O)OR$^6$, NH$_2$, NHR$^6$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, COOH, C(O)H, C(N)NH$_2$, C(N)NHR$^6$, C(N)N(R$^6$)$_2$, C(N)OH, C(N)OCH$_3$, CN, N$^3$, NO$_2$, CF$_3$, CF$_2$CF$_3$, OCF$_3$, OCF$_2$CF$_3$, F, Cl, Br, I, P(O)(OH)$_2$, P(O)(OR$^4$)$_2$, P(O)(OR$^4$)(NR$^4$), P(O)(NR$^4$)$_2$, P(O)(OH)(OC$_{1-10}$ alkyl-O—C$_{1-20}$ alkyl), and cycloSal monophosphate prodrugs, each R$^6$ are independently aryl, heteroaryl, C$_{3-10}$ cycloalkyl, C$_{3-10}$ cycloalkenyl, heterocycloalkyl, heterocycloalkenyl, C$_{1-10}$ alkyl, C$_{2-10}$ alkenyl or C$_{2-10}$ alkynyl, each of which is unsubstituted or independently substituted with one or more substituents selected from the group consisting of C$_{1-10}$ alkyl, C$_{2-10}$ alkenyl, C$_{2-10}$ alkynyl, OH, NH$_2$, C(O)NH$_2$, C(O)NHOH, SO$_2$NH$_2$, COOH, C(O)H, C(N)NH$_2$, C(N)OH, C(N)OCH$_3$, CN, N$^3$, NO$_2$, CF$_3$, CF$_2$CF$_3$, OCF$_3$, OCF$_2$CF$_3$, halo (F, Cl, Br, or I), P(O)(OH)$_2$, P(O)(OR$^4$)$_2$, P(O)(OR$^4$)(NR$^4$), P(O)(NR$^4$)$_2$, P(O)(OH)(OC$_{1-10}$ alkyl-O—C$_{1-20}$ alkyl), and cycloSal monophosphate prodrugs.

Pharmaceutically-acceptable salts and prodrugs of these compounds are also intended to be within the scope of the invention.

Representative R$^2$ moieties are shown below:

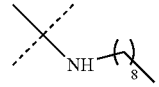

60

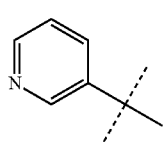

60

65

-continued

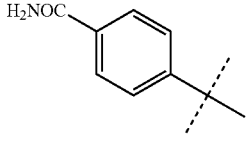

61

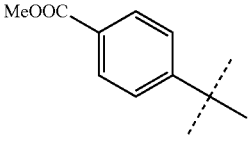

62

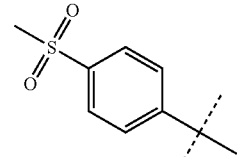

63

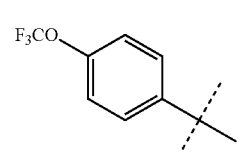

64

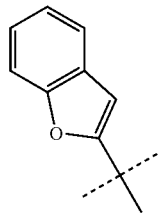

65

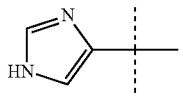

66

Representative R$^3$ moieties are shown below:

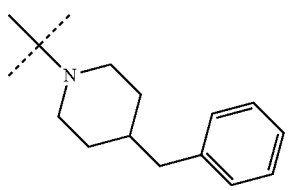

Compound 1

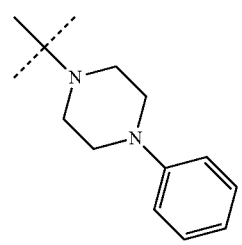

34

35

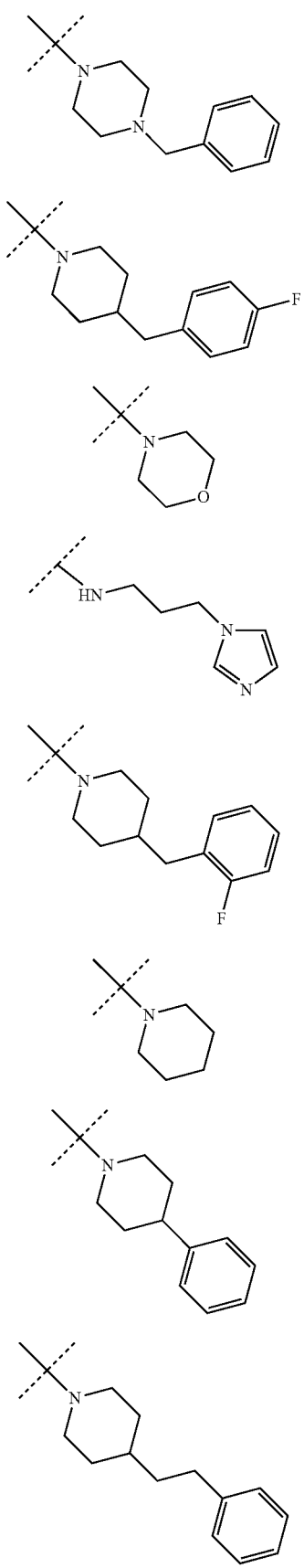

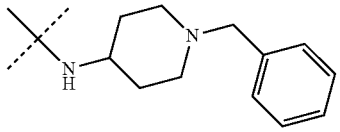

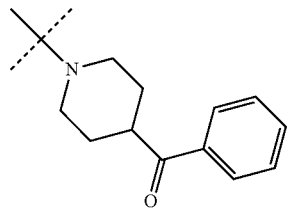

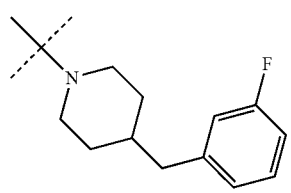

In one embodiment, one of X and Z is —C(O)—, —SO$_2$—, or —NC(O)—, and the other is —NH—, —N(NH$_2$)—, —NH(OH)—, —N(C$_{1-10}$ alkyl)-, —N(C$_{3-10}$ cycloalkyl)-, —N(C$_{2-10}$ alkenyl)-, —N(C$_{2-10}$ alkynyl)-, —N(aryl)-, or —N(heteroaryl)-, or —O—.

In another embodiment, one of X and Z is —C(O)—, —SO$_2$—, or —N(C(O)—, and the other is —CH$_2$—, —CH(C$_{1-6}$ alkyl)-, C(alkyl)$_2$-, —CH(C$_{3-8}$ cycloalkyl)-, —CH(C$_{2-6}$ alkenyl, —CH(C$_{2-6}$ alkynyl)-, —CH(aryl)-, —CH(heteroaryl)-, —CF$_2$—, —CCl$_2$—, —CH(CF$_3$)—, —CH(OH)—, —CH(OAlkyl)-, —CH(NH$_2$)—, —CH(NHAlkyl)-, or —CH(C(O)NH$_2$)—. 4. The compound of claim 1, wherein one of X and Z is —NH—, —N(NH$_2$)—, —NH(OH)—, —N(alkyl)-, or —O— and the other is —CH$_2$—, —CH(C$_{1-6}$ alkyl)-, C(alkyl)$_2$-, —CH(C$_{3-8}$ cycloalkyl)-, —CH(C$_{2-6}$ alkenyl, —CH(C$_{2-6}$ alkynyl)-, —CH(aryl)-, —CH(heteroaryl)-, —CF$_2$—, —CCl$_2$—, —CH(CF$_3$)—, —CH(OH)—, —CH(OAlkyl)-, —CH(NH$_2$)—, —CH(NHAlkyl)-, or —CH(C(O)NH$_2$)—.

In a third embodiment, one of X and Z is —NH—, —N(NH$_2$)—, —NH(OH)—, —N(C$_{1-10}$ alkyl)-, —N(C$_{3-10}$ cycloalkyl)-, —N(C$_{2-10}$ alkenyl)-, —N(C$_{2-10}$ alkynyl)-, —N(aryl)-, or —N(heteroaryl)-, and the other is —C(O)— or —SO$_2$—.

In a fourth embodiment, Y is —NH, —N(NH$_2$)—, —NH(OH)—, —N(C$_{1-10}$ alkyl)-, —N(C$_{3-10}$ cycloalkyl)-, —N(C$_{2-10}$ alkenyl)-, —N(C$_{2-10}$ alkynyl)-, —N(aryl)-, or —N(heteroaryl)-, or —O—.

In a fifth embodiment, Y is —NH, —N(NH$_2$)—, —NH(OH)—, —N(C$_{1-10}$ alkyl)-, —N(C$_{3-10}$ cycloalkyl)-, —N(C$_{2-10}$ alkenyl)-, —N(C$_{2-10}$ alkynyl)-, —N(aryl)-, or —N(heteroaryl)-, In a sixth embodiment, one of R$^1$ and R$^2$ is H, —CH$_2$-phosphonate, —CH$_2$O-phosphate, wherein the term phosphate includes monophosphate, diphosphate, triphosphate, and stabilized phosphate prodrugs, and the term phosphonate includes the same prodrugs that are present in the phosphate prodrugs.

In a seventh embodiment, one of R$^1$ and R$^2$ is H, —CH$_2$P(O)(OH)$_2$, —CH$_2$P(O)(OH)(OR$^6$), —CH$_2$P(O)(OR$^6$)$_2$, —CH$_2$P(O)(OR$^6$)(NR$^6$), —CH$_2$P(O)(NR$^6$)$_2$, —CH$_2$P(O)(OH)(OC$_{1-10}$ alkyl-O—C$_{1-20}$ alkyl), or a —CH$_2$-cycloSal monophosphate prodrug.

In one aspect of this embodiment, one of $R^1$ and $R^2$ is a phosphonate, a phosphoramidate, a cycloSal monophosphate prodrug, or has the formula —$CH_2P(O)(OH)(OC_{1-10}$ alkyl-O—$C_{1-20}$ alkyl).

In a preferred embodiment, one of $R^1$ and $R^2$ is —C(O) NHR$^4$, —C(O)N(R$^4$)$_2$,

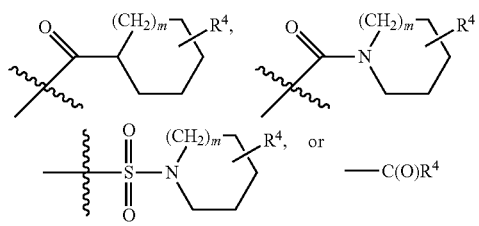

wherein $R^4$ is $C_{1-10}$ alkyl, $C_{3-10}$ cycloalkyl, $C_{2-10}$ alkenyl, $C_{2-10}$ alkynyl, arylalkyl, alkylaryl, $C_{1-10}$ halo alkyl, $C_{1-10}$ alkyl-aryl, or $C_{1-10}$ haloalkyl-aryl and m is 0, 1 or 2. In specific embodiments, $R^4$ is $C_{1-10}$ alkyl-aryl, and benzyl is a particularly preferred $R^4$ substituent.

In another embodiment, one of $R^1$ and $R^2$ is —C(O)—$C_{1-10}$ alkyl, —C(O)-alkylaryl, —C(O)— heterocyclyl-alkylaryl, —C(O)-heterocyclyl-$CH_2$-aryl, —C(O)-heterocyclyl-$CF_2$-aryl, —C(O)— cycloalkyl-alkylaryl, —C(O)NHC$_{1-10}$ alkyl, —C(O)NH-alkylaryl, —C(O)NH-heterocyclyl-alkylaryl, —C(O)NH-heterocyclyl-$CF_2$-aryl, —C(O)NH-cycloalkyl-alkylaryl, —$SO_2$—$C_{1-10}$ alkyl, —$SO_2$-alkylaryl, —$SO_2$-heterocyclyl-alkylaryl, —$SO_2$-heterocyclyl-$CF_2$-aryl, or —$SO_2$-cycloalkyl-alkylaryl.

Representative compounds include the following:

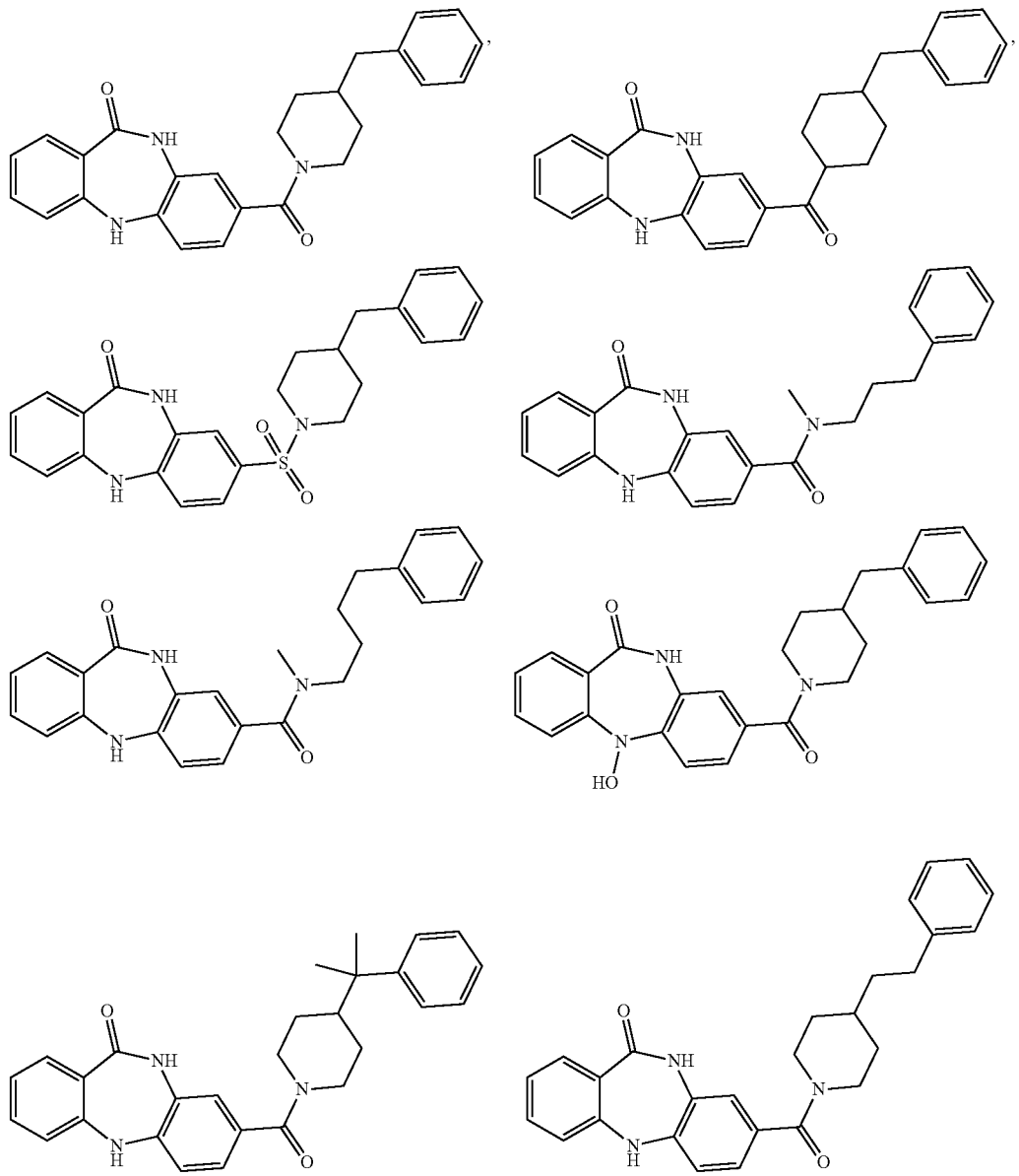

-continued
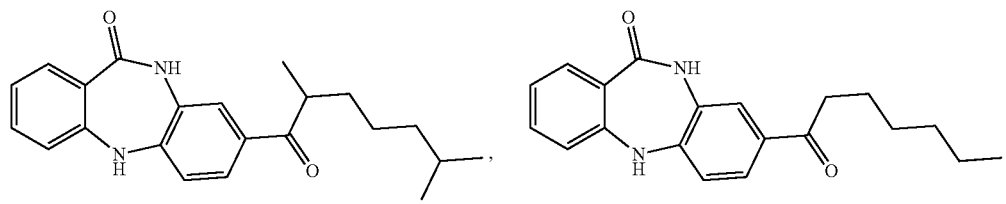
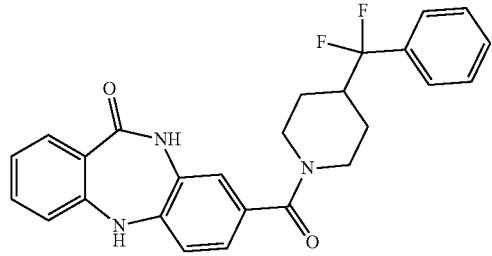
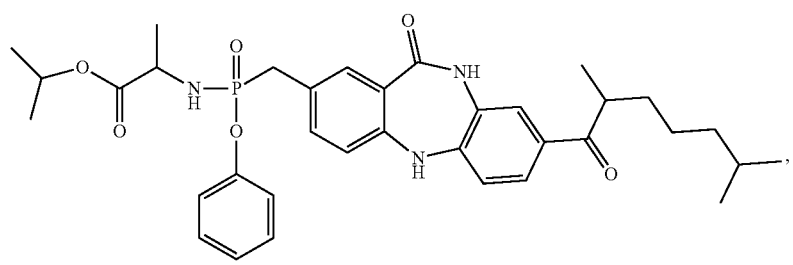
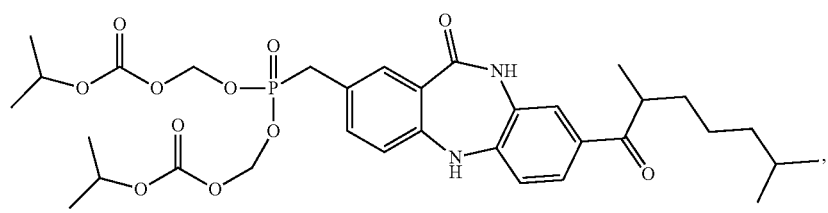
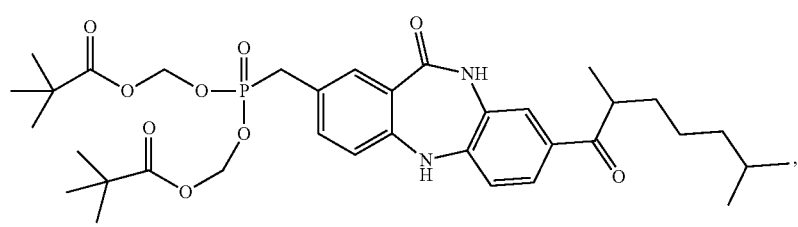
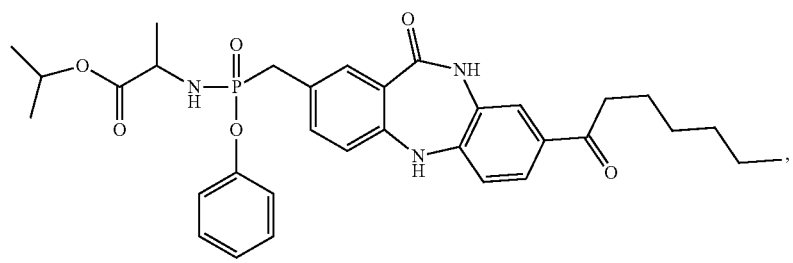
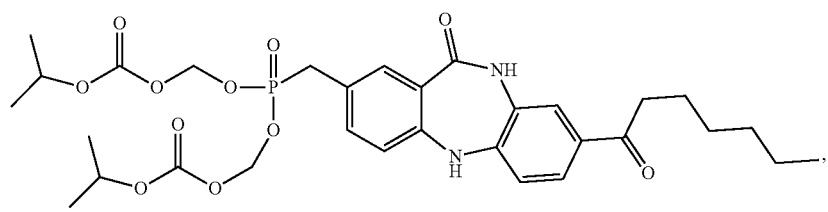

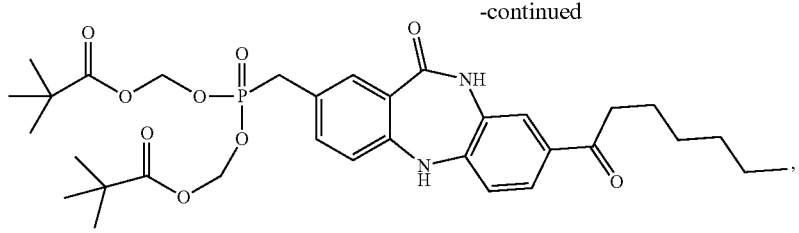

or a pharmaceutically-acceptable salt or prodrug thereof.

A particularly preferred compound has the formula:

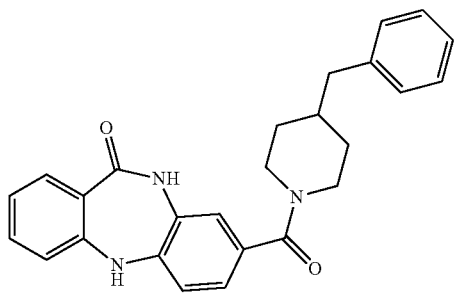 [SMILES: O=C1Nc2cc(C(=O)N3CCC(Cc4ccccc4)CC3)ccc2Nc2ccccc21]

or a pharmaceutically acceptable salt or prodrug thereof.

III Stereoisomerism and Polymorphism

The compounds described herein can have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective compound, then derivatize the compound to form the compounds described herein, or purify the compound themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts can also be formed, including but not limited to, sulfate, nitrate, bicarbonate and carbonate salts. For certain transdermal applications, it can be preferred to use fatty acid salts of the compounds described herein. The fatty acid salts can help penetrate the stratum corneum. Examples of suitable salts include salts of the compounds with stearic acid, oleic acid, lineoleic acid, palmitic acid, caprylic acid, and capric acid.

Pharmaceutically acceptable salts can be obtained using standard procedures well known in the art, for example by reacting a sufficiently basic compound such as an amine with a suitable acid, affording a physiologically acceptable anion. In those cases where a compound includes multiple amine groups, the salts can be formed with any number of the amine groups. Alkali metal (e.g., sodium, potassium or lithium) or alkaline earth metal (e.g., calcium) salts of carboxylic acids can also be made.

A prodrug is a pharmacological substance that is administered in an inactive (or significantly less active) form and subsequently metabolized in vivo to an active metabolite. Getting more drug to the desired target at a lower dose is often the rationale behind the use of a prodrug and is generally attributed to better absorption, distribution, metabolism, and/or excretion (ADME) properties. Prodrugs are usually designed to improve oral bioavailability, with poor absorption from the gastrointestinal tract usually being the limiting factor. Additionally, the use of a prodrug strategy can increase the selectivity of the drug for its intended target thus reducing the potential for off target effects.

V. Methods of Treatment

Hosts can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, transdermally, subcutaneously, or topically, in liquid or solid form. Details of administration are provided in pharmaceutical compositions.

VI. Combination or Alternation Therapy

In one embodiment, a compound of Formula (A) or a pharmaceutically acceptable derivative thereof, can be employed alone, in combination with one or more compounds of formula (A) or a pharmaceutically acceptable derivative thereof, or in combination with at least one other agent in use for treating conditions associated with ROR.

In certain embodiments, a compound of Formula (A) for treatment of a metabolic disorder in combination with an anti-diabetic or anti-insulin resistance agent, such as, but not limited to, a glitazone, a sulfonylurea, metformin, insulin, an insulin mimetic, a DPP4 inhibitor, a GLP1 receptor agonist, a glucagon receptor antagonist, or an anti-obesity agent.

In certain embodiments, a compound of Formula (A) for treatment of an immune disorder in combinations with such as, but not limited to, anti-TNF agent or an immune-suppressive glucocorticoid. In certain embodiments, a compound of formula (A) for treatment of cancer in combination with one or more anticancer agents such as, but not limited to, a platinum compound, a *Vinca* alkaloid or analog thereof, a taxane, a nitrogen mustard, or the like.

Other agents for use in combination for conditions associated with ROR are, but not limited to, the following: cholesterol biosynthesis inhibitors (HMG CoA reductase inhibitors, e.g., lovastatin, simvastatin, pravastatin, fluvastatin, atorvastatin, cerivastatin, nisvastatin and rivastatin); squalene epoxidase inhibitors (e.g. terbinafine); plasma HDL-raising agents (e.g. CETP inhibitors e.g. anacetrapib, R1658); human peroxisome proliferator activated receptor (PPAR) gamma agonists (e.g., thiazolidinediones e.g. rosiglitazone, troglitazone, and pioglitazone); PPAR alpha agonists (e.g. clofibrate, fenofibrate, and gemfibronzil); PPAR dual alpha/gamma agonists (e.g. muraglitazar, aleglitazar, peliglitazar, elafibranor); farnesoid X receptor (FXR) modulators (e.g., obeticholic acid, LMB763, LJN45, etc.); bile acid sequestrants (e.g., anion exchange resins, or quaternary amines (e.g. cholestyramine or colestipol)); bile acid transport inhibitors (BATi); nicotinic acid, niacinamide; cholesterol absorption inhibitors (e.g. ezetimibe); acyl-coenzyme A:cholesterol O-acyl transferase (ACAT) inhibitors (e.g., avasimibe); selective estrogen receptor modulators (e.g. raloxifene or tamoxifen); LXR alpha or beta agonists, antagonists or partial agonists (e.g., 22(R)-hydroxycholesterol, 24(S)-hydroxycholesterol, T0901317 or GW3965); microsomal triglyceride transfer protein (MTP) inhibitors, anti-diabetes agents such as, e.g. insulin and insulin analogs (e.g. LysPro insulin, inhaled formulations comprising insulin; sulfonylureas and analogues (e.g. tolazamide, chlorpropamide, glipizide, glimepiride, glyburide, glibenclamide, tolbutamide, acetohexamide, glypizide), biguanides (e.g., metformin or metformin hydrochloride, phenformin, buformin) alpha2-antagonists and imidazolines (e.g. midaglizole, isaglidole, deriglidole, idazoxan, efaroxan, fluparoxan), thiazolidinediones (e.g., pioglitazone hydrochloride, rosiglitazone maleate, ciglitazone, troglitazone or balaglitazone), alpha-glucosidase inhibitors (e.g. miglitol, acarbose, epalrestat, or voglibose), meglitinides (e.g. repaglinide or nateglinide), DPP-4 inhibitors (e.g., sitagliptin phosphate, saxagliptin, vildagliptin, alogliptin or denagliptin), incretins (e.g. glucagon-like peptide-1 (GLP-1) receptor agonists (e.g.

Exenatide (Byetta™), NN2211 (Liraglutide), GLP-1(7-36) amide and its analogs, GLP-1(7-37) and its analogs, AVE-0010 (ZP-10), R1583 (Taspoglutide), GSK-716155 (albiglutide, GSK/Human Genome Sciences), BRX-0585 (Pfizer/Biorexis) and CJC-1134-PC (Exendin-4:PC-DAC™ and glucose-dependent insulinotropic peptide (GIP)); amylin agonists (e.g. pramlintide, AC-137); insulin secretagogues (e.g. linogliride, nateglinide, repaglinide, mitiglinide calcium hydrate or meglitinide); SGLT-2 inhibitors (e.g. dapagliflozin (BMS), sergliflozin (Kissei), AVE 2268 (Sanofi-Aventis); Glucokinase activators such as the compounds disclosed in e.g. WO 00/58293 A1; anti-obesity agents such as nerve growth factor agonist (e.g. axokine), growth hormone agonists (e.g. AOD-9604), adrenergic uptake inhibitors (e.g. GW-320659), 5-HT (serotonin) reuptake/transporter inhibitors (e.g. Prozac), 5-HT/NA (serotonin/noradrenaline) reuptake inhibitors (e.g. sibutramine), DA (dopamine) reuptake inhibitors (e.g. Buproprion), 5-HT, NA and DA reuptake blockers, steroidal plant extracts (e.g. P57), NPY1 or 5 (neuropeptide Y Y1 or Y5) antagonists, NPY2 (neuropeptide Y Y2) agonists, MC4 (melanocortin 4) agonists, CCK-A (cholecystokinin-A) agonists, GHSR1a (growth hormone secretagogue receptor) antagonist/inverse agonists, ghrelin antibody, MCH1R (melanin concentrating hormone 1R) antagonists (e.g. SNAP 7941), MCH2R (melanin concentrating hormone 2R) agonist/antagonists, H3 (histamine receptor 3) inverse agonists or antagonists, H1 (histamine 1 receptor) agonists, FAS (Fatty acid synthase) inhibitors, ACC-1 (acetyl-CoA carboxylase-1) inhibitors, β3 (beta adrenergic receptor 3) agonists, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, GLP-1 (glucagons-like peptide-1) agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), NN2211, Topiramate, glucocorticoid antagonist, Exendin-4 agonists, 5-HT2C (serotonin receptor 2C) agonists (e.g. Lorcaserin), PDE (phosphodiesterase) inhibitors, fatty acid transporter inhibitors, dicarboxylate transporter inhibitors, glucose transporter inhibitors, CB-1 (cannabinoid-1 receptor) inverse agonists or antagonists (e.g. SR141716), lipase inhibitors (e.g., orlistat); cyclooxygenase-2 (COX-2) inhibitors (e.g. rofecoxib and celecoxib); thrombin inhibitors (e.g., heparin, argatroban, melagatran, dabigatran); platelet aggregation inhibitors (e.g. glycoprotein IIb/IIIa fibrinogen receptor antagonists or aspirin); vitamin B6 and pharmaceutically acceptable salts thereof; vitamin B 12; vitamin E; folic acid or a pharmaceutically acceptable salt or ester thereof; antioxidant vitamins such as C and E and beta carotene; beta blockers (e.g. angiotensin II receptor antagonists such as losartan, irbesartan or valsartan; antiotensin converting enzyme inhibitors such as enalapril and captopril; calcium channel blockers such as nifedipine and diltiazam; endothelian antagonists; aspirin; fatty-acid/bile-acid conjugates (Aramchol); caspase inhibitors (emricasan); immunomodulators (Cenicriviroc, etc.); thyroid hormone receptor modulators (MB07811, MGL-3196, etc.); agents other than LXR ligands that enhance ATP-Binding Cassette Transporter-A1 gene expression; and bisphosphonate compounds (e.g., alendronate sodium).

In certain embodiments, a compound of Formula (A) in combination with at least one other agent that modifies host metabolism such as, but not limited to, clarithromycin, cobicistat, indinavir, itraconazole, ketoconazole, nefazodone, ritonavir, saquinavir, suboxone, telithromycin, aprepitant, erythromycin, fluconazole, verapamil, diltiazem, cimetidine, amiodarone, boceprevir, chloramphenicol, ciprofloxacin, delaviridine, diethyl-dithiocarbamate, fluvoxamine, gestodene, imatinib, mibefradil, mifepristone, norfloxacin, norfluoxetine, telaprevir, and voriconazole.

Additional compounds which can be co-administered include one or more of glutathione, di and trimethyl glycine, choline, acetyl choline, niacin, magnesium, vitamin D, cucurmin, berberine, Coenzyme Q10, and sylmarin (milk thistle).

VIII. Pharmaceutical Compositions

Hosts, including but not limited to humans, affected by liver or metabolic diseases such as, but not limited to, increased lipid and cholesterol levels, particularly high LDL-cholesterol, high triglycerides, low HDL-cholesterol, dyslipidemia, diseases of cholesterol absorption, atherosclerotic disease, corony artery disease, cerebrovascular arterial disease, peripheral vascular disease, aortic aneurysms, carotid atherosclerotic conditions, cholestatic disorders, peripheral occlusive disease, ischemic stroke, diabetes, particularly non-insulin dependent diabetes mellitus, metabolic syndrome, diabetic nephropathy, obesity (where the treatment of obesity can result in weight loss), cholesterol gallstone disease, cholestasis/fibrosis of the liver, primary biliary cirrhosis (PBC), primary sclerosing cholangitis (PSC), non-alcoholic steatohepatitis (NASH), alcoholic steatohepatitis (ASH), hepatic ischemia reperfusion injury, or non-alcoholic fatty liver disease (NAFLD); autoimmune disorders such as, but not limited to, rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, Pernicious anemia, chronic graft-versus-host disease, acute graft-versus-host disease, Celiac Sprue, idiopathic thrombocytopenic thrombotic purpura, myasthenia gravis, Sjorgren's syndrome, scleroderma, ulcerative colitis, epidermal hyperplasia, glomerulonephritis, chronic obstructive pulmonary disease (COPD) and amyotrophic lateral sclerosis; or central nervous system (CNS) diseases associated with ROR such as, but not limited to, sleep disorder, anxiety, or neurodegenerative disease such as Parkinson's or Alzheimer's; or cancers such as, but not limited to, colon cancer, prostate cancer, breast cancer, lymphoid cancers, brain cancers, myeloid cancer, etc., can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for will be in the range of between about 0.01 and about 10 mg/kg, more generally, between about 0.1 and 5 mg/kg, and, preferably, between about 0.5 and about 2 mg/kg, of body weight of the recipient per day. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to but not limited to one containing 7 to 600 mg, preferably 70 to 600 mg of active ingredient per unit dosage form. An oral dosage of 5-400 mg is usually convenient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antiviral compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Transdermal Formulations

In some embodiments, the compositions are present in the form of transdermal formulations, such as that used in the FDA-approved agonist rotigitine transdermal (Neupro patch). Another suitable formulation is that described in U.S. Publication No. 20080050424, entitled "Transdermal Therapeutic System for Treating Parkinsonism." This formulation includes a silicone or acrylate-based adhesive, and can include an additive having increased solubility for the active substance, in an amount effective to increase dissolving capacity of the matrix for the active substance.

The transdermal formulations can be single-phase matrices that include a backing layer, an active substance-containing self-adhesive matrix, and a protective film to be removed prior to use. More complicated embodiments contain multiple-layer matrices that may also contain non-adhesive layers and control membranes. If a polyacrylate adhesive is used, it can be crosslinked with multivalent metal ions such as zinc, calcium, aluminum, or titanium ions, such as aluminum acetylacetonate and titanium acetylacetonate.

When silicone adhesives are used, they are typically polydimethylsiloxanes. However, other organic residues such as, for example, ethyl groups or phenyl groups may in principle be present instead of the methyl groups. Because the active compounds are amines, it may be advantageous to use amine-resistant adhesives. Representative amine-resistant adhesives are described, for example, in EP 0 180 377.

Representative acrylate-based polymer adhesives include acrylic acid, acrylamide, hexylacrylate, 2-ethylhexylacrylate, hydroxyethylacrylate, octylacrylate, butylacrylate, methylacrylate, glycidylacrylate, methacrylic acid, methacrylamide, hexylmethacrylate, 2-ethylhexylmethacrylate, octylmethacrylate, methylmethacrylate, glycidylmethacrylate, vinylacetate, vinylpyrrolidone, and combinations thereof.

The adhesive must have a suitable dissolving capacity for the active substance, and the active substance most be able to move within the matrix, and be able to cross through the contact surface to the skin. Those of skill in the art can readily formulate a transdermal formulation with appropriate transdermal transport of the active substance.

Certain pharmaceutically acceptable salts tend to be more preferred for use in transdermal formulations, because they can help the active substance pass the barrier of the stratum corneum. Examples include fatty acid salts, such as stearic acid and oleic acid salts. Oleate and stearate salts are relatively lipophilic, and can even act as a permeation enhancer in the skin.

Permeation enhancers can also be used. Representative permeation enhancers include fatty alcohols, fatty acids, fatty acid esters, fatty acid amides, glycerol or its fatty acid esters, N-methylpyrrolidone, terpenes such as limonene, alpha-pinene, alpha-terpineol, carvone, carveol, limonene oxide, pinene oxide, and 1,8-eucalyptol.

The patches can generally be prepared by dissolving or suspending the active agent in ethanol or in another suitable organic solvent, then adding the adhesive solution with stirring. Additional auxiliary substances can be added either to the adhesive solution, the active substance solution or to the active substance-containing adhesive solution. The solution can then be coated onto a suitable sheet, the solvents removed, a backing layer laminated onto the matrix layer, and patches punched out of the total laminate.

Nanoparticulate Compositions

The compounds described herein can also be administered in the form of nanoparticulate compositions. In one embodiment, controlled release nanoparticulate formulations comprise a nanoparticulate active agent to be administered and a rate-controlling polymer which prolongs the release of the agent following administration. In this embodiment, the compositions can release the active agent, following administration, for a time period ranging from about 2 to about 24 hours or up to 30 days or longer. Representative controlled release formulations including a nanoparticulate form of the active agent are described, for example, in U.S. Pat. No. 8,293,277.

Nanoparticulate compositions can comprise particles of the active agents described herein, having a non-crosslinked surface stabilizer adsorbed onto, or associated with, their surface.

The average particle size of the nanoparticulates is typically less than about 800 nm, more typically less than about 600 nm, still more typically less than about 400 nm, less than about 300 nm, less than about 250 nm, less than about 100 nm, or less than about 50 nm. In one aspect of this embodiment, at least 50% of the particles of active agent have an average particle size of less than about 800, 600, 400, 300, 250, 100, or 50 nm, respectively, when measured by light scattering techniques.

A variety of surface stabilizers are typically used with nanoparticulate compositions to prevent the particles from clumping or aggregating. Representative surface stabilizers are selected from the group consisting of gelatin, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol, polyvinylpyrrolidone, tyloxapol, poloxamers, poloxamines, poloxamine 908, dialkylesters of sodium sulfosuccinic acid, sodium lauryl sulfate, an alkyl aryl polyether sulfonate, a mixture of sucrose stearate and sucrose distearate, p-isononylphenoxy-poly-(glycidol), SA90HCO, decanoyl-N-methylglucamide, n-decyl-D-glucopyranoside, n-decyl-D-maltopyranoside, n-dodecyl-D-glucopyranoside, n-dodecyl-D-maltoside, heptanoyl-N-methylglucamide, n-heptyl-D-glucopyranoside, n-heptyl-D-thioglucoside, n-hexyl-D-glucopyranoside, nonanoyl-N-methylglucamide, n-nonyl-D-glucopyranoside, octanoyl-N-methylglucamide, n-octyl-D-glucopyranoside, and octyl-D-thioglucopyranoside. Lysozymes can also be used as surface stabilizers for nanoparticulate compositions. Certain nanoparticles such as poly(lactic-co-glycolic acid) (PLGA)-nanoparticles are known to target the liver when given by intravenous (IV) or subcutaneously (SQ).

Representative rate controlling polymers into which the nanoparticles can be formulated include chitosan, polyethylene oxide (PEO), polyvinyl acetate phthalate, gum arabic, agar, guar gum, cereal gums, dextran, casein, gelatin, pectin, carrageenan, waxes, shellac, hydrogenated vegetable oils, polyvinylpyrrolidone, hydroxypropyl cellulose (HPC), hydroxyethyl cellulose (HEC), hydroxypropyl methylcellulose (HPMC), sodium carboxymethylcellulose (CMC), poly (ethylene) oxide, alkyl cellulose, ethyl cellulose, methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly(alkylmethacrylate), poly (vinyl acetate), polymers derived from acrylic or methacrylic acid and their respective esters, and copolymers derived from acrylic or methacrylic acid and their respective esters.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Nonionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anhydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive nanoparticulate compositions having cationic surface stabilizers;" U.S. Pat. No. 6,431,478 for "Small Scale Mill;" and U.S. Pat. No. 6,432,381 for "Methods for targeting drug delivery to the upper and/or lower gastrointestinal tract," all of which are specifically incorporated by reference. In addition, U.S. Patent Application No. 20020012675 A1, published on Jan. 31, 2002, for "Controlled Release Nanoparticulate Compositions," describes nanoparticulate compositions, and is specifically incorporated by reference.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

Certain nanoformulations can enhance the absorption of drugs by releasing drug into the lumen in a controlled manner, thus reducing solubility issues. The intestinal wall is designed to absorb nutrients and to act as a barrier to pathogens and macromolecules. Small amphipathic and lipophilic molecules can be absorbed by partitioning into the lipid bilayers and crossing the intestinal epithelial cells by passive diffusion, while nanoformulation absorption may be more complicated because of the intrinsic nature of the intestinal wall. The first physical obstacle to nanoparticle oral absorption is the mucus barrier which covers the luminal surface of the intestine and colon. The mucus barrier contains distinct layers and is composed mainly of heavily glycosylated proteins called mucins, which have the potential to block the absorption of certain nanoformulations. Modifications can be made to produce nanoformulations with increased mucus-penetrating properties (Ensign et al., "Mucus penetrating nanoparticles: biophysical tool and method of drug and gene delivery," Adv Mater 24: 3887-3894 (2012)).

Once the mucus coating has been traversed, the transport of nanoformulations across intestinal epithelial cells can be regulated by several steps, including cell surface binding, endocytosis, intracellular trafficking and exocytosis, resulting in transcytosis (transport across the interior of a cell) with the potential involvement of multiple subcellular structures. Moreover, nanoformulations can also travel between cells through opened tight junctions, defined as paracytosis. Non-phagocytic pathways, which involve clathrin-mediated and caveolae-mediated endocytosis and macropinocytosis, are the most common mechanisms of nanoformulation absorption by the oral route.

Non-oral administration can provide various benefits, such as direct targeting to the desired site of action and an extended period of drug action. Transdermal administration has been optimized for nanoformulations, such as solid lipid nanoparticles (SLNs) and NEs, which are characterized by good biocompatibility, lower cytotoxicity and desirable drug release modulation (Cappel and Kreuter, "Effect of nanoparticles on transdermal drug delivery. J Microencapsul 8: 369-374 (1991)). Nasal administration of nanoformulations allows them to penetrate the nasal mucosal membrane, via a transmucosal route by endocytosis or via a carrier- or receptor-mediated transport process (Illum, "Nanoparticulate systems for nasal delivery of drugs: a real improvement over simple systems?" J. Pharm. Sci 96: 473-483 (2007)), an example of which is the nasal administration of chitosan nanoparticles of tizanidine to increase brain penetration and drug efficacy in mice (Patel et al., "Improved transnasal transport and brain uptake of tizanidine HCl-loaded thiolated chitosan nanoparticles for alleviation of pain," J.

Pharm. Sci 101: 690-706 (2012)). Pulmonary administration provides a large surface area and relative ease of access. The mucus barrier, metabolic enzymes in the tracheobronchial region and macrophages in the alveoli are typically the main barriers for drug penetration. Particle size is a major factor determining the diffusion of nanoformulation in the bronchial tree, with particles in the nano-sized region more likely to reach the alveolar region and particles with diameters between 1 and 5 μm expected to deposit in the bronchioles (Musante et al., "Factors affecting the deposition of inhaled porous drug particles," J Pharm Sci 91: 1590-1600 (2002)). A limit to absorption has been shown for larger particles, presumably because of an inability to cross the air-blood barrier. Particles can gradually release the drug, which can consequently penetrate into the blood stream or, alternatively, particles can be phagocytosed by alveolar macrophages (Bailey and Berkland, "Nanoparticle formulations in pulmonary drug delivery," Med. Res. Rev., 29: 196-212 (2009)).

Certain nanoformulations have a minimal penetration through biological membranes in sites of absorption and for these, i.v. administration can be the preferred route to obtain an efficient distribution in the body (Wacker, "Nanocarriers for intravenous injection—The long hard road to the market," Int. J. Pharm., 457: 50-62., 2013).

The distribution of nanoformulations can vary widely depending on the delivery system used, the characteristics of the nanoformulation, the variability between individuals, and the rate of drug loss from the nanoformulations. Certain nanoparticles, such as solid drug nanoparticles (SDNs), improve drug absorption, which does not require them to arrive intact in the systemic circulation. Other nanoparticles survive the absorption process, thus altering the distribution and clearance of the contained drug.

Nanoformulations of a certain size and composition can diffuse in tissues through well-characterized processes, such as the enhanced permeability and retention effect, whereas others accumulate in specific cell populations, which allows one to target specific organs. Complex biological barriers can protect organs from exogenous compounds, and the blood-brain barrier (BBB) represents an obstacle for many therapeutic agents. Many different types of cells including endothelial cells, microglia, pericytes and astrocytes are present in the BBB, which exhibits extremely restrictive tight junctions, along with highly active efflux mechanisms, limiting the permeation of most drugs. Transport through the BBB is typically restricted to small lipophilic molecules and nutrients that are carried by specific transporters. One of the most important mechanisms regulating diffusion of nanoformulations into the brain is endocytosis by brain capillary endothelial cells.

Recent studies have correlated particle properties with nanoformulation entry pathways and processing in the human BBB endothelial barrier, indicating that uncoated nanoparticles have limited penetration through the BBB and that surface modification can influence the efficiency and mechanisms of endocytosis (Lee et al., "Targeting rat anti-mouse transferrin receptor monoclonal antibodies through blood-brain barrier in mouse," J. Pharmacol. Exp. Ther. 292: 1048-1052 (2000)). Accordingly, surface-modified nanoparticles which cross the BBB, and deliver one or more of the compounds described herein, are within the scope of the invention.

Macrophages in the liver are a major pool of the total number of macrophages in the body. Kupffer cells in the liver possess numerous receptors for selective phagocytosis of opsonized particles (receptors for complement proteins and for the fragment crystallizable part of IgG). Phagocytosis can provide a mechanism for targeting the macrophages, and providing local delivery (i.e., delivery inside the macrophages) of the compounds described herein.

Nanoparticles linked to polyethylene glycol (PEG) have minimal interactions with receptors, which inhibits phagocytosis by the mononuclear phagocytic system (Bazile et al., "Stealth Me.PEG-PLA nanoparticles avoid uptake by the mononuclear phagocytes system," J. Pharm. Sci. 84: 493-498 (1995)).

Representative nanoformulations include inorganic nanoparticles, SDNs, SLNs, NEs, liposomes, polymeric nanoparticles and dendrimers. The compounds described herein can be contained inside a nanoformulation, or, as is sometimes the case with inorganic nanoparticles and dendrimers, attached to the surface. Hybrid nanoformulations, which contain elements of more than one nanoformulation class, can also be used.

SDNs are lipid-free nanoparticles, which can improve the oral bioavailability and exposure of poorly water-soluble drugs (Chan, "Nanodrug particles and nanoformulations for drug delivery," Adv. Drug. Deliv. Rev. 63: 405 (2011)). SDNs include a drug and a stabilizer, and are produced using 'top-down' (high pressure homogenization and wet milling) or bottom-up (solvent evaporation and precipitation) approaches.

SLNs consist of a lipid (or lipids) which is solid at room temperature, an emulsifier and water. Lipids utilized include, but are not limited to, triglycerides, partial glycerides, fatty acids, steroids and waxes. SLNs are most suited for delivering highly lipophilic drugs.

Liquid droplets of less than a 1000 nm dispersed in an immiscible liquid are classified as NEs. NEs are used as carriers for both hydrophobic and hydrophilic agents, and can be administered orally, transdermally, intravenously, intranasally, and ocularly. Oral administration can be preferred for chronic therapy, and NEs can effectively enhance oral bioavailability of small molecules, peptides and proteins.

Polymeric nanoparticles are solid particles typically around 200-800 nm in size, which can include synthetic and/or natural polymers, and can optionally be pegylated to minimize phagocytosis. Polymeric nanoparticles can increase the bioavailability of drugs and other substances, compared with traditional formulations. Their clearance depends on several factors, including the choice of polymers (including polymer size, polymer charge and targeting ligands), with positively charged nanoparticles larger than 100 nm being eliminated predominantly via the liver (Alexis et al., Factors affecting the clearance and biodistribution of polymeric nanoparticles. Mol Pharm 5: 505-515 (2008)).

Dendrimers are tree-like, nanostructured polymers which are commonly 10-20 nm in diameter.

Liposomes are spherical vesicles which include a phospholipid bilayer. A variety of lipids can be utilized, allowing for a degree of control in degradation level. In addition to oral dosing, liposomes can be administered in many ways, including intravenously (McCaskill et al., 2013), transdermally (Pierre and Dos Santos Miranda Costa, 2011), intravitreally (Honda et al., 2013) and through the lung (Chattopadhyay, 2013). Liposomes can be combined with synthetic polymers to form lipid-polymer hybrid nanoparticles, extending their ability to target specific sites in the body. The clearance rate of liposome-encased drugs is determined by both drug release and destruction of liposomes (uptake of liposomes by phagocyte immune cells, aggregation, pH-sensitive breakdown, etc.) (Ishida et al., "Liposome clearance," Biosci Rep 22: 197-224 (2002)).

One or more of these nanoparticulate formulations can be used to deliver the active agents described herein to the macrophages, across the blood brain barrier, and other locations as appropriate.

Controlled Release Formulations

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

The terms used in describing the invention are commonly used and known to those skilled in the art. As used herein, the following abbreviations have the indicated meanings:

DCM Dichloromethane
DIPEA N,N-Diisopropylethylamine
DME Dimethoxyethane
DMF Dimethylformamide
DMSO Dimethyl sulfoxide
EDCI N-(3-Dimethylaminopropyl)-N-ethylcarbodiimide hydrochloride
EtOAc ethyl acetate
HATU 1-[Bis(dimethylamino)methylene]-1H-1,2,3-triazolo[4,5-b]pyridinium 3-oxid hexafluorophosphate
HOBt Hydroxybenzotriazole
MeOH Methanol
THE tetrahydrofuran
X-phos 2-Dicyclohexylphosphino-2',4',6'-triisopropylbiphenyl IX. General Methods for Preparing Active Compounds Methods for the facile preparation of active compounds are known in the art and result from the selective combination known methods. The compounds disclosed herein can be prepared as described in detail below, or by other methods known to those skilled in the art. It will be understood by one of ordinary skill in the art that variations of detail can be made without departing from the spirit and in no way limiting the scope of the present invention.

The various reaction schemes are summarized below.
Scheme 1 Synthetic approach to compound 5.
Scheme 2 Alternate synthetic approach to intermediate 4.
Scheme 3 Synthetic approach to compounds 8 and 10.
Scheme 4 An alternate synthetic approach to compound 8 and 10.
Scheme 5 Synthetic approach to compounds of general formula 15.
Scheme 6 Synthetic approach to compounds of general formula 16.
Scheme 7 Synthetic approach to compounds of general formula 17.
Scheme 8 Synthetic approach to compounds of general formula 22.
Scheme 9 Alternative synthetic approach to compounds of general formula 22.

Compounds of general Formula A can be accomplished by one of ordinary skill in the art, using methods outlined in: (a) Wang, L.; Sullivan, G. M.; Hexamer, L. A.; Hasvold, L. A.; Thalji, R.; Przytulinska, M.; Tao, Z. F.; Li, G.; Chen, Z.; Xiao, Z.; Gu, W. Z; Xue, J.; Bui, M. H.; Merta, P.; Kovar, P.; Bouska, J. J.; Zhang, H.; Park, C.; Stewart, K. D.; Sham, H. L.; Sowin, T. J.; Rosenberg, S. H.; Lin, N. H. *J. Med. Chem.*, 2007, 50 (17), 4162-4176; b) Hasvold L A1, Wang L, Przytulinska M, Xiao Z, Chen Z, Gu W Z, Merta P J, Xue J, Kovar P, Zhang H, Park C, Sowin T J, Rosenberg S H, Lin N H. *Bioorg. Med. Chem. Lett.* 2008, 18, 2311-2315; c) Giannotti, D.; Viti, G.; Sbraci, P.; Pestellini, V.; Volterra, G.; Borsini, F.; Lecci, A.; Meli, A.; Dapporto, P.; Paoli, P. *J. Med. Chem.*, 1991, 34, 1356-1362; c) Ramirez-Martinez, J. F.; Gonziláz-Chávez, R.; Guerrero-Alba, R.; Reyes-Gutiérrez, P. E.; Martinez, R.; Miranda-Morales, M.; Espinosa-Luna, R.; Gonziláz-Chávez, M. M.; Barajas-López, C. *Molecules*, 2013, 18, 894-913 and by general Schemes 1-9.

In the schemes described herein, if an intermediate includes functional groups that might interfere with, or be decomposed or otherwise converted during certain steps, such functional groups can be protected using suitable protecting groups. After these steps, protected functional groups, if any, can be deprotected.

Scheme 1 Synthetic approach to compound 5.

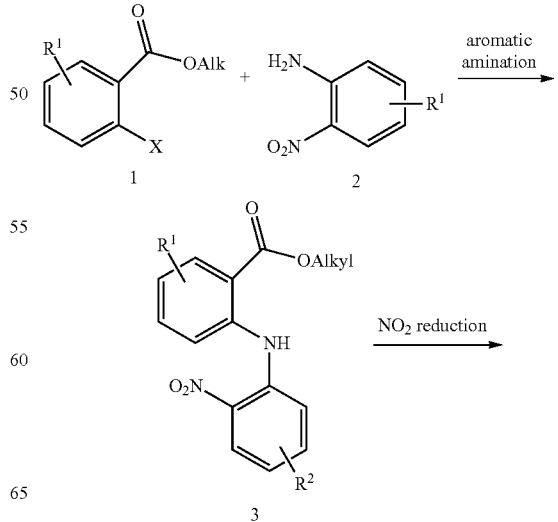

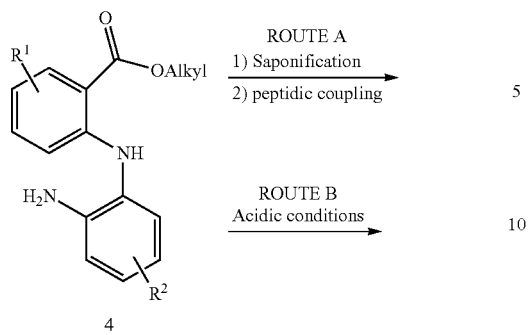

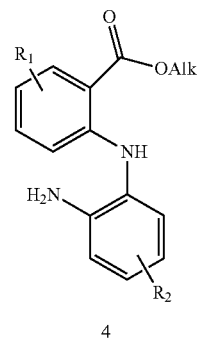

Alk = alkyl
X = halogen
R[1], R[2] are defined in active compound section
R[1], R[2] may contain suitable protection Compounds of general formula 4 can also be prepared by reaction compound of general formula 1 with a diamine of general formula 6 in the presence of Cu and an inorganic base such a $K_2CO_3$, $Na_2CO_3$ or $Cs_2CO_3$.

Scheme 3 Synthetic approach to compounds 8 and 10.

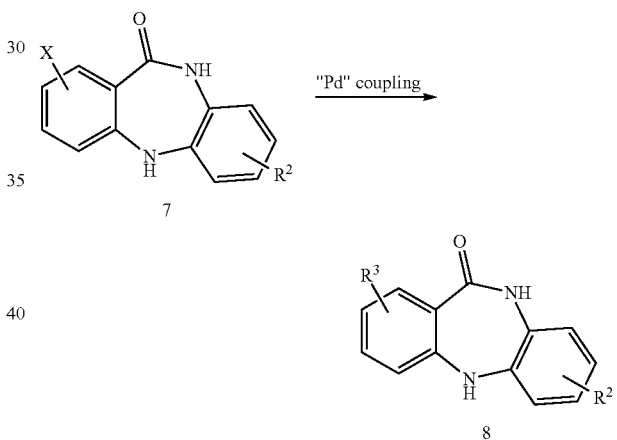

X = halogen
R[1], R[2] are as defined in active compound section
R[1], R[2] may contain suitable protection Compound 5 can be obtained, for instance, by the chemistry described in Scheme 1. Reaction of a compound of general formula 1 with an appropriately substituted nitro aniline of general formula 2 in the presence of Cu and an inorganic base such a $K_2CO_3$, $Na_2CO_3$ or $Cs_2CO_3$ can provide intermediate 3. Reduction of the nitro group using for instance Pt/C in the presence of hydrogen in an alcoholic solvent system or $SnCl_2$ in EtOAc can give compound of general formula 4. Compound 4 can be cyclized in the presence of an acid such as HCl or p-toluene sulfonic acid (Route B). Alternatively, compound 4 can be treated in basic condition with for instance LiOH in a mixture of water and THF to give an acid intermediate which can be then cyclized under classic peptidic conditions using a coupling agent such as HATU in presence of an organic base such as $Et_3N$ (Route A).

Scheme 2 Alternate synthetic approach to intermediate 4.

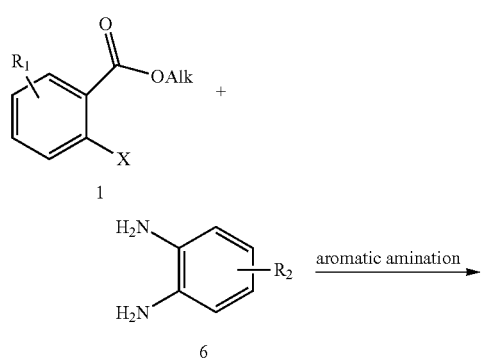

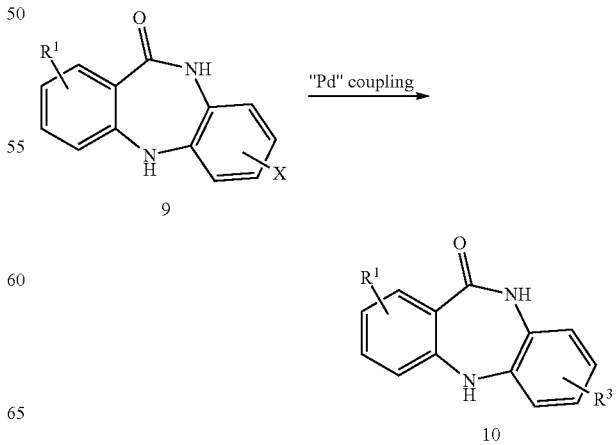

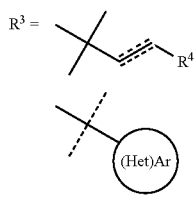

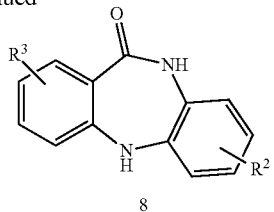

Compounds of general formulas 8 and 10 can be obtained from compounds of general formula 7 or 9 where X is a leaving group such as a halogen, a triflate, a mesylate or a tosylate, by coupling of an alkyne, an alkyl, an alkene, an organoborane or an organostannane derivative under classical palladium catalyzed Sonogashira, Heck, Suzuki or Stille coupling conditions.

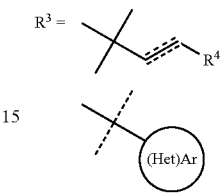

Alternatively, compounds of general formulas 8 and 10 can be prepared by borylation of compounds of general formulas 7 or 9, where X is a leaving group such as a halogen, a triflate, a mesylate or a tosylate. Intermediate 11 and 12 can then be reacted, under classical palladium catalyzed Suzuki coupling conditions, with an aryl, a heteroaryl, an alkene, an alkyne containing a leaving group such as a halogen, a triflate, a mesylate or a tosylate.

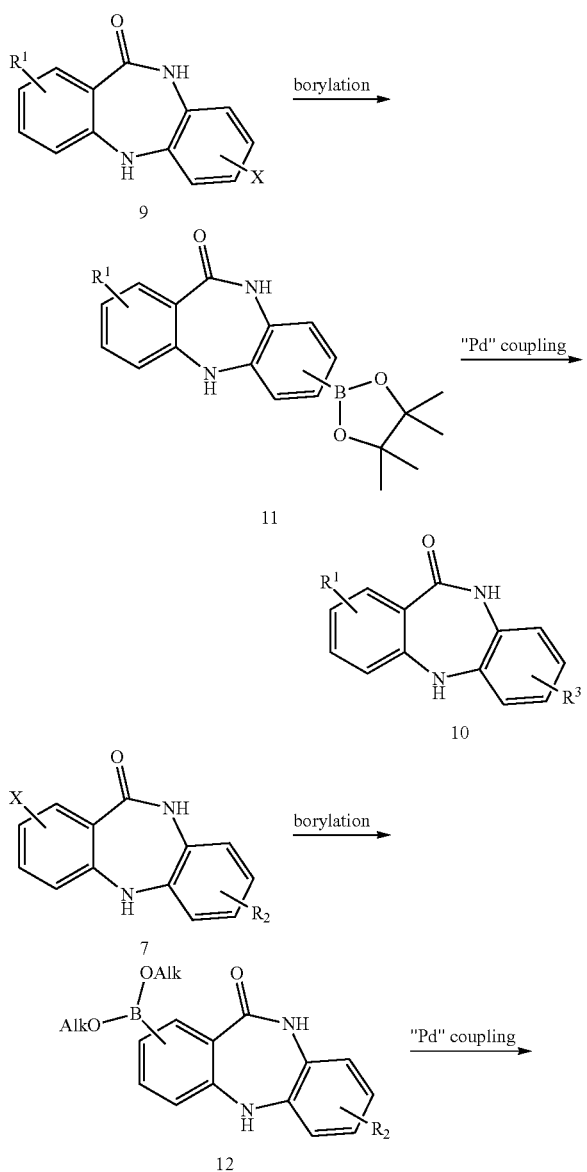

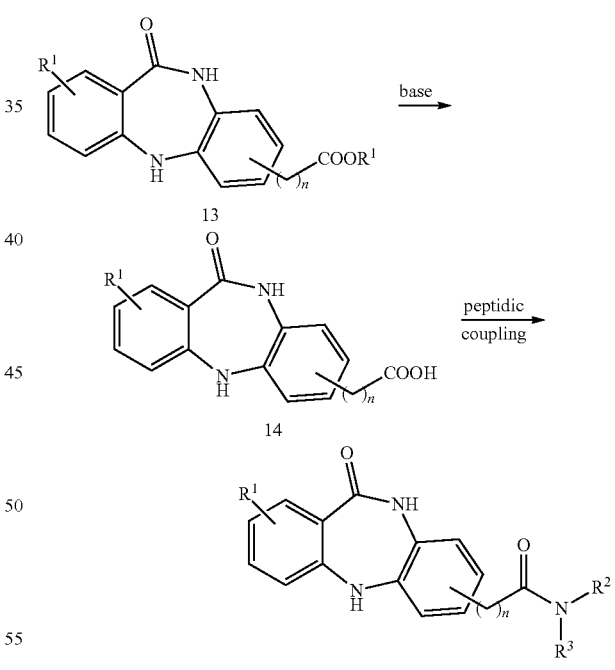

In one embodiment, $R^2$ and $R^3$ combine to form a heterocyclic ring, which can include five to seven-membered rings.

Compounds of general formula 15 can be prepared from esters of general formula, obtained from the chemistry described above, by treatment in basic condition with, for instance, LiOH in a mixture of water and THF to give an acid intermediate which can be then coupled with an amine under classic peptidic conditions using a coupling agent such as HATU in presence of an organic base such as Et₃N.

Scheme 6 Synthetic approach to compounds of general formula 16.

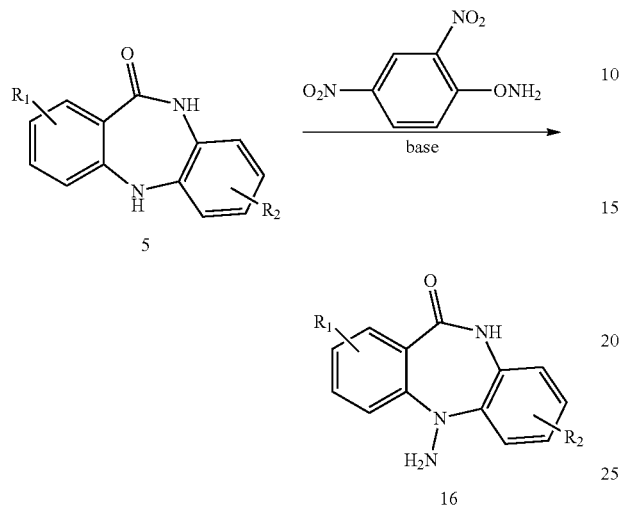

Compounds of general formula 16 can be obtained by treatment with an aminating agent such as O-(2,4-dinitrophenyl)hydroxylamine in presence of a base.

Scheme 7 Synthetic approach to compounds of general formula 17.

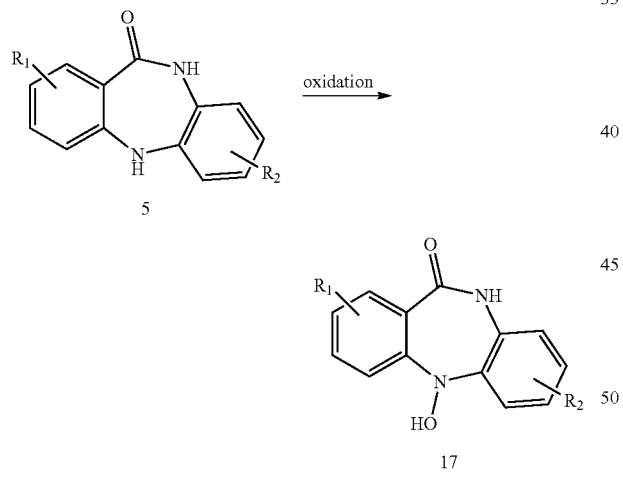

Compounds of general formula 17 can be obtained by treatment with an oxidizing agent such as mCPBA.

Scheme 8. Synthetic approach to compounds of general formula 22.

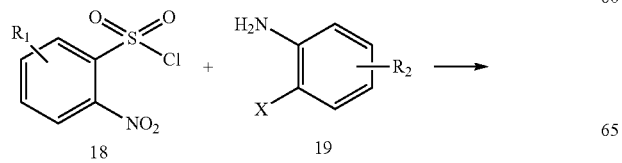

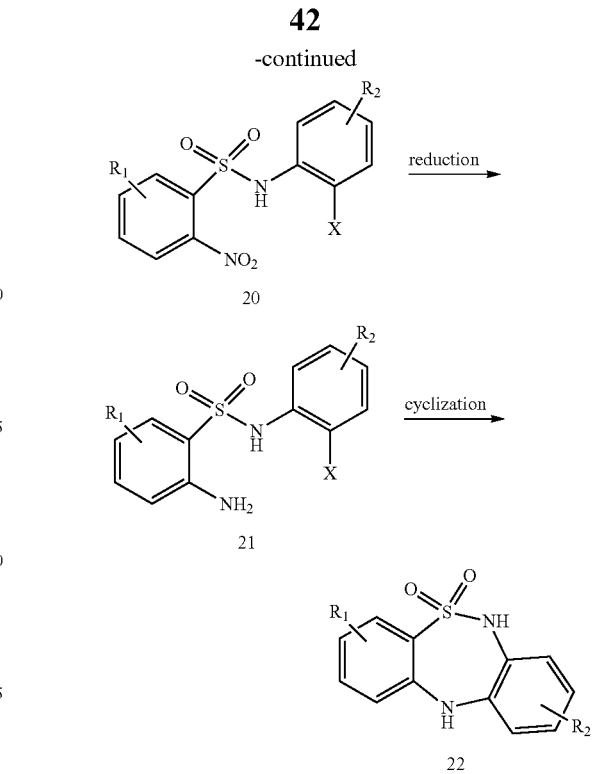

X = halogen
R¹, R² are defined in active compound section and may contain suitable protection Compounds of general formula 22 can be obtained by the chemistry described in Scheme 8. Reaction of a compound of general formula 18 with an appropriately substituted aniline of general formula 19 in the presence an organic base such as pyridine or trimethylamine can provide intermediate 20. Reduction of the nitro group using for instance Pt/C in the presence of hydrogen in an alcoholic solvent system or SnCl₂ in EtOAc can give compound of general formula 21. Compound 21 can be cyclized in the presence of Cu and an inorganic base such a K₂CO₃, Na₂CO₃ or Cs₂CO₃.

Scheme 9 Alternative synthetic approach to compounds of general formula 22.

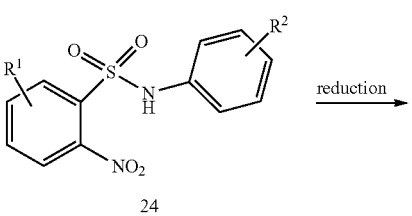

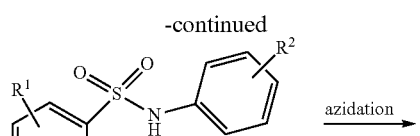

25

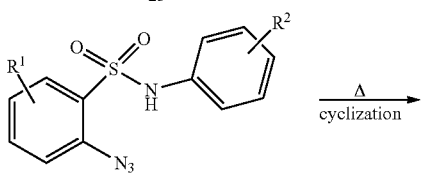

26

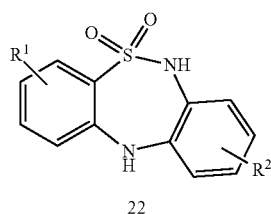

22

$R^1$, $R^2$ are defined in active compound section and may contain suitable protection Alternatively, compounds of general formula 22 can be obtained through the chemistry described in Scheme 9. Reaction of a compound of general formula 18 can react with an appropriately substituted aniline of general formula 23 in the presence an organic base such as pyridine or triethylamine to provide intermediate 24. Reduction of the nitro group using for instance Pt/C in the presence of hydrogen in an alcoholic solvent system or $SnCl_2$ in EtOAc can give compound of general formula 25. Azidation of 25 can be performed using, for instance, $NaNO_2$, $CF_3COOH$ and $NaN_3$ to give compounds of general formula 26. Compounds 26 can be cyclized at high temperature in a high boiling point solvents such as dihexyl ether.

Substitution of Aromatic Rings

In various reaction schemes shown above, the aromatic rings are substituted with various $R^1$ and $R^2$ substituents. It is known in the art how to provide substituents on aromatic rings. For example, where it is desirable to provide substitution on one or both of the aromatic rings, electrophilic aromatic substitution can be used to provide desired functionality. For example, alkyl, aryl, heteroaryl, alkaryl, arylalkyl, alkenyl, alkynyl, and acyl groups can be added using Friedel-Crafts alkylation/arylation/acylation reactions. Other electrophilic aromatic substitution reactions can be used, for example, to provide halogens, such as by forming chloronium or bromonium ions in situ and reacting them with the aromatic ring, or by forming sulfonium or nitronium ions to provide sulfonyl or nitro groups.

Friedel Crafts alkylation is conducted using an appropriate halo-alkyl moiety, and a Lewis acid. The alkyl moiety forms a carbocation, and electrons from the aryl ring form a bond with the carbocation, placing a positive charge on the aryl ring. The aryl ring then loses a proton. Alkyl and alkaryl moieties (such as benzyl moieties) can be added in this fashion.

Friedel Crafts acylation is similar, but uses an acid halide, such as an acid chloride, to place a ketone moiety on the ring. The acid halide can be an alkyl acid, such as acetic acid, propionic acid, butyric acid, and the like, or can be an aromatic acid, such as benzoic acid, p-toluic acid, and the like.

Friedel Crafts arylation (also known as the Scholl reaction) is a coupling reaction with two aryl rings, catalyzed by a Lewis acid. The proton lost during the coupling reaction serves as an additional catalyst. Typical Reagents are iron (III) chloride in dichloromethane, copper(II) chloride, PIFA and boron trifluoride etherate in dichloromethane, Molybdenum(V) chloride and lead tetraacetate with $BF_3$ in acetonitrile.

Substitution typically occurs at a position ortho or para to the amine groups, and meta to nitro groups. Accordingly, depending on the desired functionality and position, it may be desirable to start with an amine group, and place a substituent So, positions 3, 6, and 8 are typically functionalized using this chemistry. Substitution of the naphthalene ring at a meta position to the amine groups (i.e., positions 2 and 7) can be performed by oxidizing the amine group(s) to nitro groups, which leads to meta substitution. The nitro groups can then be reduced back to the amine groups.

Incorporation of Deuterium:

It is expected that single or multiple replacement of hydrogen with deuterium (carbon-hydrogen bonds to carbon-deuterium bond) at site(s) of metabolism on ROR modulators will slow down the rate of metabolism. This can provide a relatively longer half-life, and slower clearance from the body. The slow metabolism of a therapeutic ROR modulators is expected to add extra advantage to a therapeutic candidate, while other physical or biochemical properties are not affected.

Methods for incorporating deuterium into organic derivatives are well known to those of skill in the art. Representative methods are disclosed in *Angew. Chem. Int. Ed. Engl.* 2007, 46, 7744-7765. Accordingly, using these techniques, one can provide one or more deuterium atoms in the ROR modulators described herein.

The present invention will be better understood with reference to the following non-limiting examples.

Example 1

Synthesis of Compound 1 and Compounds 34-46

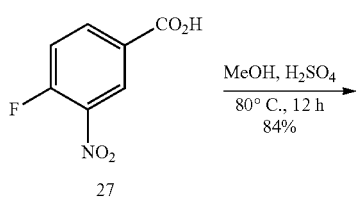

27

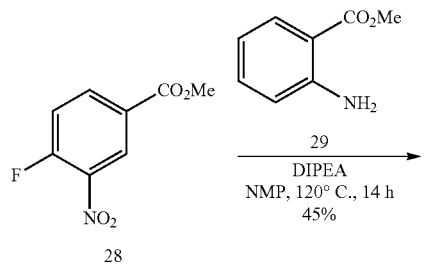

28

Methyl 4-fluoro-3-nitrobenzoate (28)

4-Fluoro-3-nitrobenzoic acid 27 (10 g, 54 mmol) was dissolved in methanol (200 mL) and conc. $H_2SO_4$ (1 mL) at room temperature. The reaction mixture was stirred overnight at 80° C. After completion of the reaction, the solvent was evaporated under reduced pressure. The crude mixture was diluted with $H_2O$ (200 ml) and basified with a saturated solution of $NaHCO_3$. The precipitated solid was filtered, washed with water (2×100 mL) and dried under vacuum to afford compound 28 as a white solid (10.75 g, 84%); $^1H$ NMR (400 MHz, DMSO-$d_6$): δ 8.54 (dd, J=7.3, 2.3 Hz, 1H), 8.31 (ddd, J=8.8, 4.3, 2.3 Hz, 1H), 7.73 (dd, J=11.1, 8.7 Hz, 1H), 3.90 (s, 3H); $^{13}C$ NMR (101 MHz, DMSO-$d_6$): 158.7, 156.0, 136.9, 136.8 (d, J=10.8 Hz), 127.1 (d, J=1.6 Hz), 126.7 (d, J=3.9 Hz), 119.4 (d, J=21.7 Hz), 52.9; $^{19}F$ NMR (377 MHz, DMSO) δ −111.97.

Methyl 4-((2-(methoxycarbonyl)phenyl)amino)-3-nitrobenzoate (30)

To a solution of methyl 4-fluoro-3-nitrobenzoate 28 (1 g, 6.61 mmol) in NMP (20 mL) were added DIPEA (0.76 ml, 19.83 mmol) and methyl 4-fluoro-3-nitrobenzoate 29 (1.5 g, 9.92 mmol) at room temperature, under inert atmosphere. The mixture was stirred at 120° C. for 14 h and after completion of the reaction, the mixture was cooled down to room temperature, diluted with diethyl ether (20 ml) and stirred for 1 h, The obtained solid was filtered, washed with EtOAc (20 mL) and dried under vacuum to afford compound 30 as a yellow solid (996 mg, 45%); $^1$H NMR (400 MHz, DMSO-$d_6$): δ 11.15 (s, 1H), 8.66 (d, J=2.1 Hz, 1H), 8.09-7.96 (m, 2H), 7.71-7.61 (m, 2H), 7.59 (d, J=9.0 Hz, 1H), 7.29 (ddd, J=8.2, 5.9, 2.1 Hz, 1H), 3.87 (s, 6H); $^{13}$C NMR (101 MHz, DMSO): δ 166.6, 164.5, 142.7, 139.7, 135.4, 134.7, 133.9, 131.5, 128.0, 124.2, 121.9, 120.4, 120.0, 117.8, 52.5, 52.3.

Methyl 3-amino-4-((2-(methoxycarbonyl)phenyl) amino)benzoate (31)

A solution of methyl 4-((2-(methoxycarbonyl)phenyl) amino)-3-nitrobenzoate 30 (2.5 g, 7.5 mmol) and 10% Pd/C (1.25 g, 50% wet) in MeOH was stirred under hydrogen atmosphere for 16 h at room temperature. After completion of the reaction, the mixture was filtered through Celite and washed with 20% MeOH/DCM (250 mL). The filtrate was concentrated and the crude residue was purified was purified by flash column chromatography (AcOEt/hexanes 3/7) to afford compound 31 as a yellow solid (1.4 g, 62%); $^1$H NMR (400 MHz, DMSO-$d_6$) δ 8.93 (s, 1H), 7.91 (d, J=8.4 Hz, 1H), 7.52-7.36 (m, 2H), 7.21 (s, 2H), 6.95 (d, J=8.4 Hz, 1H), 6.88-6.72 (m, 1H), 5.19 (s, 2H), 3.85 (s, 3H), 3.80 (s, 3H); $^{13}$C NMR (101 MHz, DMSO) δ 167.9, 166.3, 146.7, 142.2, 134.3, 131.2, 130.6, 125.5, 121.9, 118.1, 117.7, 116.2, 114.9, 112.3, 51.9, 51.8.

3-Amino-4-((2-carboxyphenyl)amino)benzoic acid (32)

To a solution of methyl 3-amino-4-((2-(methoxycarbonyl) phenyl)amino)benzoate 31 (1.4 g, 4.66 mmol) in a mixture of THF:$H_2O$ (2.5/1, 105 ml) was added lithium hydroxide monohydrate (1.75 g, 41.9 mmol) at room temperature. The reaction mixture was stirred at 65° C. for 5 h and the volatiles were removed under vacuum. The pH of the residue was acidified to 4 with 2N HCl. The precipitated solid was filtered, washed with water (10 ml) and dried under vacuum to afford compound 32 as a white solid (1 g, 80%). $^1$H NMR (400 MHz, DMSO-$d_6$) δ 12.64 (s, 2H), 9.20 (s, 1H), 7.89 (d, J=7.9 Hz, 1H), 7.44-7.31 (m, 2H), 7.18 (s, 2H), 6.91 (d, J=8.5 Hz, 1H), 6.76 (t, J=7.5 Hz, 1H), 5.06 (s, 2H); $^{13}$C NMR (101 MHz, DMSO) δ 169.8, 167.4, 147.3, 142.1, 134.0, 131.7, 130.4, 126.6, 121.9, 118.4, 117.3, 116.5, 114.5, 112.8.

11-oxo-10,11-Dihydro-5H-dibenzo[b,e][1,4]diazepine-8-carboxylic acid (33)

A solution of compound 32 (1 g, 3.67 mmol) and CDI (2.39 g, 14.6 mmol) in THF (40 mL) was stirred at room temperature for 24 h under inert atmosphere. After completion of the reaction, the volatiles were removed under vacuum. The pH of the residue was adjusted to 2 using 2N HCl. The precipitated solid was filtered, washed with pentane (10 mL) and dried under vacuum to afford compound 33 as a pale green solid (746 mg, 80%). $^1$H NMR (400 MHz, DMSO-$d_6$) 12.66 (s, 1H), 9.93 (s, 1H), 8.28 (s, 1H), 7.70 (dd, J=7.9, 1.7 Hz, 1H), 7.57-7.49 (m, 2H), 7.36 (td, J=7.9, 1.7 Hz, 1H), 7.02 (dd, J=17.0, 8.1 Hz, 2H), 6.91 (t, J=7.4 Hz, 1H); $^{13}$C NMR (101 MHz, DMSO) δ 167.4, 166.7, 148.8, 143.8, 133.5, 132.3, 129.2, 126.0, 125.0, 122.5, 122.2, 121.1, 119.4, 119.2, SM (IS): m/z: 255.4 [M+1]

General Procedure I

To a solution of compound 33 (100 mg, 0.393 mmol) in DMF (5 ml) were added EDCI, HCl (121 mg, 0.629 mmol), HOBt (85 mg, 6.29 mmol), amine (0.511 mmol) and DIPEA (205 ml, 0.117 mmol) at 0° C. under inert atmosphere. The reaction mixture was then stirred at room temperature for 16-24 h. After completion of the reaction, water was added. The crude solid was filtered and washed with water. The crude residue was purified by chromatography on silica gel (DCM/Methanol) to afford the desired compound.

8-(4-benzylpiperidine-1-carbonyl)-10,11a-dihydro-4aH-dibenzo[b,e][1,4]diazepin-11(5H)-one (Compound 1)

Compound 1 was prepared from 4-benzylpiperidine (91 ml, 0.511 mmol) following general procedure I. Column chromatography: DCM/Methanol (95:5); Light yellow solid (111 mg, 68%); $^1$H NMR (400 MHz, DMSO-$d_6$) δ 9.91 (s, 1H), 8.06 (s, 1H), 7.68 (d, J=7.8 Hz, 1H), 7.34 (t, J=7.8 Hz, 1H), 7.27 (t, J 7.8 Hz, 2H), 7.16 (d, J=7.8 Hz, 3H), 7.05-6.99 (m, 4H), 6.89 (d, J=7.8 Hz, 1H), 4.34 (s, 1H), 3.67 (s, 1H), 2.78 (s, 2H), 2.52 (s, 2H), 1.75 (s, 1H), 1.56 (s, 2H), 1.17-1.02 (m, 2H); $^{13}$C NMR (101 MHz, DMSO-$d_6$) δ 168.2, 167.6, 149.6, 140.7, 140.0, 133.4, 132.2, 130.6, 129.3, 129.0, 128.1, 125.8, 123.4, 122.5, 120.9, 120.0, 119.4, 119.1, 42.1, 37.5, 31.6; SM (IS): 412.5 m/z: [M+1]; HRMS (ESI) [M+H]$^+$ calcd for $C_{26}H_{26}N_3O_2$: 412.1947, found: 412.2018.

8-(4-phenylpiperazine-1-carbonyl)-5H-dibenzo[b,e][1,4]diazepin-11(10H)-one (34)

Compound 34 was prepared from 4-phenylpiperazine (77 ml, 0.511 mmol) following general procedure I. Column chromatography: DCM/Methanol (95:5); Beige solid (100 mg, 64%); $^1$H NMR (400 MHz, DMSO-$d_6$) δ 9.94 (s, 1H), 8.12 (s, 1H), 7.70 (d, J=7.7 Hz, 1H), 7.37 (t, J=7.6 Hz, 1H), 7.23 (t, J=7.9 Hz, 2H), 7.06 (d, J=2.6 Hz, 3H), 7.01 (d, J=8.0 Hz, 1H), 6.97-6.93 (m, 3H), 6.82 (t, J=7.2 Hz, 1H), 3.72-3.52 (m, 4H), 3.15 (s, 4H); $^{13}$C NMR (101 MHz, DMSO-$d_6$) δ 168.4, 167.6, 150.8, 149.5, 141.0, 133.4, 132.2, 129.8, 129.4, 129.0, 123.8, 122.4, 120.9, 120.4, 119.4, 119.4, 119.1, 115.9, 48.2; SM (IS): 399.5 m/z: [M+1]; HRMS (ESI) [M+H]$^+$ calcd for $C_{24}H_{23}N_4O_2$: 399.1810, found: 399.1812.

N-nonyl-11-oxo-10,11-dihydro-5H-dibenzo[b,e][1,4]diazepine-8-carboxamide (35)

Compound 35 was prepared from nonylamine (93 μl, 0.511 mmol) following general procedure I. The reaction mixture was quenched with water and extracted with ethyl acetate (3×5 mL). The combined organic layers were dried over magnesium sulfate and concentrated under reduced pressure and finally purified by column chromatography eluting with DCM/Methanol (99:1 to 95/5); yellow solid (70 mg, 47%); $^1$H NMR (400 MHz, DMSO-$d_6$) δ 9.91 (s, 1H), 8.24 (t, J=5.4 Hz, 1H), 8.13 (s, 1H), 7.69 (dd, J=7.9, 1.6 Hz, 1H), 7.47-7.39 (m, 2H), 7.39-7.32 (m, 1H), 7.00 (dd, J=7.9, 5.4 Hz, 2H), 6.91 (t, J=7.9 Hz, 1H), 3.20 (q, J=6.6 Hz, 2H), 1.49 (d, J=8.0 Hz, 2H), 1.30-1.22 (m, 12H), 0.85 (t, J=6.6 Hz, 3H); $^{13}$C NMR (101 MHz, DMSO-$d_6$) δ 167.5, 165.3, 149.4, 142.4, 133.4, 132.2, 129.5, 129.2, 123.2, 122.4, 121.0, 120.9, 119.1, 119.0, 31.3, 29.1, 29.0, 28.8, 28.7, 26.5, 22.1, 14.0; SM (IS): 380.2 m/z: [M+1]; HRMS (ESI) [M+H]$^+$ calcd for C$_{23}$H$_{30}$N$_3$O$_2$: 380.2327, found: 380.2332.

8-(4-benzylpiperazine-1-carbonyl)-5H-dibenzo[b,e][1,4]diazepin-11(10H)-one. (36)

Compound 36 was prepared from 1-benzylpiperazine (89 ml, 0.511 mmol) following general procedure I. Column chromatography: DCM/Methanol (99:1 to 95/5); yellow solid (42 mg, 26%); $^1$H NMR (400 MHz, DMSO-d$_6$) 9.92 (s, 1H), 8.09 (s, 1H), 7.69 (dd, J=7.9, 1.7 Hz, 1H), 7.40-7.27 (m, 5H), 7.25 (td, J=5.9, 2.5 Hz, 1H), 7.08-6.93 (m, 4H), 6.91 (t, J=7.9 Hz, 1H), 3.50 (s, 4H), 3.36 (s, 2H), 2.36 (s, 4H); $^{13}$C NMR (101 MHz, DMSO-d$_6$) 168.3, 167.6, 149.5, 141.0, 137.8, 133.4, 132.2, 130.0, 129.3, 128.9, 128.2, 127.0, 123.7, 122.4, 120.9, 120.3, 119.4, 119.1, 61.9, 52.6; SM (IS): 413.5 m/z: [M+1]; HRMS (ESI) [M+H]$^+$ calcd for C$_{25}$H$_{25}$N$_4$O$_2$:413.1899, found: 413.1970.

8-(4-(4-fluorobenzyl)piperidine-1-carbonyl)-5H-dibenzo[b,e][1,4]diazepin-11(10H)-on (37)

Compound 37 was prepared from 4-(4-fluorobenzyl)piperidine (99 mg, 0.511 mmol) following general procedure I. Column chromatography: DCM: MeOH (99/1 to 95/5); Yellow solid (74 mg, 43%); $^1$H NMR (400 MHz, DMSO-d$_6$) δ 9.92 (s, 1H), 8.07 (s, 1H), 7.69 (dd, J=8.0, 1.7 Hz, 1H), 7.36 (ddd, J=8.0, 7.2, 1.7 Hz, 1H), 7.24-7.19 (m, 2H), 7.13-7.07 (m, 2H), 7.04-6.95 (m, 4H), 6.91 (ddd, J=8.0, 7.2, 1.7 Hz, 1H), 4.36 (s, 1H), 3.68 (s, 1H), 2.86 (s, 2H), 2.52 (s, 2H), 1.75 (s, 1H), 1.56 (s, 2H), 1.11 (qd, J=12.3, 4.2 Hz, 2H). $^{13}$C NMR (101 MHz, DMSO-d$_6$): δ 133.4, 132.2, 130.7 (d, J=7.8 Hz), 123.4, 120.9, 120.0, 119.3, 119.1, 114.8 (d, J=20.9 Hz), 41.1, 37.5. $^{19}$F NMR (377 MHz, DMSO-d$_6$): δ −117.51 (s). SM (IS): 430.5 m/z: [M+1]; HRMS (ESI) [M+H]$^+$ calcd for C$_{26}$H$_{25}$FN$_3$O$_2$:430.1853, found: 430.1926.

8-(morpholine-4-carbonyl)-5,10-dihydro-11H-dibenzo[b,e][1,4]diazepin-11-one (38)

Compound 38 was prepared from morpholine (44 ml, 0.511 mmol) following general procedure I. After 16 h, the reaction was quenched with water and extracted with ethyl acetate (3×5 mL). The combined organic layers were dried over magnesium sulfate and concentrated under reduced pressure, purified by column chromatography eluting with DCM/Methanol (99:1 to 95/5); yellow solid (54 mg, 43%); $^1$H NMR (400 MHz, DMSO-d$_6$) δ 9.92 (s, 1H), 8.10 (s, 1H), 7.70 (dd, J=7.9, 1.6 Hz, 1H), 7.36 (ddd, J=8.6, 7.9, 1.7 Hz, 1H), 7.06-6.94 (m, 4H), 6.96-6.87 (m, 1H), 3.58 (d, J=5.0 Hz, 4H), 3.47 (s, 4H); $^{13}$C NMR (101 MHz, DMSO-d$_6$): δ 168.5, 167.6, 149.5, 141.1, 133.4, 132.2, 129.6, 129.4, 123.8, 122.4, 120.9, 120.5 119.4, 119.1, 66.2, 40.1. SM (IS): 324.5 m/z: [M+1]; HRMS (ESI) [M+H]$^+$ calcd for CH$_{18}$N$_3$O: 324.1270, found: 324.1341.

N-(3-(1H-imidazol-1-yl)propyl)-11-oxo-10,11-dihydro-5H-dibenzo[b,e][1,4]diazepine-8-carboxamide (39)

Compound 39 was prepared from 3-(1H-imidazol-1-yl)propan-1-amine (0.511 mmol) following general procedure I. After 16 h, 30 ml of water were added, and the mixture was extracted two times with 20 ml of ethyl acetate. The combined organic layers were dried with MgSO$_4$, filtered and evaporated under vacuum. The crude solid was purified by column chromatography eluting with DCM/Methanol (99:1 to 95/5); yellow solid (40 mg, 28%). $^1$H NMR (400 MHz, DMSO-d$_6$) δ 9.92 (s, 1H), 8.34 (t, J=5.6 Hz, 1H), 8.15 (s, 1H), 7.70 (dd, J=7.9, 1.7 Hz, 1H), 7.65 (d, J=1.3 Hz, 1H), 7.53-7.41 (m, 2H), 7.36 (ddd, J=8.7, 7.2, 1.7 Hz, 1H), 7.21 (d, J=1.3 Hz, 1H), 7.08-6.97 (m, 2H), 6.93-6.87 (m, 2H), 4.00 (t, J=6.9 Hz, 2H), 3.19 (q, J=6.9 Hz, 2H), 1.93 (p, J=6.9 Hz, 2H), 13C NMR (101 MHz, DMSO-d$_6$): δ 167.5, 165.7, 149.3, 142.5, 137.3, 133.4, 132.2, 129.3, 129.2, 128.4, 123.3, 122.4, 121.0, 121.0, 119.3, 119.1, 119.0, 43.7, 36.4, 30.8. SM (IS): 362.4 m/z: [M+1]; HRMS (ESI) [M+H]$^+$ calcd for C$_2$H$_{20}$NO$_2$:362.1539, found: 362.1609.

8-(4-(2-fluorobenzyl)piperidine-1-carbonyl)-5,10-dihydro-11H dibenzo[b,e][1,4]diazepin-11-one (40)

Compound 40 was prepared from 4-(2-fluorobenzyl)piperidine (99 mg, 0.511 mmol) following general procedure I. Column chromatography: DCM: MeOH (99/1 to 95/5); Yellow solid (135 mg, 80%); $^1$H NMR (400 MHz, DMSO-d$_6$): δ 9.92 (s, 1H), 8.08 (s, 1H), 7.70 (d, J=7.8 Hz, 1H), 7.36 (t, J=7.6 Hz, 1H), 7.27 (d, J=8.6 Hz, 2H), 7.14 (q, J=7.3 Hz, 2H), 7.00 (t, J=5.9 Hz, 4H), 6.92 (t, J=7.4 Hz, 1H), 4.35 (s, 1H), 3.69 (s, 1H), 2.75 (s, 2H), 2.58 (d, J=7.0 Hz, 2H), 1.79 (s, 1H), 1.58 (s, 2H), 1.15 (q, J=12.5 Hz, 2H); $^{13}$C NMR (101 MHz, DMSO-d$_6$) δ 168.3, 167.6, 161.8, 159.4, 149.6, 140.8, 133.4, 132.2, 131.7 (d, J=5.1 Hz), 130.6, 129.3, 128.1 (d, J=8.3 Hz), 126.6 (d, J=15.9 Hz), 124.2 (d, J=3.3 Hz), 123.4, 122.5, 120.9, 120.0, 119.4, 119.1, 115.1 (d, J=22.3 Hz), 36.6, 35.0, 31.7. $^{19}$F NMR (377 MHz, DMSO-d$_6$) δ −118.26, SM (IS): 430.1 m/z: [M+1]; HRMS (ESI) [M+H]$^+$ calcd for C$_{26}$H$_{24}$FN$_3$O$_2$:430.1853, found: 430.1927.

8-(piperidine-1-carbonyl)-5,10-dihydro-11H-dibenzo[b,e][1,4]diazepin-11-one (41)

Compound 41 was prepared from piperidine (58 ml, 0.511 mmol) following general procedure I. After 24 h, 30 ml of water were added, and the mixture was extracted two times with 20 ml of ethyl acetate. The combined organic layers were dried with MgSO$_4$, filtered and concentrated under vacuum. The crude solid was purified by column chromatography eluting with DCM/Methanol (99:1 to 95/5); yellow solid (20 mg, 16%); $^1$H NMR (400 MHz, DMSO-d$_6$) δ 9.92 (s, 1H), 8.07 (s, 1H), 7.69 (dd, J=7.9, 1.7 Hz, 1H), 7.40-7.33 (m, 1H), 7.05-6.96 (m, 4H), 6.95-6.88 (m, 1H), 3.42-3.31 (m, 4H), 1.60 (q, J=5.6 Hz, 2H), 1.54-1.41 (m, 4H). $^{13}$C NMR (101 MHz, DMSO) δ 168.2, 167.7, 149.6, 140.7, 133.4, 132.2, 130.7, 129.4, 123.4, 122.5, 120.9, 120.0, 119.4, 119.1, 25.7, 24.7; HRMS (ESI) [M+H]$^+$ calcd for C$_{19}$H$_2$O N$_3$O$_2$: 322.1477, found: 322.1548.

8-(4-phenylpiperidine-1-carbonyl)-5,10-dihydro-11H-dibenzo[b,e][1,4]diazepin-11-one (42)

Compound 42 was prepared from 4-phenylpiperidine (82 mg, 0.511 mmol) by following general procedure I. Colum chromatography: DCM: MeOH (99/1 to 95/5); yellow solid (67 mg, 43%); $^1$H NMR (400 MHz, DMSO-d$_6$) δ 9.94 (s, 1H), 8.09 (s, 1H), 7.70 (dd, J=7.9, 1.7 Hz, 1H), 7.38-7.32 (m, 1H), 7.32-7.26 (m, 4H), 7.21 (d, J=7.0 Hz, 1H), 7.08-7.02 (m, 3H), 7.00 (dd, J=8.1, 1.1 Hz, 1H), 6.94-6.88 (m, 1H), 4.71-4.39 (m, 1H), 3.95-3.66 (m, 1H), 3.11-2.98 (s, 1H), 2.80 (t, J=12.0 Hz, 2H), 1.98-1.73 (m, 2H), 1.61 (td, J=12.6, 4.1 Hz, 2H). SM (IS): 398.2 m/z: [M+1];

8-(4-phenethylpiperidine-1-carbonyl)-5, 10-dihydro-11H-dibenzo[b,e][1,4]diazepin-11-one (43)

Compound 43 was prepared from 4-phenethylpiperidine (96 mg, 0.511 mmol) by following general procedure I. Column chromatography: DCM/Methanol (99/1 to 95/5); yellow solid (67 mg, 40%); $^1$H NMR (400 MHz, DMSO-d$_6$) 9.92 (s, 1H), 8.07 (s, 1H), 7.69 (dd, J=7.9, 1.7 Hz, 1H), 7.36 (ddd, J=8.5, 7.9, 1.7 Hz, 1H), 7.28 (t, J=7.9 Hz, 2H), 7.23-7.14 (m, 3H), 7.03-6.97 (d, J=7.0 Hz, 4H), 6.95-6.89 (m, 1H), 4.38 (s, 1H), 3.69 (s, 1H), 2.90 (s, 2H), 2.60 (t, J=7.5 Hz, 3H), 1.73 (s, 2H), 1.52 (d, J=7.4 Hz, 3H), 1.22-0.99 (m, H). $^{13}$C NMR (101 MHz, DMSO-d$_6$) 168.6, 168.11, 150.0, 142.7, 141.2, 133.9, 132.6, 131.1, 129.8, 128.7, 128.7, 126.1, 123.8, 122.9, 121.4, 120.5, 119.8, 119.6, 4, 38.3, 35.4, 32.6. SM (IS): 426.2 m/z: [M+1].

N-(1-benzylpiperidin-4-yl)-11-oxo-10,11-dihydro-5H-dibenzo[b,e][1,4]diazepine-8-carboxamide (44)

Compound 44 was prepared from 1-benzyl-4-aminopiperidine (104 ml, 0.511 mmol) by following general procedure I. Column chromatography: DCM/Methanol (99/1 to 95/5); yellow solid (60 mg, 35%); $^1$H NMR (400 MHz, DMSO-d$_6$) 9.89 (s, 1H), 8.14 (s, 1H), 8.06 (d, J=7.6 Hz, 1H), 7.69 (dd, J=7.9, 1.6 Hz, 1H), 7.45 (d, J=7.0 Hz, 2H), 7.39-7.28 (m, 5H), 7.27-7.23 (m, 1H), 7.00 (t, J=7.9 Hz, 1H), 6.95-6.85 (m, 1H), 3.73 (d, J=7.0 Hz, 1H), 3.46 (s, 2H), 2.81 (d, J=9.8 Hz, 2H), 2.01 (s, 2H), 1.75 (d, J=12.4 Hz, 2H), 1.56 (td, J=11.8, 3.6 Hz, 2H); $^{13}$C NMR (101 MHz, DMSO-d$_6$): 168.0, 165.3, 149.8, 142.9, 139.1, 133.8, 132.7, 129.9, 129.6, 129.2, 128.6, 127.3, 123.9, 122.8, 121.5, 121.4, 119.6, 119.4, 62.6, 52.7, 47.3, 32.0. SM (IS): 427.3 m/z: [M+1].

8-(4-benzoylpiperidine-1-carbonyl)-5,10-dihydro-11H-dibenzo[b,e][1,4]diazepin-11-one (45)

Compound 45 was prepared from 4-benzoylpiperidine (89 ml, 0.511 mmol) by following general procedure I. Column chromatography: DCM/Methanol (99/1 to 95/5); yellow solid (114 mg, 68%); $^1$H NMR (400 MHz, DMSO-d$_6$) 9.93 (s, 1H), 8.09 (s, 1H), 8.01 (d, J=7.7 Hz, 2H), 7.74-7.61 (m, 2H), 7.55 (t, J=7.5 Hz, 2H), 7.42-7.31 (m, 1H), 7.02 (d, J=7.4 Hz, 4H), 6.91 (t, J=7.5 Hz, 1H), 4.40 (s, 1H), 3.86-3.65 (m, 1H), 3.08 (s, 4H), 1.82 (s, 2H), 1.52 (d, J=13.8 Hz, 3H), $^{13}$C NMR (101 MHz, DMSO-d$_6$): δ 201.7, 168.4, 167.6, 149.5, 140.8, 135.4, 133.4, 133.26, 132.2, 130.3, 129.3, 128.8, 128.2, 123.5, 122.4, 120.9, 120.0, 119.4, 119.1, 42.4, 28.5; SM (IS): 426.2 m/z: [M+1].

8-(4-(3-fluorobenzyl)piperidine-1-carbonyl)-5,10-dihydro-11H-dibenzo[b,e][1,4]diazepin-11-one (46)

Compound 46 was prepared following general procedure I with 4-(3-fluorobenzyl)piperidine hydrochloride (115 mg, 0.511 mmol). Column chromatography: DCM: MeOH (99/1 to 95/5); Yellow solid (90 mg, 53%); $^1$H NMR (400 MHz, DMSO-d$_6$) δ 9.92 (s, 1H), 8.07 (s, 1H), 7.69 (dd, J=7.9, 1.7 Hz, 1H), 7.38-7.27 (m, 2H), 7.03-6.96 (m, 7H), 6.93-6.88 (m, 1H), 4.35 (s, 1H), 3.73 (s, 1H), 2.78 (s, 2H), 2.54 (d, J=7.1 Hz, 2H), 1.87 (s, 1H), 1.55 (s, 2H), 1.11 (qd, J=12.1, 4.1 Hz, 2H), $^{19}$F NMR (377 MHz, DMSO-d$_6$) δ −113.89 (s), SM (IS): 430.1 m/z: [M+1];

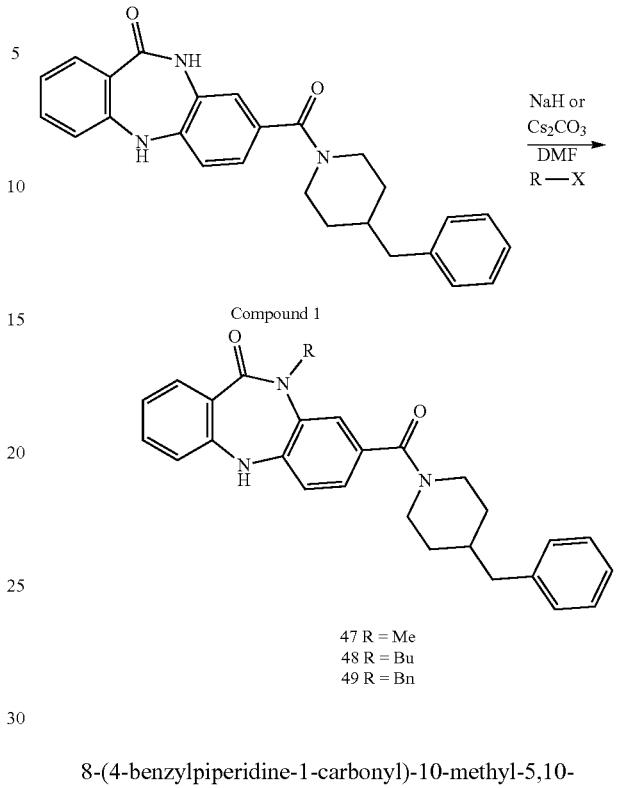

Scheme 11 Synthesis of compounds 47-49.

47 R = Me
48 R = Bu
49 R = Bn

8-(4-benzylpiperidine-1-carbonyl)-10-methyl-5,10-dihydro-11H dibenzo [b,e][1,4]diazepin-11-one (47)

Compound 1 (100 mg, 0.243 mmol) was dissolved in 1 ml of DMF, then Cs$_2$CO$_3$ (158 mg, 0.486 mg) was added at room temperature following by MeI (16 ml, 0.267 mmol). The reaction mixture was stirred overnight at room temperature and then diluted with H$_2$O (20 ml). The obtained solid was filtered, washed with 5 ml of H$_2$O and then purified by column chromatography on silica gel (DCM/Methanol (99:1)) to afford compound 47 as a white solid (80 mg, 78%). $^1$H NMR (400 MHz, DMSO-d$_6$) δ 8.13 (s, 1H), 7.67 (dd, J=7.9, 1.7 Hz, 1H), 7.40-7.33 (m, 1H), 7.32-7.25 (m, 3H), 7.20-7.12 (m, 4H), 7.12-7.06 (m, 2H), 7.00-6.95 (m, 1H), 4.50-4.27 (m, 1H), 3.80-3.56 (m, 1H), 3.61 (s, 3H), 3.10-2.82 (m, 1H), 2.72-2.70 (m, 1H), 2.53 (s, 2H), 1.80-1.74 (m, 1H), 1.67-1.47 (m, 2H), 1.25-1.02 (m, 2H); $^{13}$C NMR (101 MHz, DMSO) δ 168.1, 167.5, 151.2, 144.8, 140.0, 134.6, 132.6, 132.3, 131.5, 129.0, 128.2, 125.8, 124.3, 123.8, 122.0, 121.5, 119.9, 118.8, 42.1, 40.15, 37.7, 37.5, 31.5. SM (IS): 426.2 m/z: [M+1]; HRMS (ESI) [M+H]$^+$ calcd for C$_{27}$H$_{28}$N$_3$O$_2$:426.2103, found: 426.2176.

8-(4-benzylpiperidine-1-carbonyl)-10-butyl-5,10-dihydro-11H-dibenzo[b,e][1,4]diazepin-11-one (48)

Compound 1 (40 mg, 0.097 mmol) was dissolved in 0.5 ml of DMF, then NaH (5 mg, 0.194 mmol) was added at room temperature following by BuI (12 ml, 0.106 mmol). The reaction mixture was stirred overnight at room temperature. The mixture was diluted with H$_2$O (20 ml). The obtained solid was filtered, washed with 5 ml of H$_2$O and purified by column chromatography on silica gel (DCM/Methanol (99:1)) to afford compound 48 as a white solid (22.5 mg, 50%); $^1$H NMR (400 MHz, DMSO-d$_6$) δ 8.09 (s, 1H), 7.68 (dd, J=7.8, 1.7 Hz, 1H), 7.43-7.37 (m, 2H), 7.37-7.31 (m, 2H), 7.24 (ddd, J=8.3, 5.9, 1.9 Hz, 4H), 7.14 (ddd, J=16.2, 8.2, 1.5 Hz, 2H), 7.03 (ddd, J=8.1, 7.3, 1.2 Hz, 1H), 4.57-4.36 (m, 1H), 4.08 (s, 2H), 3.80-3.56 (m, 1H) 3.10-2.86 (m, 2H), 2.59 (s, 2H), 1.88-1.77 (m, 1H), 1.72-1.55 (m, 2H), 1.50 (dt, J=14.2, 6.8 Hz, 2H), 1.32 (dq, J=14.2, 7.3 Hz, 2H), 1.26-1.15 (m, 2H), 0.86 (t, J=7.3 Hz, 3H). SM (IS): 468.1 m/z: [M+1].

10-benzyl-8-(4-benzylpiperidine-1-carbonyl)-5,10-dihydro-11H-dibenzo[b,e][1,4]diazepin-11-one (49)

Compound 1 (40 mg, 0.097 mmol) was dissolved in 0.5 ml of DMF, then $Cs_2CO_3$ (63 mg, 0.191 mmol) was added at room temperature followed by benzylbromide (13 ml, 0.106 mmol). The reaction mixture was stirred overnight at room temperature and then diluted with $H_2O$ (20 ml). The obtained solid was filtered, washed with 5 ml of $H_2O$ and purified by column chromatography on silica gel (DCM/Methanol (99:1)) to afford compound 49 as a white solid (38 mg, 80%); $^1H$ NMR (400 MHz, DMSO-$d_6$) δ 8.13 (s, 1H), 7.69 (dd, J=7.8, 1.5 Hz, 1H), 7.39 (ddd, J=8.5, 7.3, 1.6 Hz, 1H), 7.35-7.24 (m, 7H), 7.22-7.13 (m, 4H), 7.16-7.07 (m, 2H), 7.05-6.96 (m, 2H), 5.27 (s, 2H), 4.54-4.06 (m, 1H), 2.94-2.50 (m, 1H), 2.48 (d, J=6.7 Hz, 1H), 1.77-1.65 (m, 1H), 1.61-1.38 (m, 2H), 1.27-1.23 (m, 1H), 1.04-0.97 (m, 1H), 0.90-0.84 (m, 1H). SM (IS): 502.6 m/z: [M+1].

Synthesis of Compounds 51 and 52

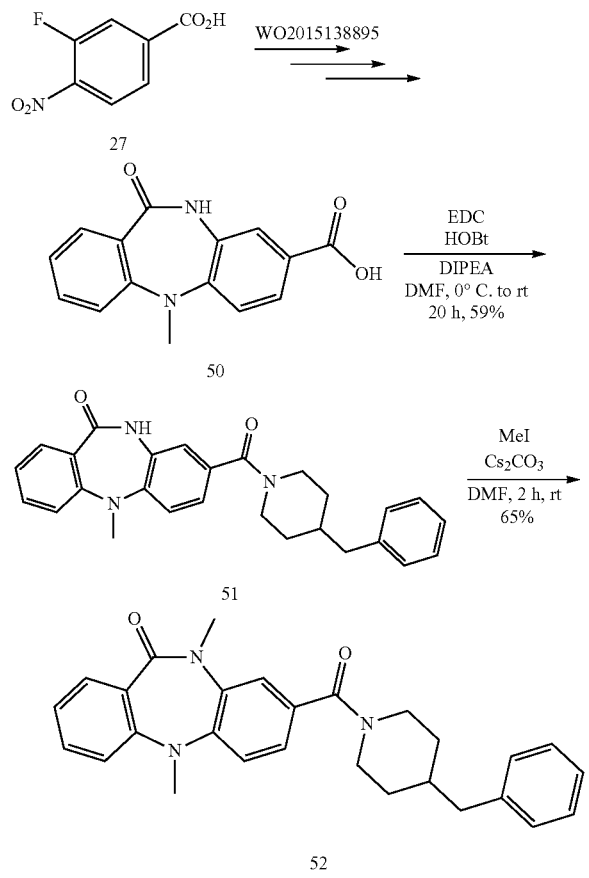

8-(4-benzylpiperidine-1-carbonyl)-5-methyl-5,10-dihydro-11H-dibenzo[b,e][1,4]diazepin-11-one (51)

Compound 51 was prepared from compound 50 (120 mg, 0.447 mmol, WO2015138895) and 4-benzylpiperidine (104 ml, 0.581 mmol) following general procedure I. Column chromatography: DCM/Methanol (99:1); white solid (113 mg, 59%); $^1H$ NMR (400 MHz, DMSO-$d_6$) δ 10.30 (s, 1H), 7.64 (dd, J=7.7, 2.0 Hz, 1H), 7.50 (ddd, J=8.2, 7.3, 1.8 Hz, 1H), 7.27 (dd, J=8.3, 6.5 Hz, 2H), 7.24-7.14 (m, 5H), 7.13-7.07 (m, 2H), 7.04 (d, J=2.0 Hz, 1H), 4.45-4.40 (m, 1H), 3.66-3.6 (m, 1H), 3.28 (s, 3H), 2.99-2.82 (m, 1H), 2.76-2.63 (m, 2H), 2.52 (s, 1H), 1.82-1.71 (m, 1H), 1.69-1.45 (m, 2H), 1.20-1.03 (m, 2H); $^{13}C$ NMR (101 MHz, DMSO-$d_6$) δ: 168.2, 168.0, 152.4, 145.0, 140.0, 132.9, 132.1, 131.7, 131.0, 129.0, 128.1, 126.7, 125.8, 123.3, 122.8, 119.8, 119.0, 117.7, 42.1, 40.15, 39.94, 37.8, 37.5, 31.9; SM (IS): 426.1 m/z: [M+1];

8-(4-benzylpiperidine-1-carbonyl)-5,10-dimethyl-5,10-dihydro-11H-dibenzo[b,e][1,4]diazepin-11-one (52)

Compound 51 (50 mg, 0.117 mmol) was dissolved in 1 ml of DMF, then $Cs_2CO_3$ (76 mg, 0.235 mg) was added at room temperature followed by MeI (14 ml, 0.235 mmol). The reaction mixture was stirred at room temperature for 2 h and then diluted with $H_2O$ (20 ml). The obtained solid was filtered, washed with 5 ml of $H_2O$ and purified by column chromatography on silica gel (DCM/Methanol (99:1)) to afford compound 52 as a white solid (33 mg, 65%); $^1H$ NMR (400 MHz, DMSO-$d_6$) δ 7.62 (dd, J=7.7, 1.7 Hz, 1H), 7.46 (ddd, J=8.7, 7.7, 1.9 Hz, 1H), 7.33 (d, J=1.9 Hz, 1H), 7.31-7.24 (m, 3H), 7.20-7.14 (m, 5H), 7.09 (td, J=7.5, 1.0 Hz, 1H), 4.53-4.23 (m, 1H), 3.60-3.57 (m, 1H), 3.43 (s, 3H), 3.35 (s, 3H), 2.99-2.93 (m, 1H), 2.72-2.63 (m, 1H), 2.52 (s, 2H), 1.85-1.69 (m, 1H), 1.68-1.43 (m, 2H), 1.20-1.05 (m, 2H); $^{13}C$ NMR (101 MHz, DMSO) δ 167.8, 167.5, 153.0, 147.9, 140.0, 136.5, 132.4, 131.5, 129.0, 128.1, 126.6, 125.8, 124.2, 122.8, 121.7, 118.7, 116.6, 42.0, 37.4, 37.4, 37.0, 31.9; SM (IS): m/z: 440.5 [M+1];

Synthesis of Compound 58

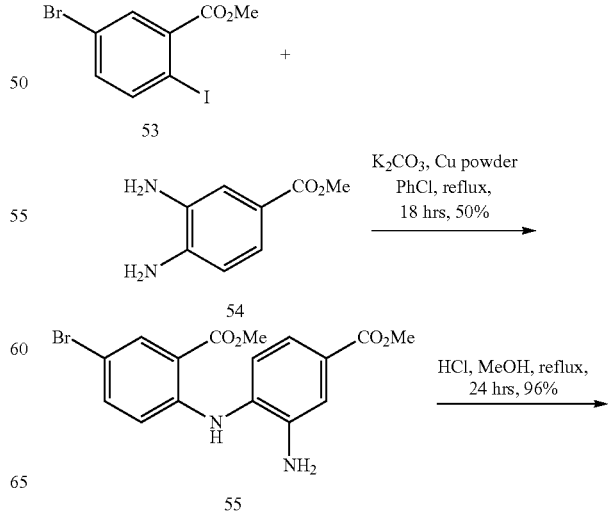

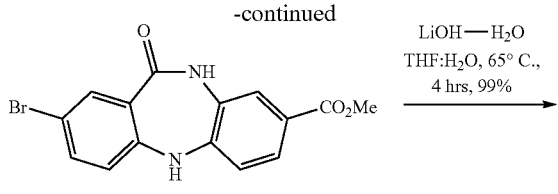

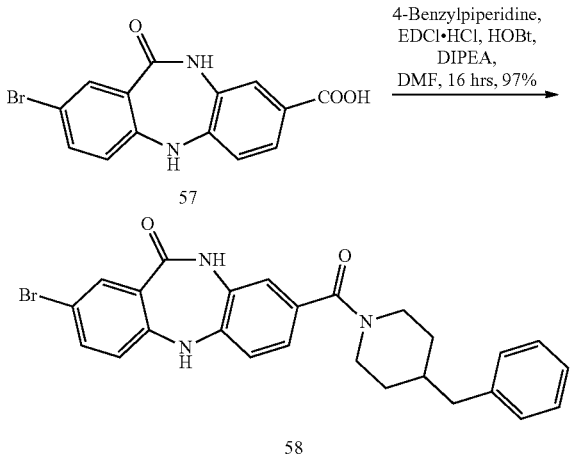

Methyl 2-((2-amino-4-(methoxycarbonyl)phenyl)amino)-5-bromobenzoate (55)

To a solution of methyl-3,4-diaminobenzoate 54 (2.051 g, 6.01 mmol) in chlorobenzene (20 mL) was added methyl 5-bromo-2-iodobenzoate 53 (1 g, 6.01 mmol), K$_2$CO$_3$ (0.87 g, 6.30 mmol), and Cu (0.382 g, 6.01 mmol). The resulting mixture was heated at reflux for 18 hours. While hot, the mixture was filtered through a thin layer of diatomaceous earth and the cake was washed with dichloromethane. The filtrate was concentrated and the crude product purified by flash chromatography on silica gel, eluting with 10%-100% CH$_2$Cl$_{12}$/hexanes gradient to yield title compound 55 (1.1 g, 50%). $^1$H NMR (400 MHz, Chloroform-d) δ 9.14 (bs, 1H), 8.09 (d, J=2.4 Hz, 1H), 7.49 (s, 1H), 7.43 (d, J=8.2 Hz, 1H), 7.38 (dd, J=9.0, 2.5 Hz, 1H), 7.21 (d, J=8.2 Hz, 1H), 6.72 (d, J=9.0 Hz, 1H), 3.93 (s, 3H), 3.90 (s, 3H). LR-MS calculated for C$_{16}$H$_{15}$BrN$_2$O$_4$ 378.02, found 379.3, 381.3.

Methyl 2-bromo-11-oxo-10,11-dihydro-5H-dibenzo[b,e][1,4]diazepine-8-carboxylate (56)

To compound 55 (0.72 g, 1.9 mmol) in methanol (35 mL) was added concentrated HCl (7 mL) and the mixture was heated to reflux overnight. After cooling to room temperature, the reaction mixture was filtered and the cake was washed with water to yield title compound 56 (0.63 g, 96%). $^1$H NMR (400 MHz, DMSO-d$_6$) δ 10.09 (s, 1H), 8.52 (s, 1H), 7.78 (d, J=2.5 Hz, 1H), 7.59-7.52 (m, 3H), 7.05 (d, J=8.2 Hz, 1H), 6.96 (d, J=8.6 Hz, 1H), 3.80 (s, 3H). LR-MS calculated for C$_{15}$H$_{11}$BrN$_2$O$_3$ 345.99, found 347.0, 349.0.

2-Bromo-11-oxo-10,11-dihydro-5H-dibenzo[b,e][1,4]diazepine-8-carboxylic acid (57)

To a stirred solution of compound 4 (0.6 g, 1.7 mmol) in THF:H$_2$O (7:3, 45 mL) was added lithium hydroxide monohydrate (0.435 g, 10.4 mmol) at room temperature. The resulting solution was stirred at 65° C. for 4 h. The reaction was monitored by TLC and after completion of reaction, the volatiles were removed in vacuo. The pH of the residue was acidified to a pH of ~4 with 2N HCl. The precipitated solid was filtered, washed with water (20 mL) and dried in vacuo to afford compound 5 (0.570 g, 99%). $^1$H NMR (400 MHz, DMSO-d$_6$) δ 12.65 (s, 1H), 10.00 (s, 1H), 8.62 (s, 1H), 7.70 (d, J=2.5 Hz, 1H), 7.50-7.43 (m, 3H), 7.04 (d, J=8.3 Hz, 1H), 6.99 (d, J=8.7 Hz, 1H). LR-MS calculated for C$_{19}$H$_9$BrN$_2$O$_3$ 331.97, found 333.3, 335.3.

8-(4-Benzylpiperidine-1-carbonyl)-2-bromo-5,10-dihydro-11H-dibenzo[b,e][1,4]diazepin-11-one (58)

To a solution of compound 57 (0.3 g, 0.90 mmol) in 5 ml DMF was added N-(3-dimethylaminopropyl)-N'-ethylcarbodiimide hydrochloride (EDCI) (0.276 g, 1.44 mmol), N-hydroxybenzotriazole (HOBt) (0.194 g, 1.44 mmol), 4-benzylpiperidine (0.205 mL, 1.17 mmol) followed by DIPEA (0.470 mL, 2.70 mmol). The reaction mixture was stirred at room temperature for 16 hours, quenched with water and then extracted with ethyl acetate. The combined organic layers were washed with brine, dried over sodium sulfate and concentrated under vacuum. The residue was then suspended in 3 mL of ethyl acetate before addition of 30 mL of hexanes. The precipitate was filtered and washed with hexane (10 mL) to afford title compound 58 (0.430 g, 97%). $^1$H NMR (400 MHz, Methanol-d$_4$) δ 7.85 (d, J=2.4 Hz, 1H), 7.44 (dd, J=8.6, 2.5 Hz, 1H), 7.28-7.23 (m, 2H), 7.18-7.14 (m, 3H), 7.06-6.97 (m, 3H), 6.85 (d, J=8.6 Hz, 1H), 4.63-4.44 (m, 1H), 3.88-3.63 (m, 1H), 3.11-2.92 (m, 1H), 2.91-2.08 (m, 1H), 2.86-2.69 (m, 1H), 2.56 (d, J=5.7 Hz, 2H), 1.91-1.54 (m, 3H), 1.29-1.11 (m, 2H). LR-MS calculated for C$_{26}$H$_{24}$BrN$_3$O$_2$ 489.10, found 490.0, 491.9.

Synthesis of Compound 59

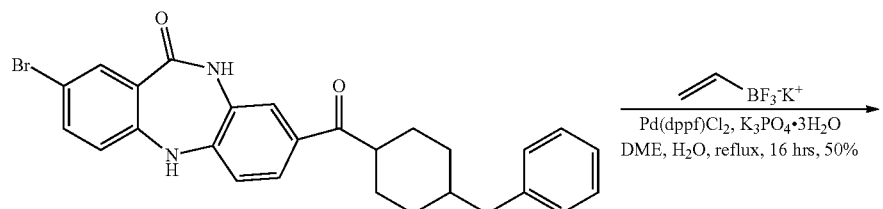

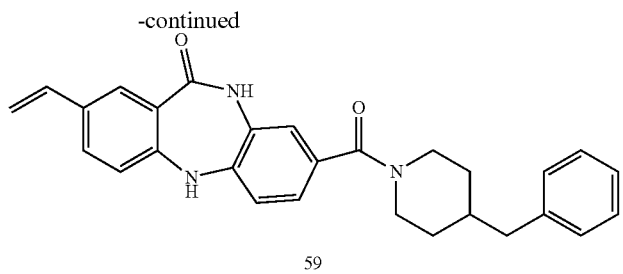

59

8-(4-benzylpiperidine-1-carbonyl)-2-vinyl-5,10-dihydro-11H-dibenzo[b,e][1,4]diazepin-11-one (59)

A mixture of compound 58 (0.1 g, 0.204 mmol) and potassium vinyltrifluoroborate (36 mg, 0.265 mmol), [1,1'-bis(diphenylphosphino)ferrocene] dichloropalladium (II) (0.030, 0.04 mmol) and K₃PO₄·3H₂O (0.143 g, 0.674 mmol) in DME:H₂O (2:1, 4 mL) was heated to reflux for 16 hours. After cooling the reaction mixture was partitioned between ethyl acetate and water. The ethyl acetate layer was washed with brine, dried over magnesium sulfate, filtered and concentrated. The residue was purified by flash column chromatography on silica gel using CH₂Cl₂:MeOH to provide title compound 59 (50 mg, 50%). ¹H NMR (400 MHz, Methanol-d₄) δ 7.82 (d, J=2.2 Hz, 1H), 7.47 (dd, J=8.4, 2.2 Hz, 1H), 7.29-7.24 (m, 2H), 7.19-7.15 (m, 3H), 7.06-6.98 (m, 3H), 6.91 (d, J=8.4 Hz, 1H), 6.65 (dd, J=17.6, 11.0 Hz, 1H), 5.68 (dd, J=17.6, 0.9 Hz, 1H), 5.16 (dd, J=10.9, 0.9 Hz, 1H), 4.62-4.45 (m, 1H), 3.85-3.70 (m, 1H), 3.12-2.94 (m, 1H), 2.86-2.69 (m, 1H), 2.58 (d, J=7.1 Hz, 2H), 1.88-1.55 (m, 3H), 1.29-1.11 (m, 2H). LR-MS calculated for C₂₈H₂₇N₃O₂ 437.21, found 438.5.

Synthesis of Compounds 60-66

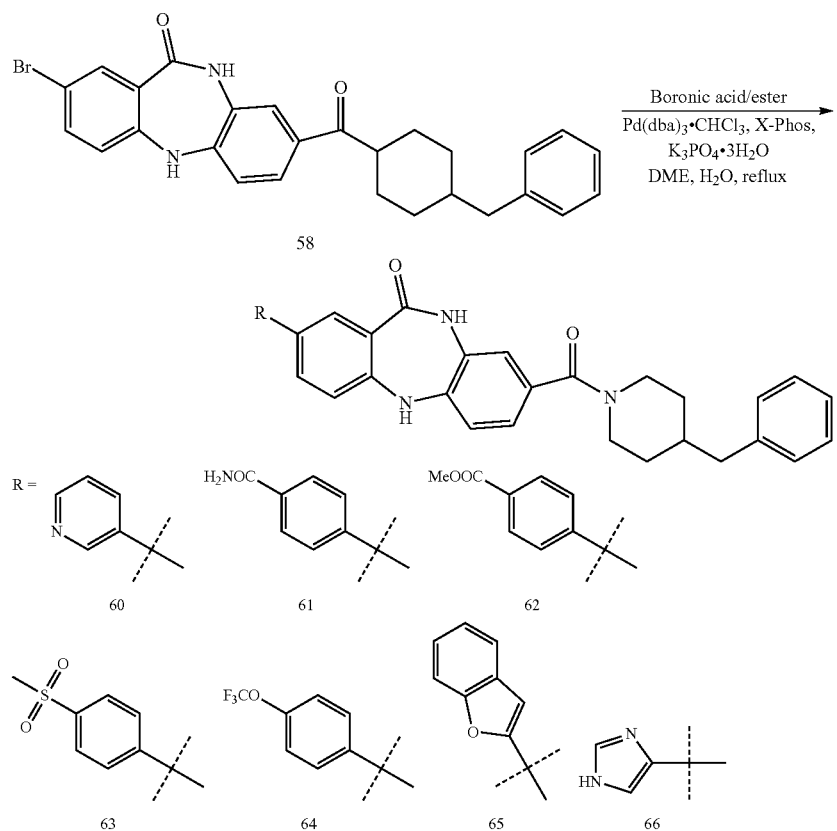

8-(4-benzylpiperidine-1-carbonyl)-2-(pyridin-3-yl)-5,10-dihydro-11H-dibenzo[b,e][1,4]diazepin-11-one (60)

A mixture of compound 58 (0.025 g, 0.051 mmol) and 3-pyridineboronic acid 1,3-propanediol ester (0.013, 0.076 mmol), Pd₂(dba)₃ CHCl₃ (5.2 mg, 0.005 mmol), X-Phos (14.6 mg, 0.030 mmol) and K₃PO₄·3H₂O (0.035 g, 0.168 mmol) in DME:H₂O (2:1.4 mL) was heated to reflux for 48 hours. After cooling the reaction was partitioned between ethyl acetate and water. The ethyl acetate layer was washed with brine, dried on magnesium sulfate, filtered and concentrated. The residue was purified by flash column chromatography on silica gel using $CH_2Cl_2$:MeOH to provide title compound 59 (19 mg, 78%). $^1$H NMR (400 MHz, DMSO-$d_6$) δ 10.04 (s, 1H), 8.83 (d, J=2.6 Hz, 1H), 8.53 (dd, J=4.8, 1.6 Hz, 1H), 8.32 (s, 1H), 8.03-7.99 (m, 2H), 7.76 (dd, J=8.4, 2.4 Hz, 1H), 7.48-7.44 (m, 1H), 7.30-7.27 (m, 2H), 7.20-7.12 (m, 4H), 7.05-6.99 (m, 3H), 4.50-4.18 (m, 1H), 3.85-3.50 (m, 1H), 3.05-2.58 (m, 2H), 2.53 (d, J=7.7 Hz, 2H), 1.84-1.71 (m, 1H), 1.70-1.41 (m, 2H), 1.18-1.06 (m, 2H). LR-MS calculated for $C_{31}H_{28}N_4O_2$ 488.22, found 489.2.

4-(8-(4-benzylpiperidine-1-carbonyl)-11-oxo-10,11-dihydro-5H-dibenzo[b,e][1,4]diazepin-2-yl)benzamide (61)

Compound 61 was synthesized by following the chemistry used to prepare compound 60 by substituting 4-aminocarbonylphenylboronic acid for 3-pyridineboronic acid 1,3-propanediol ester (63% yield). $^1$H NMR (400 MHz, DMSO-$d_6$) δ 10.03 (s, 1H), 8.31 (s, 1H), 8.09-7.91 (m, 4H), 7.77 (dd, J=8.5, 2.4 Hz, 1H), 7.69 (d, J=8.5 Hz, 2H), 7.38 (s, 1H), 7.32-7.25 (m, 2H), 7.22-7.09 (m, 4H), 7.07-6.97 (m, 3H), 4.58-4.14 (m, 1H), 3.85-3.54 (m, 1H), 3.05-2.53 (m, 4H), 1.87-1.69 (m, 1H), 1.68-1.43 (s, 2H), 1.19-1.06 (m, 2H). LR-MS calculated for $C_{33}H_{30}N_4O_3$ 530.23, found 531.2.

Methyl 4-(8-(4-benzylpiperidine-1-carbonyl)-11-oxo-10,11-dihydro-5H-dibenzo[b,e][1,4]diazepin-2-yl)benzoate (62)

Compound 62 was synthesized by following the chemistry used to prepare compound 60 by substituting for 4-methoxycarbonylphenylboronic acid for 3-pyridineboronic acid 1,3-propanediol ester (23% yield). $^1$H NMR (400 MHz, DMSO-$d_6$) δ 10.04 (s, 1H), 8.36 (s, 1H), 8.15-7.95 (m, 3H), 7.88-7.71 (m, 3H), 7.41-7.22 (m, 2H), 7.23-7.09 (m, 4H), 7.07-6.97 (m, 3H), 4.54-4.17 (m, 1H), 3.87 (s, 3H), 3.79-3.52 (m, 1H), 3.08-2.54 (m, 4H), 1.84-1.71 (m, 1H), 1.67-1.45 (m, 2H), 1.18-1.03 (m, 2H). LR-MS calculated for $C_{34}H_{31}N_3O_4$ 545.23, found 546.0.

8-(4-benzylpiperidine-1-carbonyl)-2-(4-(methylsulfonyl)phenyl)-5,10-dihydro-11H-dibenzo[b,e][1,4]diazepin-11-one (63)

Compound 63 was synthesized by following the chemistry used to prepare compound 60 by substituting 4-(methanesulfonyl)phenylboronic acid for 3-pyridineboronic acid 1,3-propanediol ester (85% yield). $^1$H NMR (400 MHz, DMSO-$d_6$) δ 10.05 (d, J=2.1 Hz, 1H), 8.38 (s, 1H), 8.07 (d, J=2.4 Hz, 1H), 7.99-7.94 (m, 2H), 7.92-7.86 (m, 2H), 7.79 (dd, J=8.5, 2.4 Hz, 1H), 7.33-7.24 (m, 2H), 7.21-7.11 (m, 4H), 7.06-6.97 (m, 3H), 4.55-4.16 (m, 1H), 3.75-3.53 (m, 1H), 3.24 (s, 3H), 3.05-2.53 (m, 4H), 1.83-1.68 (m, 1H), 1.67-1.45 (m, 2H), 1.18-1.03 (m, 2H). LR-MS calculated for $C_{33}H_{31}N_3O_4S$ 565.20, found 566.1.

8-(4-benzylpiperidine-1-carbonyl)-2-(4-(trifluoromethoxy)phenyl)-5,10-dihydro-11H-dibenzo[b,e][1,4]diazepin-11-one (64)

Compound 12 was synthesized by following the chemistry used to prepare compound 60 by substituting 4-(trifluoromethoxy)phenylboronic acid for 3-pyridineboronic acid 1,3-propanediol ester (63% yield). $^1$H NMR (400 MHz, DMSO-$d_6$) δ 10.04 (s, 1H), 8.30 (s, 1H), 7.98 (d, J=2.4 Hz, 1H), 7.75-7.64 (m, 3H), 7.49-7.35 (m, 2H), 7.27 (dd, J=8.3, 6.4 Hz, 2H), 7.21-7.08 (m, 4H), 7.08-6.93 (m, 3H), 4.58-4.17 (m, 1H), 3.83-3.48 (m, 1H), 3.07-2.53 (m, 4H), 1.83-1.68 (m, 1H), 1.67-1.40 (m, 2H), 1.17-1.05 (m, 2H). LR-MS calculated for $C_{33}H_{28}F_3N_3O_3$ 571.20, found 572.2.

2-(benzofuran-2-yl)-8-(4-benzylpiperidine-1-carbonyl)-5,10-dihydro-11H-dibenzo[b,e][1,4]diazepin-11-one (65)

Compound 65 was synthesized by following the chemistry used to prepare compound 60 by substituting 2-benzofuranylboronic acid for 3-pyridineboronic acid 1,3-propanediol ester (52% yield). $^1$H NMR (400 MHz, DMSO-$d_6$) δ 10.07 (s, 1H), 8.44 (s, 1H), 8.25 (d, J=2.2 Hz, 1H), 7.91 (dd, J=8.4, 2.3 Hz, 1H), 7.65-7.56 (m, 2H), 7.38-7.22 (m, 5H), 7.22-7.09 (m, 4H), 7.07-6.94 (m, 3H), 4.61-4.11 (m, 1H), 3.87-3.51 (m, 1H), 3.05-2.53 (m, 4H), 1.84-1.69 (m, 1H), 1.68-1.44 (m, 2H), 1.26-1.00 (m, 2H). LR-MS calculated for $C_{34}H_{29}N_3O_3$ 527.22, found 528.2.

8-(4-benzylpiperidine-1-carbonyl)-2-(1H-pyrazol-4-yl)-5,10-dihydro-11H-dibenzo[b,e][1,4]diazepin-11-one (66)

Compound 66 was synthesized by following the chemistry used to prepare compound 60 by substituting 1H-pyrazole-4-boronic acid for 3-pyridineboronic acid 1,3-propanediol ester (62% yield). $^1$H NMR (400 MHz, DMSO-$d_6$) δ 12.90 (s, 1H), 9.98 (s, 1H), 8.06 (s, 2H), 7.87 (d, J=2.3 Hz, 2H), 7.61 (dd, J=8.3, 2.3 Hz, 1H), 7.31-7.25 (m, 2H), 7.21-7.15 (m, 3H), 7.05-6.96 (m, 4H), 4.68-4.17 (m, 1H), 3.89-3.51 (m, 1H), 3.03-2.53 (m, 4H), 1.87-1.70 (m, 1H), 1.67-1.37 (m, 2H), 1.20-1.01 (m, 2H). LR-MS calculated for $C_{29}H_{27}N_5O_2$ 477.21, found 478.2.

Synthesis of compound 67

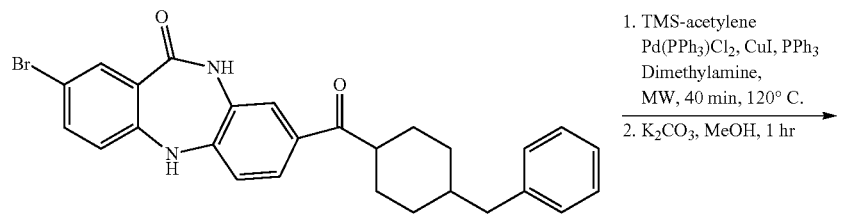

-continued

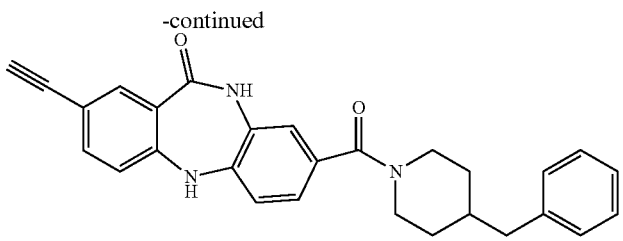

67

8-(4-benzylpiperidine-1-carbonyl)-2-ethynyl-5,10-dihydro-11H-dibenzo[b,e][1,4]diazepin-11-one (67)

A mixture of compound 58 (0.100 g, 0.204 mmol), Pd(PPh$_3$)Cl$_2$ (7.1 mg, 0.01 mmol), CuI (1.9 mg, 0.01 mmol), triphenylphosphine (10.7 mg, 0.04 mmol), trimethylsilylacetylene (31 μL, 0.224 mmol), and diethylamine (0.29 mL, 2.76 mmol) in dimethylformamide (1 mL) was heated at 120° C. for 40 min under microwave irradiation. The reaction mixture was filtered and washed with dichloromethane. The filtrate was concentrated under reduced pressure and the residue was purified by flash chromatography on silica gel to obtain 63 mg of trimethylsilyl protected intermediate. This intermediate was then treated with potassium carbonate (68 mg, 4 mmol) in methanol (3 mL) and the reaction mixture stirred at room temperature for 1 h. The reaction mixture was filtered, and the filtrate was concentrated under reduced pressure to give a residue, which was purified by flash chromatography on silica gel to give title compound 67 (46 mg, 53% over two steps). $^1$H NMR (400 MHz, DMSO-d$_6$) δ 9.99 (s, 1H), 8.39 (s, 1H), 7.75 (d, J=2.1 Hz, 1H), 7.42 (dd, J=8.3, 2.2 Hz, 1H), 7.33-7.23 (m, 2H), 7.21-7.09 (m, 3H), 7.04-6.65 (m, 4H), 4.50-4.17 (m, 1H), 4.07 (s, 1H), 3.83-3.48 (m, 1H), 3.08-2.53 (m, 4H), 1.87-1.68 (m, 1H), 1.67-1.43 (m, 2H), 1.19-1.01 (m, 2H). LR-MS calculated for C$_{28}$H$_{25}$N$_3$O$_2$ 435.19, found 436.3.

Example 2

Cellular Toxicity Assays

The toxicity of the compounds was assessed in human PBM, CEM (human lymphoblastoid), and Huh-7 cells, as described previously (see Schinazi R. F., Sommadossi J.-P., Saalmann V., Cannon D. L., Xie M.-Y., Hart G. C., Smith G. A. & Hahn E. F. *Antimicrob. Agents Chemother.* 1990, 34, 1061-67). Cycloheximide was included as positive cytotoxic control, and untreated cells exposed to solvent were included as negative controls. The cytotoxicity IC$_{50}$ was obtained from the concentration-response curve using the median effective method described previously (see Chou T.-C. & Talalay P. *Adv. Enzyme Regul.* 1984, 22, 27-55; Belen'kii M. S. & Schinazi R. F. Antiviral Res. 1994, 25, 1-11). The results are shown in Table 8 below:

TABLE 1

| | Cytotoxicity (IC$_{50}$, μM) | | |
| Structure | PBM | CEM | Huh-7 |
| --- | --- | --- | --- |
| Compound 1 | 92.4 | 11.0 | 10.4 |

Example 3

RORα Activity by Luciferase Reporter

Huh-7 cells were transfected with a luciferase reporter plasmid containing the miR-122 promoter (extends to −900 from the transcription start site) with intact wild-type (WT) RORα response element (RORE) or mutated RORE (mut). The cells were treated with Compound 1 one day (24 hours) post-transfection at the indicated concentrations. Luciferase expression was measured after 24 hours of treatment and normalized to Renilla Luciferase activity expressed from a co-transfected pRL plasmid. The pRL Vector, which provides constitutive expression of Renilla luciferase, was used in combination with a firefly luciferase vector to co-transfect cells. Expression of Renilla luciferase provides an internal control value to which expression of the experimental firefly luciferase reporter gene may be normalized.

The results show a dose-dependent increase of luciferase expression for Compound 1 with the use of WT RORE. Mutating the RORE negates activity of Compound 1. These results, shown in FIG. 1, indicate RORα activity of Compound 1 as an agonist.

This assay can be used to evaluate other compounds described herein. Where compounds increase luciferase expression, they are RORα agonists, and where they decrease luciferase expression, they are RORα antagonists (or partial agonists or allosteric inhibitors).

Example 4

Expression of RORα-Regulated microRNA.

Figure 2:
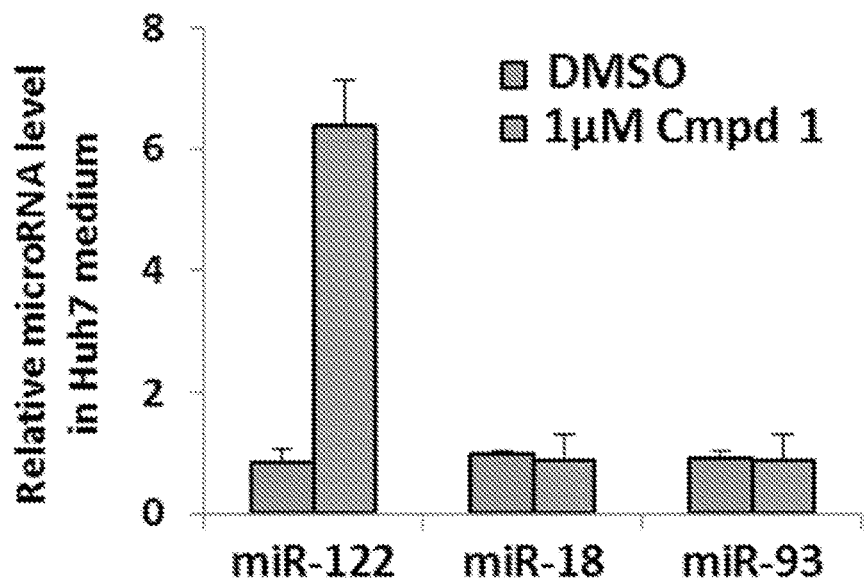
FIG. 2 is a chart showing how Compound 1 specifically increases secretion of miR-122 from Huh-7 cells, shown in terms of relative microRNA levels in Huh7 medium versus DMSO control and Compound 1 (1 µM). Data are presented as error bars=SD. **P<0.01.
Figure 4A:
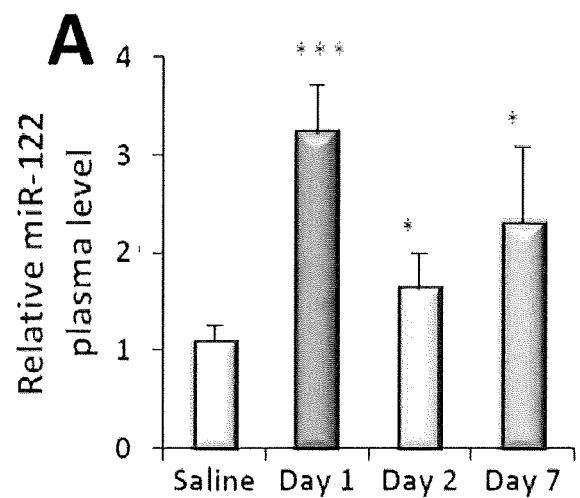
FIGS. 4A-E are charts showing how Compound 1 increases expression of RORα target genes in mice (n=3)– miR-122 and Gpase6.
Figure 4B:
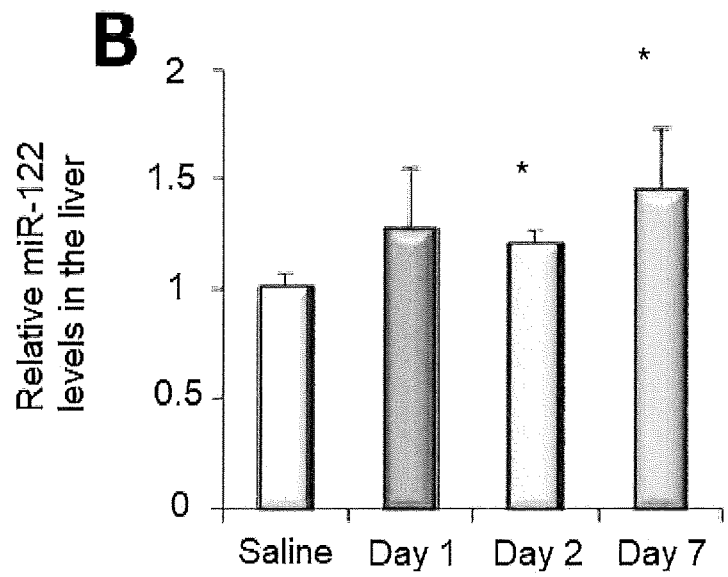
Figure 4C:
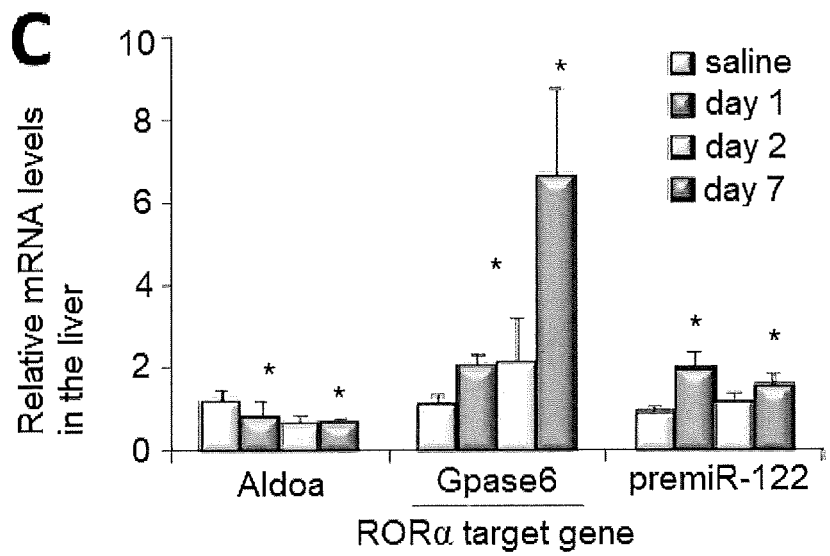
Figure 4D:
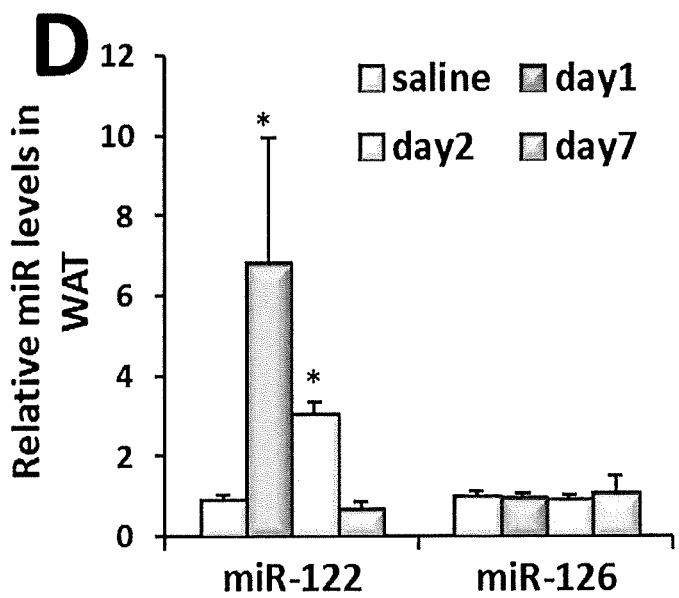
Figure 4E:
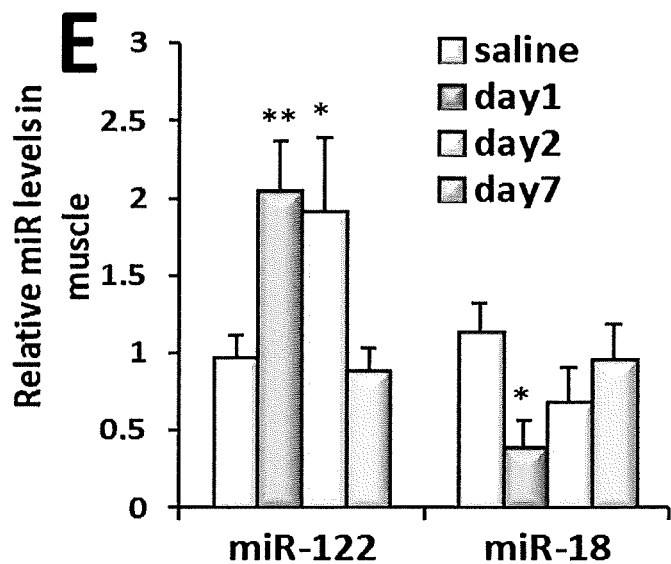
Figure 5A:
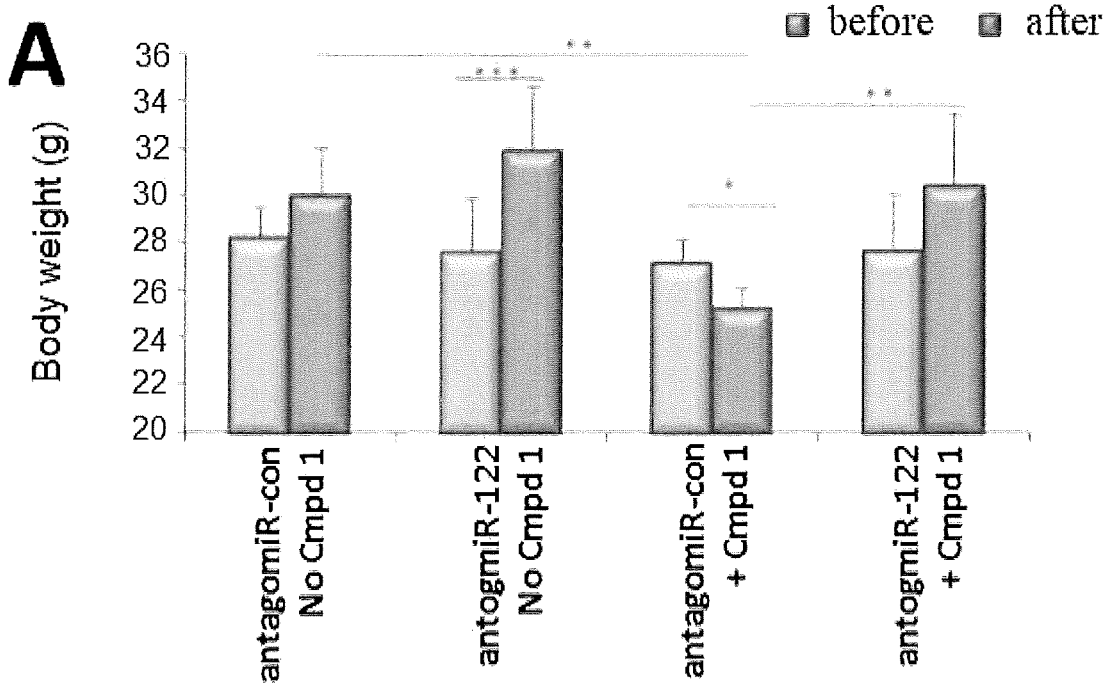
FIGS. 5A-C are charts showing Compound 1 (Cmpd1) treatment reduces body weight and increases energy expenditure via miR-122 activity in high-fat-fed C57BL/6 mice.
Figure 5B:
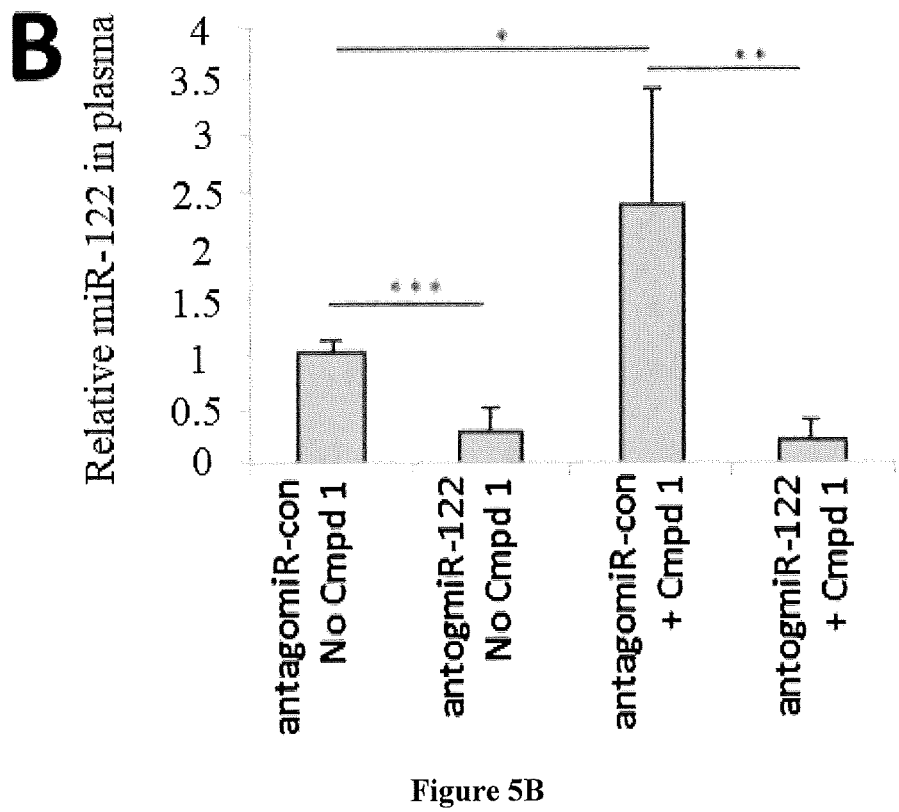
Figure 5C:
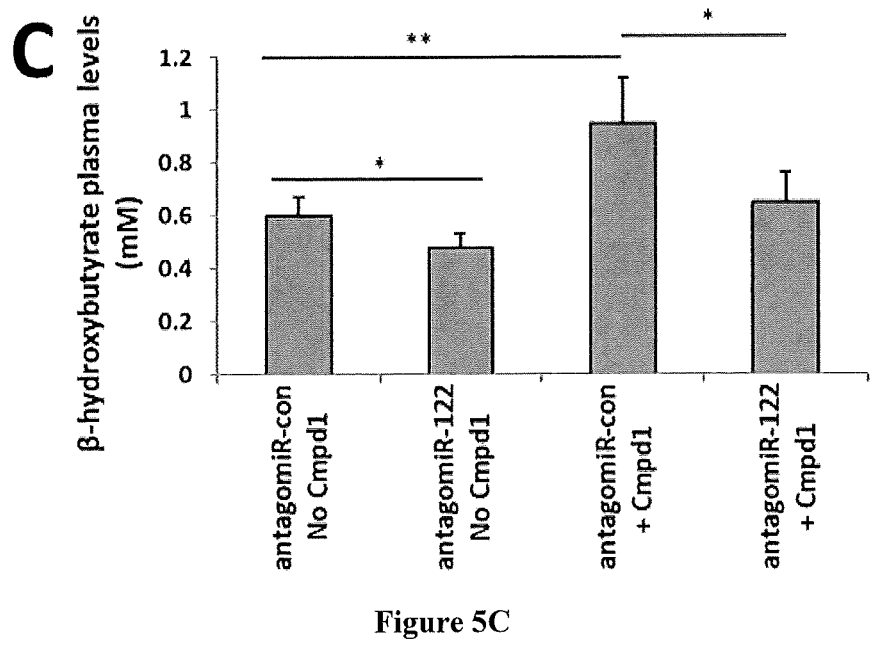
Figure 5D:
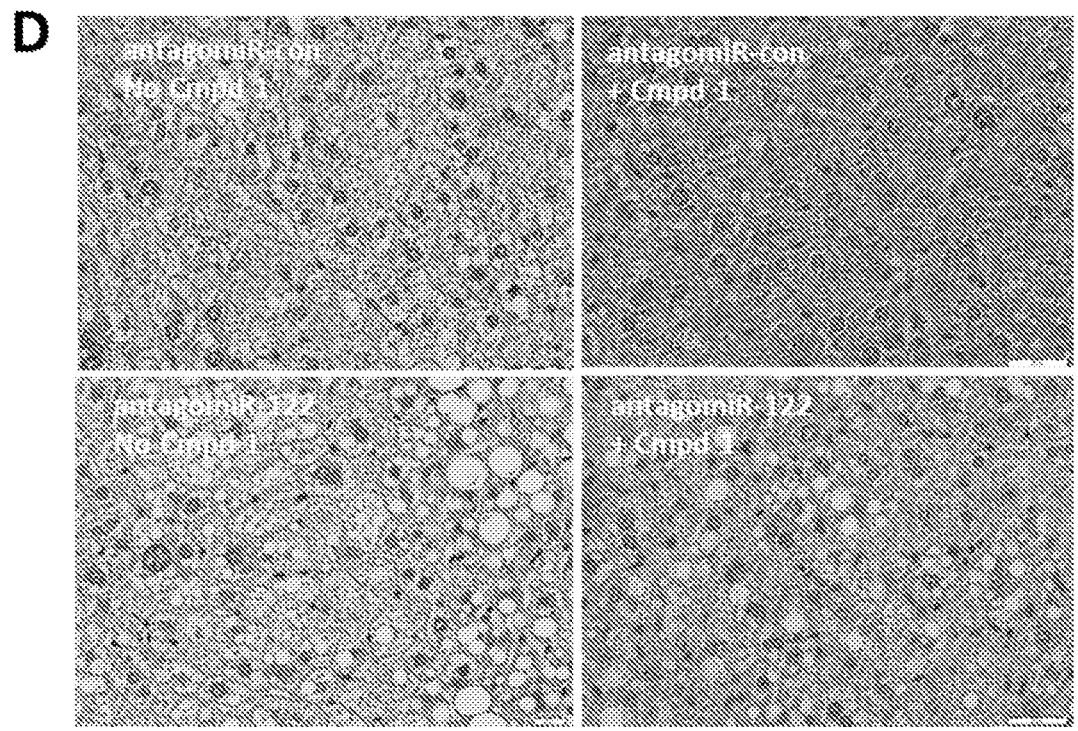
FIG. 5D is a photograph of a representative lipid accumulation visualized by H&E staining of liver sections. N=5. Data are presented as error bars=SD. *P<0.05, P<0.01, *P<0.001.
Figure 6A:
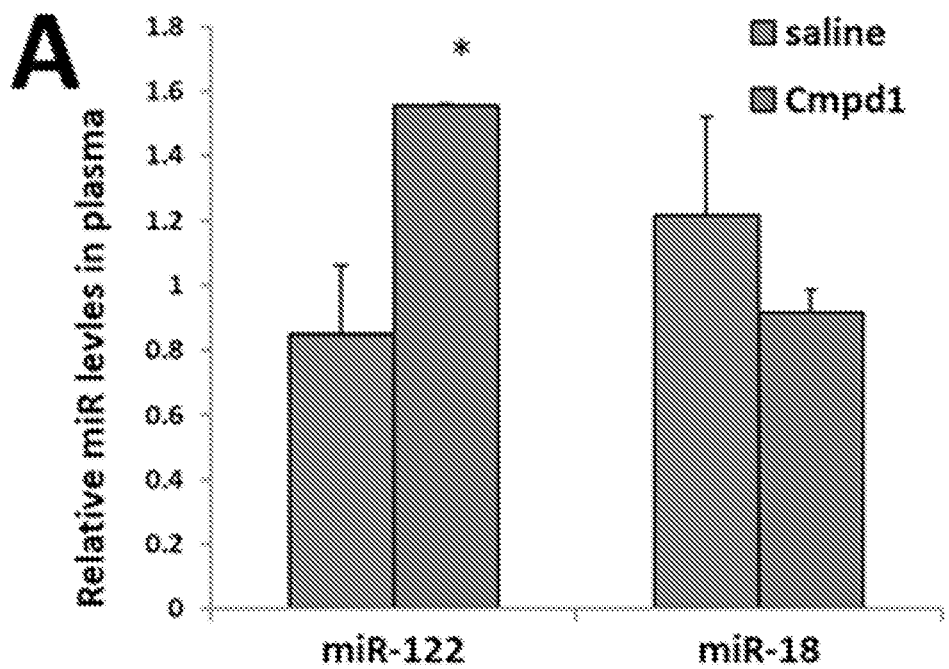
FIGS. 6A-C are charts showing that Compound 1 administration increases miR-122 expression and reduces liver and muscle triglyceride levels in Sgp130FC mice (n=3). Sgp130FC mice were injected (ip) with Compound 1 for four weeks (7.5 mg/kg, twice/week).
Figure 6B:
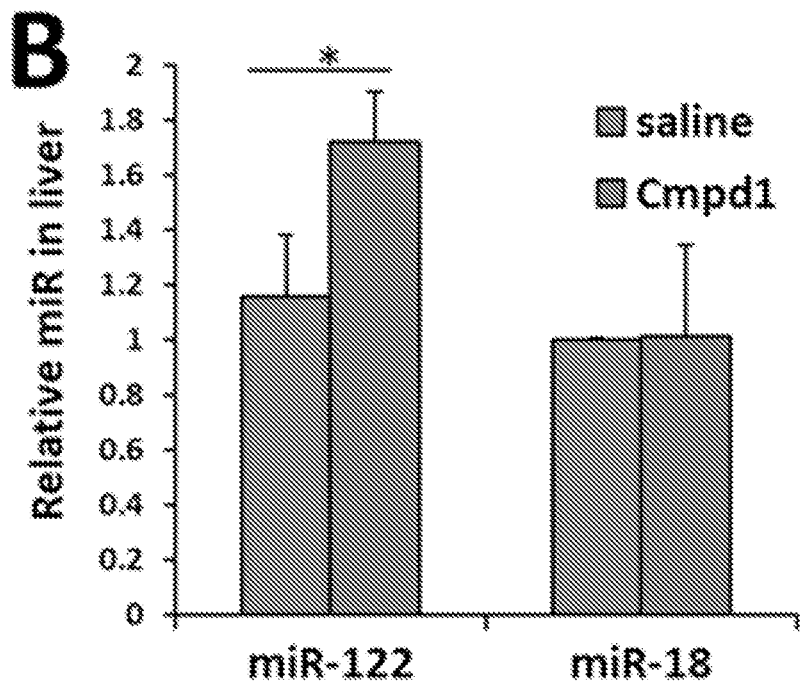
Figure 6C:
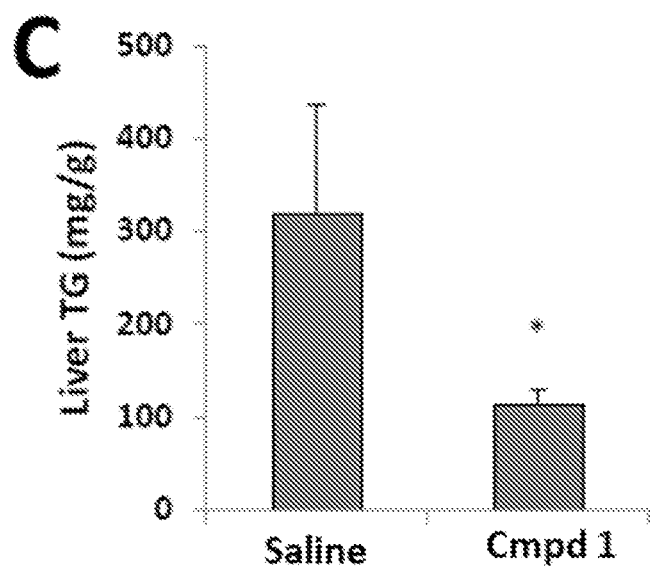
Figure 6D:
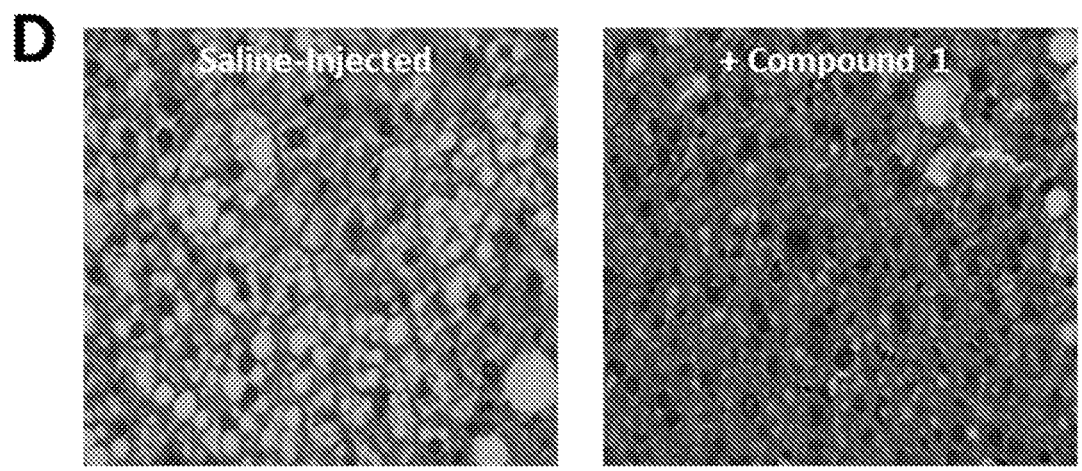
FIG. 6D is a photograph of representative lipid accumulation visualized by H&E staining of liver sections for saline-injected (left side) and Compound 1-injected (right side) mice. The photographs show reduced lipid droplets accumulation when Compound 1 is administered.
Figure 6E:
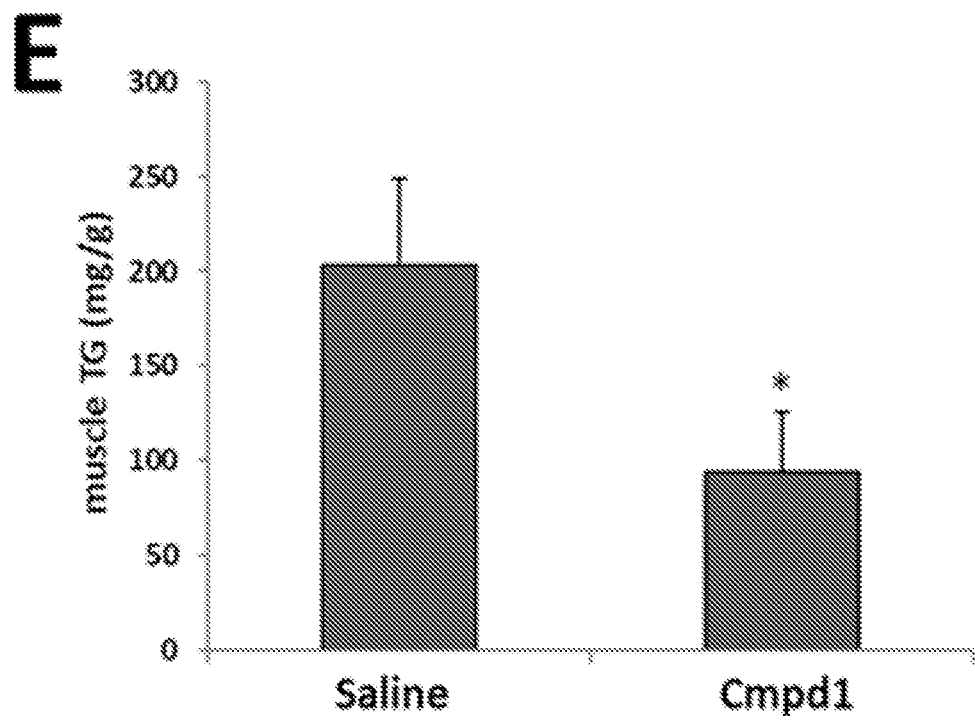
FIG. 6E is a chart showing the colorimetric quantification of triglycerides (TG, in mg/g) in skeletal muscle. Data are presented as error bars=SD. *P<0.05.

Huh-7 cells were treated with 1 µM Compound 1 or vehicle (DMSO) for 24 hours. Secreted microRNA levels in the medium of Huh-7 cells were analyzed by qRT-PCR and were normalized to spiked *C. elegans* miR-39. miR-18 and miR-93 served as controls for secreted microRNA and were not affected following Compound 1 addition. The results are shown in FIG. 2.

Example 5

Modulation of Th17 Populations

Human peripheral blood mononuclear cells (PBMCs) were isolated from four healthy donors. Four experiments were conducted and analyzed by flow cytometry over 3 day assay. The control group had no drug treatment, a second were treated with 10 µM Compound 1, a third group was stimulated with PHA/IL-2 without treatment, and the fourth group was stimulated with PHA/IL-2 and incubated with 10 µM Compound 1. These results show that Compound 1 has no effect on total viability of $CD4^+$ T cells even under PHA/IL-2 stimulation. Further, Compound 1 has no effect on Th17 populations in the absence of PHA/IL-2 stimulation. As shown in FIG. 3, Compound 1 decreases Th17 total population in PBM cells relative to vehicle-control in the presence of PHA/IL-2 stimulation.

Example 6

Modulation of RORα-Regulated Genes in C57BL/6 Mice

Healthy C57BL/6 mice were injected i.p. once with 7.5 mg/kg Compound 1 or saline control. Mice were sacrificed at 1, 2, and 7 day time points post-injection. miR-122 and Gpase 6 mRNA levels were determined by qRT-PCR for each time point. MicroRNA levels were normalized to RNU6; plasma miR-122 was normalized to spiked in *C. elegans* miR-39; and mRNA levels were normalized to HPRT.

These results, shown in FIGS. 4A-E, show that after administration of Compound 1, miR-122 levels are increased in plasma and liver up to 7 days post-injection. Further, the RORα-regulated gene Gpase6 is significantly up-regulated up to 7 days post-injection of Compound 1.

Example 7

Weight Loss in High-Fat-Diet C57BL/6 Mice is Due to RORα Modulation

C57BL/6 mice were fed a 50% high fat diet (HFD) for four weeks. The control cohort received three hydrodynamic tail vein injections of a 5 µg antagomiR-control and six i.p injections of saline over three weeks. A second cohort was hydrodynamic tail vein injected with 5 µg antagomiR-122 (the reverse complement that inhibits activity of miR-122) three times and i.p injections of saline six times over three weeks. A third cohort was injected i.p. with Compound 1 (7.5 mg/kg) twice a week plus antagomiR-control once a week over the course of 3 weeks. The final cohort was injected i.p. with Compound 1 (7.5 mg/kg) twice a week plus antagomiR-122 injections once a week over the course of 3 weeks.

When injected only with antagomiR-control, mice went from approximately 28 g to 30 g over the course of the treatment. Treatment with antagomiR-122 resulted in a larger weight gain to a final body weight of 32 g. The group treated with Compound 1 and antagomiR-control had statistically lower body weight at the end of the experiment compared to the control group (lacking Compound 1). Co-administration of Compound 1 and antagomir-122 did not decrease body weight. As shown in FIGS. 5A-D, secretion of miR-122 was enhanced when treated with Compound 1, which could be reduced to baseline levels with co-administration of antagomir-122. These results suggest that body weight loss is specifically due to Compound 1-modulated secretion of miR-122.

Example 8

Modulation of Liver Triglycerides and Lipid Accumulation in Sgp130FC Mice

Sgp130FC mice specifically blocks IL-6 trans-signaling without affecting classic IL-6 signaling. These mice are useful models for non-alcoholic steatohepatitis (NASH) since they exhibit symptoms of the disease including hepatomegaly, steatosis, and liver inflammation. Nine-month-old Sgp130FC mice were injected i.p. with Compound 1 (7.5 mg/kg) or vehicle control twice a week for four weeks (total of 8 injections). The mice were sacrificed after 4 weeks, triglyceride levels were measured from liver and skeletal muscle and hepatic lipid accumulation was visualized using H&E staining.

Treatment with Compound 1 significantly reduces liver triglyceride levels by approximately 3-fold. Without treatment (injection of saline control), lipid droplets accumulate in the liver visualized as white blobs in H&E staining. Treatment with Compound 1 markedly reduces lipid accumulation and droplet formation in mice.

Detailed Methods

Cell Culture. HCC-derived human cell lines: Huh7 were cultured in DMEM supplemented with 10% fetal calf serum (FCS), 1% penicillin/streptomycin.

Plasmids. The human miR-122 promoter fragments spanning the region from −900 bp relative to the transcription start site (TSS) (plasmids PmiR-122-900) were generated as described previously (1). Mutating the RORα site in the promoter region was performed by PCR using primers P1 and P2, as described previously (2). All primers used to generate the plasmids are described Table 2.

Luciferase assay. For Luciferase assays, cells grown in 24 well plates were co-transfected with a luciferase reporter plasmid (50 ng) and 1 ng of Renilla Luciferase vector (PRL, Promega) using the TransIT-LT1 (Mirus) transfection reagent (MIR 2300, Madison, WI). Firefly and Renilla luciferase activity was assessed using the Dual Luciferase Reporter Assay system (Promega). Readings were taken in triplicates on a Mithras LB 940 Luminometer (Berthold Technologies).

RNA extraction and quantitative Real-Time PCR analysis. Total RNA, including small RNAs, were isolated from 200 µL of plasma or culture media samples using the miRNeasy Mini kit (Qiagen, Valencia, CA, USA) with 2 minor modifications. First, 200 µl of plasma or culture media were lysed with 1 ml of Qiazol solution. Second, a 50 pmol/l of synthesized single strand *Caenorhabditis elegans* miRNA (cel-miR-39) was added as the spike-in control to monitor extraction efficiency. The remainder of the RNA extraction was performed according to the manufacturer's instructions. miRNAs were eluted with 30 µl of RNase-free water. Total RNA, including miRNAs, from cells or tissues were isolated using TRIzol reagent (Invitrogen, Carlsbad, CA, USA). cDNA was synthesized using the Quanta Biosciences qScript™ cDNA Synthesis Kit (95047-100) for mRNA analysis, and using the qScript™ microRNA cDNA Synthesis Kit (95107-100) for miRNAs analysis. qRT-PCR of miRNAs and mRNA was performed using the ABI 7900 HT Real-Time PCR System and a SYBR Green PCR Kit: Quanta Cat. #84018 and #84071 respectively. The fold expression and statistical significance were calculated using the 2-ΔΔ Ct method. All experiments were performed in triplicates.

High Fat diet fed mice. C57BL/6 male mice were fed for 8 weeks a 50% high fat diet (Envigo, DIETTD150235). All mice were kept in a pathogen-free facility, under a 12 h light/dark cycle. Research on mice was approved by the Hebrew University Institutional Animal Care and Ethics Committee.

Compound 1 and AntagomiR injections to mice. C57BL/6 male mice, 7-8 weeks old, or Sgp130FC, 9-month-old male mice, were injected i.p. with 7.5 mg/kg Compound 1 dissolved in saline and 3% DMSO. Saline was injected as control. Mice were hydrodynamic tail vain injected with antagomiR-122 or antagomiR-control (negative control) (5 µg/mouse in 1.5 ml saline). Mice were sacrificed according to the legend of the figure describing the experimental results and the livers, white adipose and skeletal muscle tissues were frozen in liquid nitrogen or in OCT embedded frozen blocks, for further RNA and histologic analysis. AntagomiRs were obtained from Sigma Aldrich, see Table 3.

Triglycerides and β-hydroxybutyrate quantification. To determine the liver and muscle lipid content, muscle and liver tissues (40-80 mg) were homogenized in 0.5 ml of chloroform: Tris solution (v/v, 1:1), the homogenate was transferred to 1 ml of chloroform: methanol solution (v/v, 2:1) centrifuged at 3000 rpm for 10 min. The organic phase was mixed with 5% Triton X100 in chloroform, dried and re-dissolved in water. After lipid extraction, TG concentration in samples was measured with Triglyceride Quantification Kit (BioVision), according to the manufactures instructions. β-hydroxybutyrate was determined utilizing commercial colorimetric kits (BioVision) directly from plasma samples.

TABLE 2

Primers for plasmids constructs.

| Primer Number | Direction | Sequence (5' to 3')[ab] | Restriction sites at 5'-end | Cloning |
|---|---|---|---|---|
| P1 | forward | GAC*ACGCGT*AGTCA ACATGGTGAAACCC | MluI | Mutate RORα sites in miR-122 promoter |
| P2 | reverse | TATTGCTTTTTATT TTTTA*ACTAGT*CCT TTTTTTGAAATGGA | SpeI | Mutate RORα site in miR-122 promoter |

TABLE 3

Synthetic small RNA.

| Name | Sequence |
|---|---|
| antagomiR-122 | 5'-mAsmCsmAmAmAmCm AmCmCmAmUmUmGmUmCm AmCmAmCmUsmCsmCsm As-Chol-3' |
| antagomiR-control | 5'-mCsmAsmCmCmAmCm AmUmAmCmCmGmCmAsm CsmGsmGs-Chol-3' |

Subscript 'm' represent 2'-O Me-modified nucleotides;
Subscript 's' represents a phosphorothioate linkage;
'Chol' represents cholesterol linked through a hydroxyprolinol linkage.

Example 9

Nonalcoholic fatty liver disease (NAFLD) is a major healthcare burden and is associated with the metabolic syndrome, the most prevalent and significant western world clinical epidemic. NAFLD that developed to nonalcoholic steatohepatitis (NASH) has no therapy currently, in spite of major efforts. Reduction of hepatic miR-122 causes liver NASH. We have investigated the mechanism of miR-122 regulation in the liver and found that RORα is an activator of miR-122. The RORα activator Compound 1 was selected based on its effect on increasing miR-122 levels in the liver, plasma and "remote" tissues beneficial effects. In NASH models, we show that Compound 1 reverses all histological manifestations of NASH including steatosis, inflammation and fibrosis. These effects were also associated with beneficial metabolic effects and a reduction in body weight. RORα agonists are therefore proposed as drugs to treat, prevent, and/or reverse NASH.

Introduction

Nonalcoholic fatty liver disease (NAFLD) is most common chronic disease worldwide, affecting over 25% of the global population (Younossi, Hepatology. 2016 July; 64(1): 73-84). NAFLD is associated with increased cardiovascular diseases and diabetes, with 30% of the patients progressing to chronic liver inflammation termed nonalcoholic steatohepatitis (NASH), followed by fibrosis and cirrhosis within 10-30 years. NASH can also progress to hepatocellular carcinoma (HCC) in 15% of the cases, and is the $2^{nd}$ leading cause of cancer-related death worldwide (Younossi, J Hepatol. 2019 March; 70(3):531-544). NASH is tightly associated with metabolic syndrome, that includes obesity, diabetes, hypertension, hypertriglyceridemia and reduced high-density-lipoprotein cholesterol (HDL) levels. Currently there is no approved effective therapy against NASH and the metabolic syndrome. Diet and genetics are inducers and involved in the development of NASH; however, our influence on both is between transient and marginal.

Although NASH is a major healthcare burden, until now there is no approved therapy reversing NASH and its consequences (Konerman, J Hepatol. 2018 February; 68(2): 362-375). A number of compounds were recently developed, some of which have entered into Phase II and Phase III clinical trials. However, none of these shows, until now, a therapeutic effect in all the clinical aspects of NASH, including lipotoxicity, inflammation, fibrosis, insulin resistance and obesity.

MicroRNA-122 (miR-122) is associated with hepatic lipid metabolism (Esau, Cell Metab. 2006 February; 3(2): 87-98.). Its levels decrease in livers of humans with NASH (Cheung, Hepatology. 2008 December; 48(6):1810-20), and increase in blood of these patients. In miR-122 knockout mice NASH develops (Tsai, J Clin Invest. 2012 August; 122(8):2884-97). Steatohepatitis develops in mice injected with anti-miR-122 (Satishchandran, "MicroRNA 122, Regulated by GRLH2, Protects Livers of Mice and Patients From Ethanol-Induced Liver Disease," Gastroenterology, 154(1): 238-252 (2018). These mice later develop HCC. MiR-122 expression is dependent on inflammation signaling, which also cases it secretion from the liver to have remote effects on other organs. Furthermore, miR-122 is also regulated by free fatty acids (FFA) mediated by the activation hepatocytes ROR$\alpha$. MiR-122 increase in hepatocytes by the FFA-ROR$\alpha$ machinery, that causes hepatic triglycerides (TG) suppression by targeting and reducing the levels of enzymes involved in TG biosynthesis (Chai, Gastroenterology. 2017 November; 153(5):1404-1415). Based on these observations, an approach was undertaken to determine whether activating ROR$\alpha$ could reverse all associated phenotypes with NASH. On information and belief, ROR$\alpha$ was never before suggested to have a direct beneficial effect on NASH.

A panel of ROR$\alpha$ agonists was developed, and one compound was selected based on its effect on activating the miR-122 promotor. This activation caused beneficial hepatic effects on lipotoxicity in the liver in mouse models, reduced liver inflammation, and reversed fibrosis. Furthermore, this ROR$\alpha$ agonist also reduced remote adipose tissue inflammation, improved insulin resistance, and reduced the weight of the obese mice.

Results
The Effect of miR-122 on Lipid Metabolism in Mice on a High Fat Diet (HFD)

One initial question was what the function miR-122 is in livers of mice under a high fat diet (HFD) that cause lipotoxicity. In humans, it was shown that miR-122 in livers with NASH is significantly lower (Williams et al., "New advances in molecular mechanisms and emerging therapeutic targets in alcoholic liver diseases," World J Gastroenterol 20(36):12908-33 (2014)). In our previous report, we have shown that miR-122 targets TG biosynthesis by reducing the enzymatic activity of AGPAT1 and DGAT1 (Chai, Gastroenterology. 2017 November; 153(5):1404-1415). To test the effect of reducing miR-122 in HFD livers we had administered, by a hydrodynamic injection an antagomir-122 to the liver that blocks and degrades miR-122 in hepatocytes (Krutzfeldt, Nature. 2005 Dec. 1; 438(7068):685-9). This cased the reduction of mature miR-122 in the liver also in HFD mice (Esau, Cell Metab. 2006 February; 3(2):87-98). The levels of miR-122 precursors were also reduced to some extent. Furthermore, the antagomir-122 injection also reduced significantly the plasma level of miR-122. The antagomir-122 effect was also apparent on remote tissues, reducing miR-122 in white adipose tissue (WAT). The reduction of mature miR-122 levels in WAT as well as in muscle is a result of reduced secretion of miR-122 from hepatocytes and not by reducing miR-122 expression non-liver tissues (Chai, Gastroenterology. 2017 November; 153 (5):1404-1415).

The remote effect on muscle tissue of reducing miR-122 plasma levels was correlated with an increase in muscle TG levels. The reduction of plasma miR-122 levels was associated with an increase of liver fat droplets and total TG liver content. The biochemical effect of liver miR-122 reduction was manifested by a decrease in $\beta$-oxidation, as well as $\beta$-oxidation pathway and a reduced plasma level of FFA. All these are known indications of an increase in storage of triglycerides (TG) in tissues and the reduction in energy expenditure. The overall effect on mice weight is apparent. Blocking miR-122 by antagomir upon HFD caused an increase in mice weight, liver weight and an increase in liver to body weight index. The effects of reducing miR-122 in the liver and systemically (remote tissues) are causing an increase in liver lipids, decrease in $\beta$-oxidation and energy expenditure, and having a systemic effect simulating altogether features of the metabolic syndrome.

ROR$\alpha$ Activation

ROR$\alpha$ regulates miR-122 expression in mice, and this is mediated through FFA (Chai, Gastroenterology, Volume 153, Issue 5, November 2017, Pages 1404-1415). The levels of ROR$\alpha$ decreased upon HFD, and increased upon activation with the ROR$\alpha$ activator Compound 1. However, the potential relevance to human metabolism and NASH needs further investigation. Human NASH data sets were initially investigated (see Arendt, Hepatology, Volume 61, Issue 5, Pages 1565-1578 (2015) and Starmann, PLoS One. 2012; 7(10):e46584) (GSE33814 and GSE89632 respectively). ROR$\alpha$ is reduced in NASH patients. Furthermore, ROR$\alpha$ target genes are decreased in these samples. The expression of miR-122 target genes is increased in humans in which miR-122 is decreased. The expression of genes that are involved in FFA biosynthesis pathway and are associated with fatty liver (Dorn et al, Mol Nutr Food Res. 2010 July; 54 Suppl 2:S205-13, Knebel, PLoS One. 2012; 7(2): e31812), are negatively correlated with ROR$\alpha$. MiR-122 target genes increase upon ROR$\alpha$ increase in human livers. MiR-122 target genes are also negatively correlated with ROR$\alpha$ expression. The expression of FGF21 is positively correlated with pre-miR-122.

FGF21 is a known target of ROR$\alpha$ (Wang, J Biol Chem. 2010 May 21; 285(21):15668-73). Recently, it was shown that FGF21 is upregulated in the liver upon cold exposure (Ameka, Sci Rep. 2019 Jan. 24; 9(1):630). While not wishing to be bound to a particular theory, it is believed that this could be due to an increase of ROR$\alpha$ in the cold. To assess this assumption, HUH7 human HCC cells were transfected with a ROR$\alpha$ reporter system in which luciferase is expressed from the miR-122 promoter that harbors a ROR$\alpha$ binding site. The increase in primiR-122 and miR-122 levels is associated with a decrease in miR-122 target genes, Aldo A and Dgat1. MiR-122 expression is cold sensitive, depending on ROR$\alpha$ binding to its consensus sequence in the miR-122 promotor. In an effort to determine whether the ROR$\alpha$-miR-122 machinery is relevant to humans, as well, a human study was conducted (Hadassah University Hospital IRB approval #HMO-0025-18). In this study, humans were undergoing major blood vessels cardiovascular surgery with the usage of the cardio-pulmonary machine and systemic body cooling. MiR-122 expression was measured, and a significant increase in plasma miR-122 was found upon temperature reduction.

These results suggested that an increase in ROR$\alpha$ activity and an increase in the activity of the miR-122 promotor can increase the hepatic beneficial effects of miR-122 on NASH. In addition, this effect could be inducing a therapeutic effect systemically, such as improving insulin resistance and reducing adipose tissue and body mass. To this end, a panel of ROR$\alpha$ agonists was generated.

ROR$\alpha$ is composed of an N-terminal activation function 1 (AF-1) that interacts with coactivator proteins followed by a DNA-binding domain containing two zinc-finger motifs, a flexible hinge region, and a C-terminal ligand binding domain (LBD) that contains a hormone-responsive activation function 2 (AF-2). The binding of an agonist to the ROR$\alpha$-LBD induces a conformational change that enables binding of coactivator proteins to the AF-2. The most potent agonist solved in complex with RORα-LBD is cholesterol sulfate (PDBID 1S0X). This ligand-binding pocket of this crystal structure was targeted by high throughput virtual screening to identify novel RORα agonists. A proprietary library of drug-like 300,000 compounds were evaluated for binding using the Schrodinger Maestro Glide HTVS workflow. The top 200 compounds were further scored using Prime MMGBSA with 5 Å flexibility allowed. The top 100 compounds were visually inspected, and twelve were selected for evaluation using the luciferase assay at the miR-122 promoter region.

RORα Liver and Systemic Effects are Mediated Through miR-122

The following experiments were conducted in an effort to determine whether the RORα metabolic and biochemical effects are mediated through miR-122. The activation by Compound 1 is through the RORα DNA binding/activation to the miR-122 promotor by mutating this site in the miR-122 promotor. Upon exposing HuH7 cell to Compound 1 for 16 h, cells levels of miR-122 did not change, but a significant miR-122 was secreted to the medium (there was no apparent toxicity to the cells as measured by LDH release, data not shown)). However, when Compound 1 was administered to mice for a number of weeks, miR-122 levels increased both in the liver and in the plasma. This was associated with an increase of hepatic precursor's levels of both Pre-miR-122 and Pri-miR-122, as well as a decrease in a known target of miR-122, AldoA and an increase in G6Pase, a known RORα target gene (Chauvet, PLoS One. 2011; 6(7):e22545). MiR-122 reaches remote tissues. To assess the effect of Compound 1 on this miR-122 remote effect, miR-122 was measured in heart muscle tissue, which showed an increase in the mature miR-122 levels with a reciprocal down-regulation of three miR-122 target genes. Mature miR-122 was also identified in other organs as WAT and muscle after administration of Compound 1 (the levels of pri-miR-122 in muscle tissue were not detected, suggesting that the mature miR-122 in the muscle was not expressed from the miR-122 promoter).

In an effort to determine whether the mechanism of action of miR-122 and Compound 1 are aligned at the same pathway, an experiment was designed in which both molecules, together and each separately, were administered. In this study, mice were fed with a 50% HFD and therapy was initiated 4 weeks after the animals were already on a diet, to establish NASH prior to treatment. Therapies (antagomiRs given once a week, due to a prolonged half time, and RS twice weekly, due to a plasma t/2 of 2.7 hrs) were initiated after 4 weeks and given for 3 weeks. The mice were weighed from week 3 and therapies initiated a week later. Control mice (antagomiR-control once a week and DMSO diluted in saline twice a week) had a steady increase in weight. Mice in which an antagomir-122 was administered had the highest increase in weight. Those treated with the RORα agonist Compound 1, their weight steadily decreased and lost weight. Mice administered both, antagomir-122 and Compound 1, their weight returned exactly to that of controls animals. This phenomenon suggests that miR-122 and Compound 1 probably antagonize one another. Furthermore, it also indicated that the reduction in weight is not due to a toxic effect. At cessation of the experiment, there was a significant increase in weight in the antagomiR-122 treated animals, indicating that a reduction in miR-122 in the liver is associated with a systemic effect, whereas the administration of Compound 1 significantly reduced weight also at end of experiment. The liver weight was accordingly reduced. The liver was further analyzed to assess lipotoxicity. Hepatic lipid droplets and TG content are reduced in Compound 1 treated mice, this reduction is completely abolished in antatagomiR-122 injected mice, suggesting that the beneficial effect of Compound 1 on steatosis is mediated by miR-122 activity. A surrogate marker for energy expenditure, β-hydroxybutyrate, was also measured. A reduction in energy expenditure is associated with reduced miR-122, and energy expenditure increased upon treating with Compound 1.

These effects were associated with a liver and plasma reductions of miR-122 upon administration of antagomiR-122 and an increase of miR-122 in both liver and plasma when Compound 1 was administered. MiR-122 increase had also effects on its target genes including Agpat1, Dgat1 and FGF21. The liver antagomiR-122 and the Compound 1 had also an effect on muscle with a similar pattern to that in the liver, possibly through miR-122 secretion effects. This resulted in an effect on muscle TG content, in which antagomiR-122 had increased and Compound 1 had decreased TG content in the muscle, probably through liver derived secreted miR-122. The level in the liver of FGF21 message is correlated associated with pri-miR-122 levels, suggesting a co-regulation. These observation strengths our hypothesis that miR-122 levels control, either by reducing hepatic miR-122 levels by antagomiR-122, or increase it, by Compound 1, has both a liver/central and remote/peripheral effects. The overall effects of Compound 1 culminated in a significant weight reduction associated with a reduction of lipotoxicity.

The Anti-Lipotoxic and Improved Metabolic Effects by Activating the RORα-miR-122-Triglycerides Circuitry After showing that Compound 1 is a clinically relevant miR-122 activator with beneficial biochemical effect, the study next aimed to determine its effect on lipotoxicity and metabolism. Compound 1 was administered to mice with an established NASH. The activator increased both miR-122 levels in the livers of mice as well as in plasma. The administration of the RORα activator/agonist, Compound 1 compound, resulted in an increase in miR-122 precursors as well as in RORα targets. These results demonstrated that the activator was truly functioning in the model. In the NASH model, Compound 1 significantly reduced weight of animals who were given HFD. This effect is apparent also upon observing single animal effect and by calculating body to liver weight. The RORα activator reversed the lipotoxic effect of mouse livers and their TG content. Compound 1, which induces miR-122 production and secretion from hepatocytes, also had an effect on reducing WAT inflammation. These beneficial histological and biochemical effects not only resulted in whole body weight reduction, but also were associated with an improvement in insulin tolerance.

The Anti-Inflammatory and Anti-Fibrogenic Effects of Activating the RORα-miR-122-Triglycerides Circuitry with Compound 1

Once it was observed that the RORα activator Compound 1 had significant anti-lipotoxic properties in the liver and remote tissues, reduced weight and had beneficial metabolic properties, the effects of Compound 1 on liver inflammation and fibrosis were determined. The effects of Compound 1 on liver inflammation and fibrosis were assessed in the mouse atherogenic diet model (Anavi, Lab Invest. 2015 August; 95(8):914-24). After liver inflammation and fibrosis developed at week 3 of diet, animals initiated to receive Compound 1. After 3.5 additional weeks, in which animals received 3 times weekly Compound 1, animals were assessed for numerous endpoints. Compound 1 significantly improved liver enzymes. It was confirmed that mature miR-122 increased both in tissue and plasma following the administration of Compound 1. Compound 1 significantly improved liver inflammation. This improvement in inflammation was associated with a significant reduction in liver fibrosis, as assessed by two measures, Masson Trichrome and αSMA staining. There was no effect of Compound 1 on liver vasculature as depicted by CD34 staining of these mice livers (data not shown). The effect of the RORα activator, Compound 1, was apparent also on fibrosis driver genes.

Discussion

Activating RORα has major anti-NASH beneficial effects. These effects are both on the liver pathologies associated with NASH and on peripheral tissues to the liver. The beneficial effect of RORα on NASH and metabolic syndrome associated conditions is mediated through mature miR-122, although additional RORα activities could potentially contribute to these beneficial effects. The role of miR-122 is through suppressing hepatic lipotoxicity, the first hit (Engin, Adv Exp Med Biol. 2017; 960:443-467) of fatty liver, by targeting the expression of central enzymes in TG biosynthesis. Based on the evidence, it was shown that RORα activates, the expression of miR-122 and also increases its secretion into the plasma, to reach WAT, muscle and heart muscle, to expedite its remote effects, we propose that the effect of RORα activation is both in the liver and systemic.

In an effort to control the activation of RORα and enhance its potential beneficial effects, a screening system was developed to identify compounds that enhance RORα activity on miR-122 expression with preferred anti-NASH effects. We have identified a compound (Compound 1) which has potential therapeutic effects in NASH. Interestingly, Compound 1, which increased miR-122 expression and secretion, showed significant metabolic effects including reducing fatty liver, suppressing liver inflammation associated with hepatic lipotoxicity, reversing liver fibrosis, improving insulin resistance, and reducing body weight.

NASH is a high priority unmet need for therapy worldwide. There is not a single approved drug today for NASH. Many drugs are prescribed for specific maladies associated with metabolic syndrome and NASH (Wattacheril, Annu Rev Pharmacol Toxicol. 2018 Jan. 6; 58:649-662). However, NASH patients are still without a therapeutic option other than proposing them to undergo a specific diet e.g. a Mediterranean diet which improves NAFLD to some extent (Marchesini, Hepatology. 2016 June; 63(6):2032-43). Many compounds are in the drug development pipeline, some showing interesting promises (Friedman, Nat Med. 2018 July; 24(7):908-922), and some failing to meet important endpoints (Loomba, Gastroenterology. 2019 January; 156 (1):88-95).

A number of previous reports, and those of ours, pointed to the potential of "hijacking" the mechanistic action of miR-122 as an anti lipotoxic effector in the liver. One reason that we had decided to investigate the potential therapeutic effects of miR-122, in addition of it being a "natural" effector, is the fact that it behaves as a "miR hormone". MiR-122, like many other microRNAs, are produced in one tissue, has an anti-lipemic effect in the liver and reaches remote tissues. It has been shown that miR-122 is produced and secreted out of the liver and reaches the kidney where it targets erythropoietin, reduces its protein levels and causes anemia (Rivkin, M. et al. Inflammation-Induced Expression and Secretion of MicroRNA 122 Leads to Reduced Blood Levels of Kidney-derived Erythropoietin and Anemia. Gastroenterology (2016)).

The machinery of producing miR-122 in the liver is robust. Each hepatocyte stores 250,000 copies of miR-122 as well as miR-122* (Simerzin, Hepatology. 2016 November; 64(5):1623-1636). The effective remote activity of miR-122 is dependent on the high production and secretion of miR-122 to generate high plasma levels. This high production rate suggests that miR-122 could be translated into an effective therapeutic compound. However, rather than developing a system in which a synthetic miR-122 (mimic-miR-122) is synthesized, made as a drug and injected to patients with NASH for years, it would have been preferred to develop a small drug that induces the expression of the hepatic endogenous miR-122, and could be given daily to patients. MiR-122 is also expressed and secreted by TNFα signaling. However, injecting TNFα is not relevant in the clinical setting of NASH. MiR-122 also has additional therapeutic properties, which are relevant to NASH. MiR-122, both miR-122-5p and miR-3p (miR-122*) have tumor suppressive effects Simerzin, Hepatology. 2016 November; 64(5):1623-1636 (Luna, et al., Mol Cell. 2017 Aug. 3; 67(3):400-410), (Sun, et al., Cancer Cell. 2016 Nov. 14; 30(5):723-736).

In NASH patients, such a positive "side-effect" is important clinically, which adds a motivation to develop pro-miR-122 based compounds to drugs (Bandiera, J Hepatol. 2015 February; 62(2):448-57). The potential beneficial role of RORα in NASH prevention, was recently suggested. NASH is aggravated in RORα knockout (KO) mice (Kim et al., Sci Rep. 2017 Nov. 22; 7(1):16041). Liver macrophages are converted to a M2 anti-inflammatory phenotype by increasing the production of Maresin 1 (MaR1), in macrophages, in a RORα dependent manner (Han et al., J Clin Invest. 2019 Mar. 11; 130:1684-1698). However, in these reports only the inflammatory NASH phenotype was prevented and not treated.

The data shown in this report proposes that RORα activation, which increases miR-122 both in the liver and reaches other organs, including adipose tissue, has a substantial anti-NASH activity. RORα activators are therefore proposed as promising compounds to be developed and assess for their clinical beneficial effects on NASH in patients.

Materials and Methods

Cell Culture

Human hepatocellular carcinoma cell line-Huh7 were cultured in DMEM supplemented with 10% fetal calf serum (FCS), 1% penicillin/streptomycin (Thermo Scientific, Waltham, MA, USA). Cells were cultured at 37° C. in a humidified atmosphere containing 5% $CO_2$, except for experiment in which cells were placed in 32° C. as indicated in the text.

RNA Extraction and Quantitative Real Time RT-PCR

Total RNA, including small RNAs, were isolated from 200 μL of plasma or culture media samples using the miRNeasy Mini kit (Qiagen, Valencia, CA, USA) with 2 minor modifications. First, 200 μl of plasma or culture media were lysed with 1 ml of Qiazol solution. Second, a 50 pmol/l of synthesized single strand *Caenorhabditis elegans* miRNA (cel-miR-39) was added as the spike-in control to monitor extraction efficiency. The remainder of the RNA extraction was performed according to the manufacturer's instructions. miRNAs were eluted with 30 μl of RNase-free water. Total RNA, including miRNAs, from cells or tissues were isolated using TRIzol reagent (Invitrogen, Carlsbad, CA, USA). cDNA was synthesized using the Quanta Biosciences qScript™ cDNA Synthesis Kit (95047-100) for mRNA analysis and using the qScript™ microRNA cDNA Synthesis Kit (95107-100) for miRNAs analysis. qRT-PCR of miRNAs and mRNA was performed using the ABI 7900 HT Real-Time PCR System and a SYBR Green PCR Kit: Quanta Cat. #84018 and #84071 respectively. The fold expression and statistical significance were calculated using the 2-ΔΔ Ct method. All experiments were performed in triplicates. The primers used for qRT-PCR are shown in Table 1.

Plasmids

The human miR-122 promoter fragments spanning the region from −900 bp relative to the transcription start site (TSS) and mutating the RORα binding site (plasmids PmiR-122-900 and PmiR-122-RORα mut, respectively) were generated as described previously 1,2.

Transfections

For Luciferase assays, cells grown in 24 well plates were co-transfected with a luciferase reporter plasmid (50 ng) and 1 ng of Renilla Luciferase vector (PRL, Promega) with Lipofectamine LTX (Invitrogen) transfection reagent. For all experiments, the transfection performed using serum-free medium (Opti-MEM; Cat #31985070; Thermo Scientific).

Luciferase Activity Assay

Following transfections, the cells were lysed with passive lysis buffer (Cat #E1941; Promega), shaking for 20 min at RT and transferred into appropriate 96-well plate. Firefly and Renilla luciferase activity was assessed using the Dual Luciferase Reporter Assay system (Cat #E1910; Promega) on a luminometer Mithras 2000 (Centro XZ, LB960, Berthold Technologies, Bad Wildbad, Germany). The luciferase activity was normalized to Renilla luciferase activity. Readings were taken in triplicate.

RORα Agonist Treatments

Commercial RORα agonist SR1078 (Cayman Chemical) and RORα compounds stocks were prepared by dissolving in DMSO (1 mg/ml). Huh7 cells were treated overnight with 5 μM SR1078 or with 1 μM of all other tested compounds. DMSO alone (0.2%) was used as control. The RORα agonist, Compound 1 as dissolved in saline and up to 5% DMSO, and was injected i.p. to mice in the dosage according to the text. Triglycerides, free fatty acids and 3-hydroxybutyrate were quantified.

To determine the liver and muscle lipid content, muscle and liver tissues (40-80 mg) were homogenized in 0.5 ml of chloroform: Tris solution (v/v, 1:1), the homogenate was transferred to 1 ml of chloroform:methanol solution (v/v, 2:1) centrifuged at 3000 g (at −2° C.) for 10 min (Heraeus Megafuge 16R centrifuge). The organic phase was mixed with 5% Triton X100 in chloroform, dried and re-dissolved in water. After lipid extraction, triglyceride (TG) concentration in samples was measured with Triglyceride Quantification Kit (BioVision), according to the manufactures instructions. Plasma Free fatty acids and β-hydroxybutyrate were determined utilizing commercial colorimetric kits (BioVision) directly from plasma samples.

Animal Studies

Male C57BL/6 mice, 7-8 weeks old, were purchased from Harlan Laboratories (Jerusalem, Israel). All mice were kept in a pathogen-free facility, under a 12 h light/dark cycle. Mice were handled according to the criteria outlined in the "Guide for the Care and Use of Laboratory Animals" prepared by the National Academy of Sciences and published by the National Institutes of Health. Research on mice was approved by the Hebrew University Institutional Animal Care and Ethics Committee; ethics number MD-15-14423-3.

AntagomiR-122 Treatment of High Fat Diet (HFD) Fed Mice

C57BL/6 mice, 7 to 8 weeks old, were fed chow or 50% HFD, consisting of 50% Fat, 20% Sucrose, 10% Fructose, 1.25% Chol) (Envigo, TD.150235) for 4 weeks. In experiments of miR-122 repression by antagomiR, mice were hydrodynamic tail vain injected with antagomiR-122 or antagomiR-control (5 μg/mouse in 1.5 mL saline) once a week for 4 weeks and were still fed HFD or chow diet. After 4 weeks of injections mice were sacrificed and the livers, white adipose, and skeletal muscle tissues were frozen in liquid nitrogen or in optimum cutting temperature embedded frozen blocks, for further RNA and histologic analysis. AntagomiRs were obtained from Sigma-Aldrich (St Louis, MO); see Table 2.

Compound 1 and AntoagomiR-122 Treatment of HFD or Atherogenic Diet-Fed Mice

Male C57BL/6J mice, 7 to 8 weeks old, were housed randomly in standard cages and were fed a HFD, or atherogenic diet (consisting 1% Chol and 0.5% cholic acid, see also Table 3). All mice had free access to water during the experimental period. During the feeding period body weight was monitored every 3 days. In the HFD experiment, after 4 or 6 weeks, the resultant obese mice were treated with antagomiR-122 (5 ag/mouse once a week for 3 weeks), or i.p. injected with Compound 1 (RORα agonist, 7.5 mg/kg twice a week for 3 weeks; or 15 mg/kg 3 times a week for 3 weeks). The obese control (HFD) group was administered only saline with DMSO and antagomiR-control. After 3 weeks of treatment mice were sacrificed and livers were taken for RNA-seq analysis. Livers, white adipose, and skeletal muscle tissues were frozen in liquid nitrogen or in optimum cutting temperature embedded frozen blocks, for further RNA and histologic analysis. In the atherogenic diet experiment mice were treated with 15 mg/kg Compound 1 after 3 weeks with the diet. After 3.5 weeks of treatment, mice were sacrificed, and the livers were frozen in liquid nitrogen or in optimum cutting temperature embedded frozen blocks. Plasma was collected from atherogenic diet-fed mice and saved in −20° C. for ALT and AST analysis using the Reflotron® Analyzer and test-strips (Roche).

Multi-Parameter Metabolic Assessment

Metabolic and activity profiles of the mice were measured, by using the Promethion High-Definition Behavioral Phenotyping System (Sable Instruments, Inc., Las Vegas, NV, USA), which is a multi-parameter assessment incorporating sub-systems for open-circuit indirect calorimetry, feeding, water intake, activity, running wheel and body mass measurements in a conventional live-in home cage that minimizes stress. Data acquisition and instrument control were performed using the MetaScreen software version 2.2.18.0, and the obtained raw data were processed using ExpeData version 1.8.4 using an analysis script detailing all aspects of data transformation. C57BL/6 mice were fed for 6 weeks with HFD and then treated with 15 mg/kg Compound 1 3 times a week for 2 weeks, then were placed in metabolic chambers, with a free access to food and water and were subjected to a standard 12 h dark/12 h dark cycle, which consisted of a 24 h acclimation period followed by a 48 h sampling duration. Respiratory gases were measured by using the GA-3 gas analyzer (Sable Systems Inc., Las Vegas, NV, USA) using a pull-mode, negative-pressure system. Air flow was measured and controlled by the FR-8 (Sable Systems Inc., Las Vegas, NV, USA), with a set flow rate of 2000 mL/min. Water vapor was continuously measured and its dilution effect on $O_2$ and $CO_2$ were mathematically compensated. Effective mass was calculated by ANCOVA analysis. Respiratory quotient (RQ) was calculated as the ratio of VCO2/VO2. Total energy expenditure (TEE) was calculated as VO2×(3.815+1.232×RQ), normalized to effective body mass, and expressed as kcal/h/kgeff.Mass. Fat oxidation (FO) and carbohydrate oxidation (CHO) were calculated as: FO=1.69×VO2−1.69×VCO2 and CHO=4.57× VCO2-3.23×VO2 and expressed as g/d/kgeff.Mass. Ambulatory activity and position were monitored simultaneously with the collection of the calorimetry data using the XYZ beam arrays with a beam spacing of 0.25 cm.

Oil Red O Staining

Liver tissues were embedded in Optimal Cutting Temperature gel and cut into 10 μm frozen sections. For Oil Red O staining, a stock solution of Oil Red O (Sigma-Aldrich) (1 g/10 mL in Propylene Glycol) was prepared, filtered, and protected from light. Frozen sections were dipped in formalin, stained with Oil Red O for 15 min, followed by counterstaining with hematoxylin for 30 sec.

Human Blood Samples and Heparin Elimination

For the measurement of miR-122, FFA and human FGF21 (abcam) analysis in blood samples collected from patients undergoing major blood vessels cardiovascular surgery with the usage of the cardio-pulmonary machine and systemic body cooling. This was performed under the approval of the Hadassah Hospital IRB committee approval number 0025-18-HMO. Informed consent and permission to use biological materials for research were obtained from all subjects. Tube no. 2 indicates the time during the surgery before cooling the patient and Tube no 3. represents the time when the body temperature was the lowest during the surgery. Heparin elimination from RNA solutions isolated from plasma samples of patients was performed according to the protocol described previously 3,4, briefly, a 5 μL RNA sample in water was mixed with 5 μL of heparinase working solution (0.085 IU/mL of Heparinase I (Sigma-Aldrich; catalogue no H2519), 2000 units/mL of RiboLock RNase Inhibitor (Life Technologies; catalogue no E00381), 10 mmol/L Tris HCl pH 7.5, 2 mmol/L $CaCl_2$), 25 mmol/L NaCl) and incubated at 25° C. for 3 h. After reaction the samples were directly used in reverse transcription reactions as RNA templates.

Insulin Tolerance Test

At 4 months of age, an insulin tolerance test was performed on fasted C57BL/6 male mice following HFD feeding for 9 weeks following Compound 1 or saline with DMSO injections. Mice received an i.p. injection of human insulin (Actrapid) at a dosage of 0.88 units/kg followed by glucose checks every 20 minutes. Glucose levels were measured at 0, 20, 40, 60, 80, and 100 minutes post-insulin injection. Glucose measurements were assessed on blood from the tail following a tail snip at indicated time-points using a blood glucometer (Accu-Chek) and test strips (Accu-Chek).

Tissue Histology and Immunohistochemistry

Livers and adipose samples were placed in 4% buffered formaldehyde for 24 hours, followed by 80% ethanol and then embedded in paraffin blocks. Liver and adipose tissues were cut into 5 mm sections, deparaffinized with xylene and hydrated through graded ethanol. For the H&E staining, tissue sections were stained with hematoxylin (Emmonya Biotech Ltd.) and eosin (Leica, Surgipath). Liver macrophages were stained using rat anti-mouse F4/80 antigen (Serotec), followed by anti-Rat HRP (Histofine) and developed with a DAB kit (Zymed). Liver sections were stained for Masson Trichrome (Sigma). Liver CD3+ T cells were stained using Rat anti human-CD3-antibody (Bio-Rad), followed by anti-Rat HRP (Histofine) and developed with AEC (Invitrogen). α-SMA positive cells were stained using mouse anti-Human smooth Muscle Actin antibody (Dako), followed by anti-mouse HRP (Dako) and developed with DAB. The percentage area stained positively per high power field was calculated by ImageJ Software in 5-10 random fields.

Statistical Analysis

Data were subjected to statistical analysis using the Excel software package (Microsoft, Redmond, WA) or GraphPad Prism6 (GraphPad Software Inc., La Jolla, CA). Two-tailed Student t tests, and Pearson and Spearman correlation coefficients were used to determine the difference between the groups. Data are given as mean±SD, and are shown as error bars for all experiments. Differences were considered significant at $P<0.05$. The reported data were obtained from at least 3 biological replicates.

TABLE 1

Primers used for Real-Time-PCR

| Primer Number | Direction | Sequence (5' to 3') |
|---|---|---|
| Mouse DGAT1 | Forward | GTGGTTTCAGCAATTATCGTGG |
| | Reverse | GGGTCCTTCAGAAACAGAGAC |
| Mouse HPRT | Forward | GCGATGATGAACCAGGTTATGA |
| | Reverse | ATCTCGAGCAAGTCTTTCAGTCCT |
| Mouse pri-miR-122 | Forward | TTCGGGAACTATGTGGAGTCACTT TG |
| | Reverse | CGCAAGGCTGCCCTCAAACCCTCA G |
| Mouse pre-miR-122 | Forward | CCATCAAACGCCATTATCACACTA |
| | Reverse | CACACAATGGAGAACTCTAGCACA A |
| Mouse ALDOA | Forward | GGGTGATCCTCTTCCACGAGA |
| | Reverse | AGGGGCACCACACCCTTATC |
| Mouse AGPATI | Forward | GGGCGCAATGTCGAGAACATG |
| | Reverse | CTGGCAGGACCTCCATCATTC |
| Mouse CPT1α | Forward | AGACAAGAACCCCAACATCC |
| | Reverse | CAAAGGTGTCAAATGGGAAGG |
| Mouse TGFBR2 | Forward | CAAGTTTTGCGATGTGAGACTG |
| | Reverse | CCGTCTCCAGAGTAATGTTCTTG |
| Mouse TGFB2 | Forward | CTCTGTGGGTACCTTGATGCC |
| | Reverse | GGAAGACCCTGAACTCTGCC |
| Mouse FGF21 | Forward | CAAATCCTGGGTGTCAAAGC |
| | Reverse | CATGGGCTTCAGACTGGTAC |
| Mouse IFNβ | Forward | TCCGAGCAGAGATCTTCAGGAA |
| | Reverse | TGCAACCACCACTCATTCTGAG |
| mouse ACTA2 (alpha sma) | Forward | GTGAAGAGGAAGACAGCACAG |
| | Reverse | GCCCATTCCAACCATTACTCC |
| Mouse RORα | Forward | CATGGTTCCTAAGGGATGAGAG |
| | Reverse | CATGGTTCCTAAGGGATGAGAG |
| Mouse ADGRE1 (F4/80) | Forward | CCCCAGTGTCCTTACAGAGTG |
| | Reverse | GTGCCCAGAGTGGATGTCT |
| Mouse COLA1 | Forward | CATAAAGGGTCATCGTGGCT |
| | Reverse | TTGAGTCCGTCTTTGCCAG |
| Mouse COL3A1 | Forward | GAAGTCTCTGAAGCTGATGGG |
| | Reverse | TTGCCTTGCGTGTTTGATATTC |

TABLE 1-continued

Primers used for Real-Time-PCR

| Primer Number | Direction | Sequence (5' to 3') |
|---|---|---|
| Mouse G6PC | Forward | TCACTTCTACTCTTGCTATCTTTCG |
|  | Reverse | CCCAGAATCCCAACCACAAG |
| Mouse TNFα | Forward | CTGTAGCCCACGTCGTAGCAA |
|  | Reverse | CTGGCACCACTAGTTGGTTGT |
| miR-122 | Forward | TGGAGTGTGACAATGGTGTTTG |
| miR-34 | Forward | TGGCAGTGTCTTAGCTGGTTGT |
| miR-18a | Forward | TAAGGTGCATCTAGTGCAGATAG |
| miR-21 | Forward | TAGCTTATCAGACTGATGTTGA |
| miR-126-5p | Forward | CATTATTACTTTTGGTACGCG |
| miR-93-5p | Forward | CAAAGTGCTGTTCGTGCAGGTAG |
| RNU-6 | Forward | CGCAAGGATGACACGCAAATTC |
| Cel-miR-39-3P | Forward | TCACCGGGTGTAAATCAGCTTG |

TABLE 2 antagomiR sequences used in the study.

| Name | Sequence |
|---|---|
| antagomiR-122 | 5'-mAsmCsmAmAmAmCmAmCm CmAmUmUmGmUmCmAmCmAmCm UsmCsmCsmAs-Chol-3' |
| antagomiR-control | 5'-mCsmAsmCmCmAmCmAmUm AmCmCmGmCmAsmCsmGsmGs-Chol-3' |

All the oligonucleotides were synthesized by IDT (IDT, Coralville, IA, USA). Chemical modifications of the antisense oligos: Subscript 'm' represent 2'-O Me-modified nucleotides; Subscript 's' represents a phosphorothioate linkage; 'Chol' represents cholesterol linked through a hydroxyprolinol linkage.

TABLE 3

Normal and Atherogenic diet compositions.

|  | Normal Diet (gr/kg) | Atherogenic Diet (gr/kg) |
|---|---|---|
| cornstarch | 397.5 | 397.5 |
| maltodextrin | 132.0 | 132.0 |
| sucrose | 100.0 | 100.0 |
| casein | 200.0 | 200.0 |
| soybean oil | 70.0 | 70.0 |
| cellulose | 50.0 | 50.0 |
| mineral mix | 35.0 | 35.0 |
| vitamin mix | 10.0 | 10.0 |
| L-methionine | 3.0 | 3.0 |
| Choline bitartrate | 2.5 | 2.5 |
| BTH | 0.014 | 0.014 |
| Cholesterol | 0.0 | 10.0 |
| Cholic Acid | 0.0 | 5.0 |
| total weight | 1000.0 | 1015.0 |

REFERENCES

1. Chai, C. et al. Metabolic Circuit Involving Free Fatty Acids, microRNA 122, and Triglyceride Synthesis in Liver and Muscle Tissues. Gastroenterology 153, 1404-1415 (2017).
2. Rivkin, M. et al. Inflammation-Induced Expression and Secretion of MicroRNA 122 Leads to Reduced Blood Levels of Kidney-derived Erythropoietin and Anemia. Gastroenterology (2016). doi:10.1053/j.gastro.2016.07.031
3. Kondratov, K. et al. Heparinase treatment of heparin-contaminated plasma from coronary artery bypass grafting patients enables reliable quantification of microRNAs. Biomol. Detect. Quantif. 8, 9-14 (2016).
4. Izraeli, S., Pfleiderer, C. & Lion, T. Detection of gene expression by PCR amplification of RNA derived from frozen heparinized whole blood. Nucleic Acids Res. 19, 6051 (1991).

Example 10

Demonstration that Compound 1 Acts as a Potent RORα Agonist and Improves Triglyceride Levels in a Mouse Model of NASH.

Experimental design: C57BL/6 mice fed for 6 weeks with high fat diet (HFD) were injected with 15 mg/kg Compound 1 (or saline+DMSO) 3 times a week for 3 weeks (n=6).

FIGS. 7 A and B show the results of qRT-PCR analysis of miR-122 extracted from plasma and liver, respectively, in mice treated with Compound 1 or saline. FIG. 7C shows the qRT-PCR analysis of RORα target genes, pri- and pre-miR-122 mRNA, extracted from mice livers. FIG. 7D is a chart showing the quantification of liver triglyceride (TG) levels.

Treatment with Compound 1 induced expression and secretion of miR-122 and precursors in the plasma and liver. Additionally, treatment with Compound 1 significantly induced expression of RORα-regulated genes FGF21 and Gpase6. Treatment with Compound 1 decreased triglyceride levels by 5-fold compared to untreated HFD mice.

Example 11

The RORα Agonist, Compound 1, Improves Body Weight and Hepatic Lipid Accumulation in a Mouse Mode of NASH.

Experimental design: C57BL/6 mice fed for 6 weeks with HFD were injected with 15 mg/kg Compound 1 (or saline+DMSO) 3 times a week for 3 weeks (n=6).

Figure 8C:
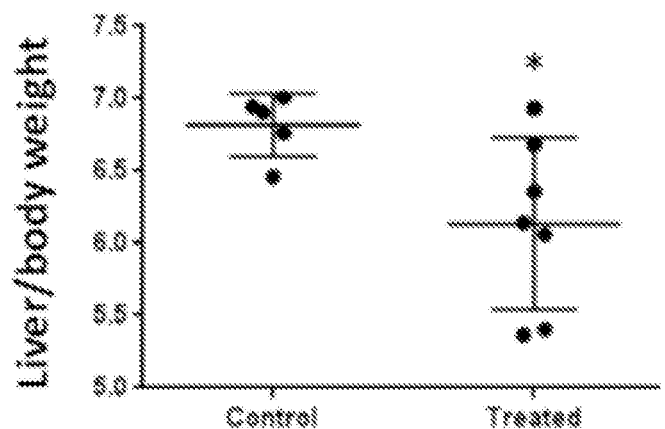
FIG. 8C is a chart showing shows the liver/body weight ratio (%) measured at the end of the experiment.
Figure 9A:
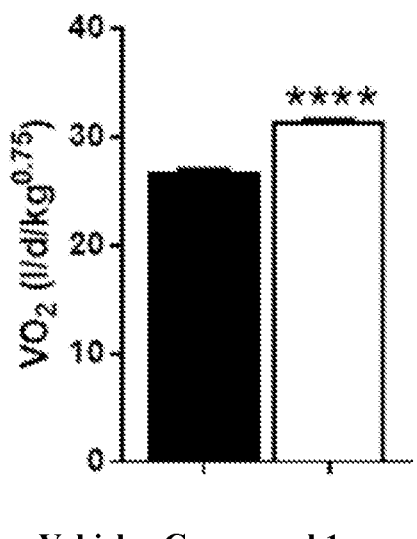
FIG. 9A compares volume 02 in vehicle vs Compound 1-treated mice ($1/d/kg^{0.75}$) FIG. 9B compares volume $CO_2$ in vehicle vs Compound 1-treated mice ($1/d/kg^{0.75}$).
Figure 9B:
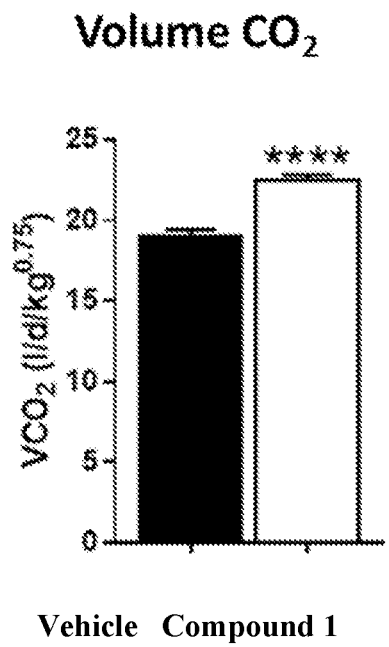
FIGS. 9 A-E are charts showing the change in metabolic output in a mouse model when C57BL/6 mice are administered Compound 1 or control (saline+DMSO) over a 24 hr period.
FIG. 9C compares total energy expenditure in vehicle vs Compound 1-treated mice ($Kcal/h/kg^{0.75}$) FIG. 9D compares fat oxidation in vehicle vs Compound 1-treated mice ($g/d/kg^{0.75}$).
FIG. 9E compares carbohydrate oxidation in vehicle vs Compound 1-treated mice ($g/d/kg^{0.75}$) Effective mass was calculated by power of 0.75. Data are mean±SEM from 8 mice per group.
Figure 9C:
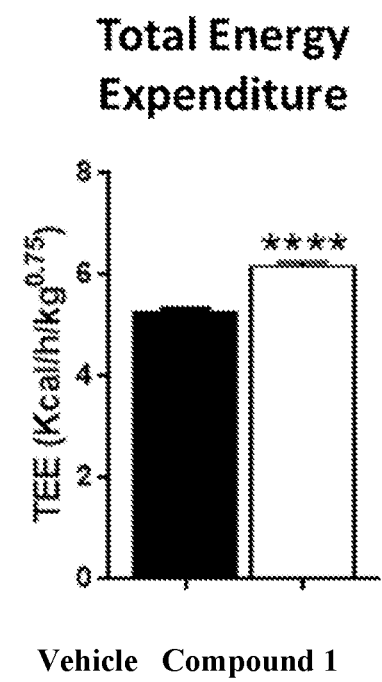
Figure 9D:
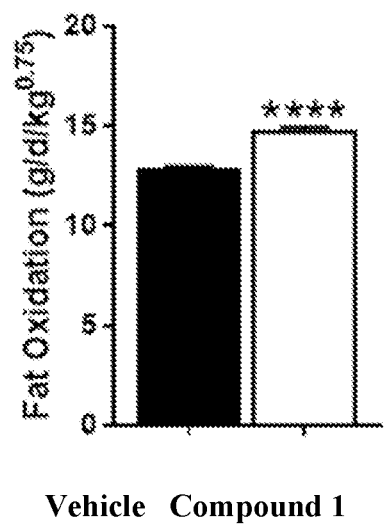
Figure 9E:
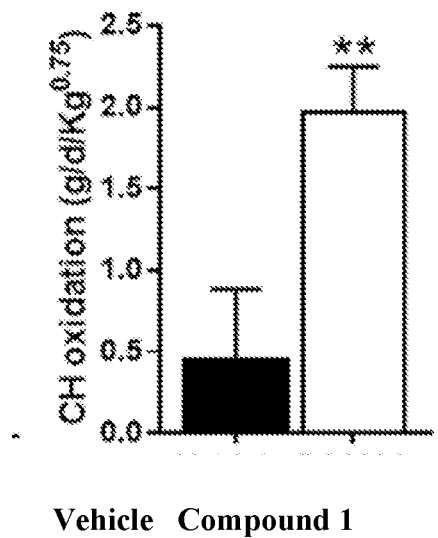

FIG. 8A shows the body weight measured during the experiment. FIG. 8B shows liver H&E staining, and FIG. 8C shows the liver/body weight ratio (%) measured at the end of the experiment. Control mice (antagomiR-control once a week and DMSO diluted in saline twice a week) had a steady increase in weight. Mice in which an antagomir-122 was administered had the highest increase in weight. Those treated with the RORα agonist Compound 1, their weight steadily decreased and lost weight. Mice administered both antagomir-122 and Compound 1 had their weight returned to exactly that of controls animals. This phenomenon suggests that miR-122 and Compound 1 likely antagonize one another. Furthermore, it also indicated that the reduction in weight is not due to a toxic effect. At cessation of the experiment, there was a significant increase in weight in the antagomiR-122 treated animals, indicating that a reduction in miR-122 in the liver is associated with a systemic effect, whereas the administration of Compound 1 significantly reduced weight at end of experiment. The liver was further analyzed to assess lipotoxicity. Hepatic lipid droplets were reduced in Compound 1-treated mice, and this reduction was completely abolished in antatagomiR-122 injected mice, suggesting that the beneficial effect of Compound 1 on steatosis is mediated by miR-122 activity. Accordingly, there was a decrease in the liver/body weight ratio in the treated group compared to the untreated group.

Example 12

The RORα Agonist, Compound 1, Improves Metabolic Output in a Mouse Mode of NASH.

Experimental design: C57BL/6 mice fed for 6 weeks with HFD were injected with 15 mg/kg Compound 1 (or saline+DMSO) 3 times a week for 3 weeks (n=8). Metabolic cages: After 2 weeks of Compound 1 or saline treatment, mice were monitored by the Promethion High-Definition Behavioral Phenotyping System (Sable Instruments, Inc.) over a 24 hr period.

The results are shown in FIGS. 9 A-E, which are charts showing the change in metabolic output in a mouse model when C57BL/6 mice are administered Compound 1 or control (saline+DMSO) over a 24 hr period. FIG. 9A compares volume $O_2$ in vehicle vs Compound 1-treated mice ($1/d/kg^{0.75}$). FIG. 9B compares volume $CO_2$ in vehicle vs Compound 1-treated mice ($1/d/kg^{0.75}$). FIG. 9C compares total energy expenditure in vehicle vs Compound 1-treated mice ($Kcal/h/kg^{0.75}$). FIG. 9D compares fat oxidation in vehicle vs Compound 1-treated mice ($g/d/kg^{0.75}$). FIG. 9E compares carbohydrate oxidation in vehicle vs Compound 1-treated mice ($g/d/kg^{0.75}$)

Note an increased total energy expenditure (TEE; J); and fat oxidation (K) in the Compound 1-treated mice in comparison with saline (vehicle) treated animals. Effective mass was calculated by power of 0.75. Data are mean±SEM from 8 mice per group.

Example 13

The RORα Agonist, Compound 1, Restores Insulin Sensitivity in a Mouse Mode of NASH.

Experimental design: C57BL/6 mice fed for 6 weeks with HFD were injected with 15 mg/kg Compound 1 (or saline+DMSO) 3 times a week for 3 weeks (n=6). Whole-blood glucose levels during an insulin tolerance test (ITT) in HFD fed Compound 1-treated mice vs. HFD-fed saline-treated mice and normal-diet fed mice (control ND); minutes indicate time after insulin injection. N.s.=not significant.

Figure 10:
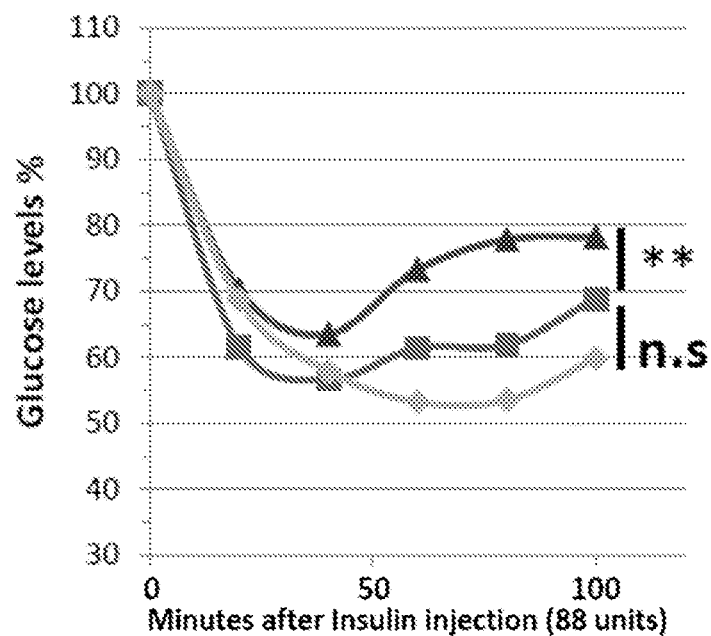
FIG. 10 is a chart showing glucose levels (% versus minutes) after insulin injection (88 units) in C57BL/6 mice fed for 6 weeks with HFD, and injected with 15 mg/kg Compound 1 (red) vs. HFD-fed saline-treated (blue) mice and normal-diet fed mice (control ND, green); minutes indicate time after insulin injection. n.s.=not significant.
Figure 11A:
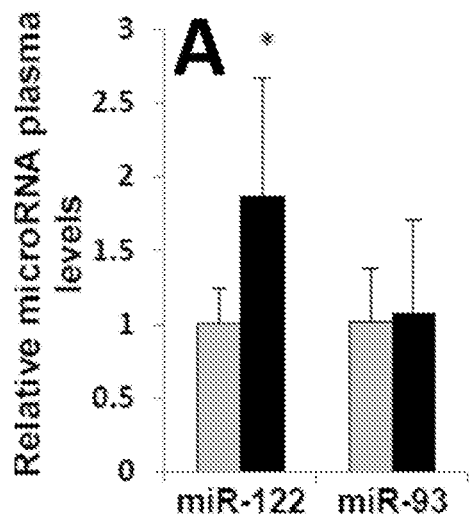
FIGS. 11A-D are charts showing various markers of liver damage in C57BL/6 mice fed for 3 weeks with an atherogenic diet (to induce fibrosis) and injected with 15 mg/kg Compound 1 (or saline+DMSO) 3 times a week for 3.5 weeks (n=8). qRT-PCR analysis of miR-122 extracted from plasma (FIG. 11A) and liver (FIG. 11B) for the untreated (grey bars) and treated (black bars) cohorts. miR-93 and miR-18 were included for negative controls in plasma and liver, respectively.
Figure 11B:
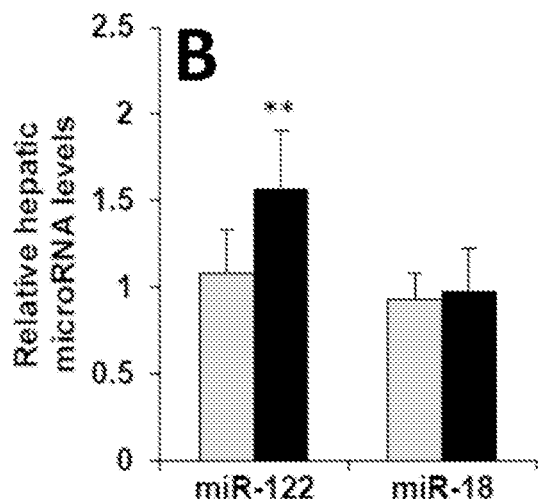
Figure 11C:
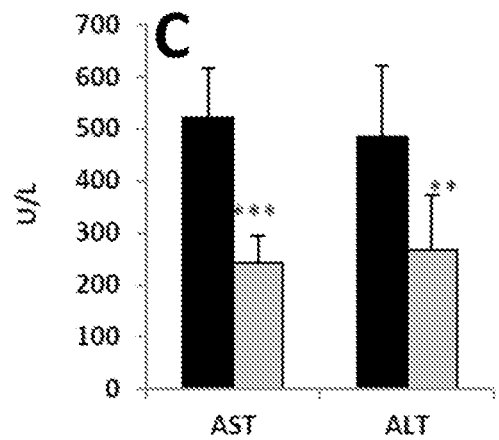
Figure 11D:
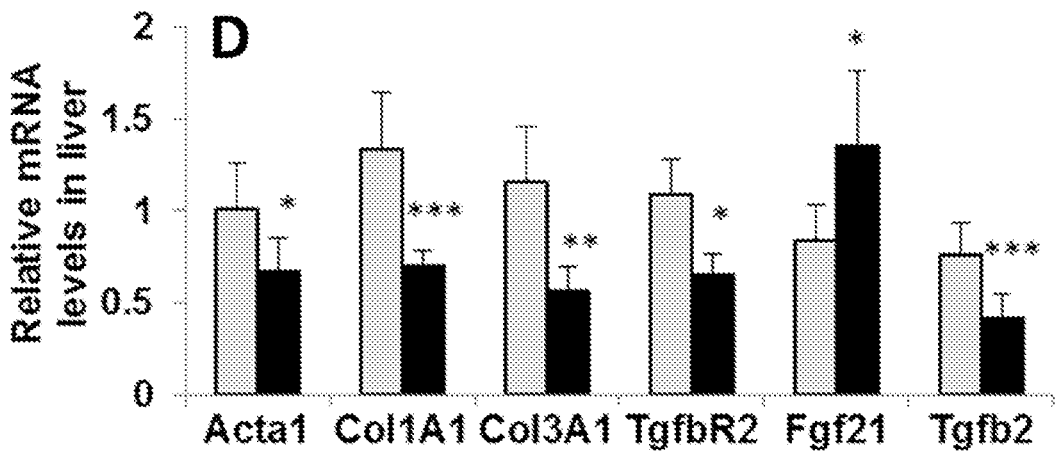

The results are shown in FIG. 10. In mice fed a normal diet, blood glucose levels dropped to approximately 55% after 55 minutes and returned to 60% after 100 minutes. The HFD cohort had an initial drop in blood glucose levels to approximately 65% and rebounded to 80% after 100 minutes. The compound 1 treated cohort exhibited an initial decrease in blood glucose to ~55% after 45 minutes post-injection, which then returned to 70% after 100 minutes. These results demonstrate that Compound 1 improves insulin sensitivity compared to the untreated cohort.

Example 14

The RORα Agonist, Compound 1, Improves Markers of Liver Damage and Fibrosis in a Fibrotic Diet Mouse Model.

Experimental design: C57BL/6 mice fed for 3 weeks with atherogenic diet (to induce fibrosis) and injected with 15 mg/kg Compound 1 (or saline+DMSO) 3 times a week for 3.5 week (n=8).

The results are shown in FIGS. 11A-D. qRT-PCR analysis of miR-122 extracted from A) plasma and B) from liver for the untreated (grey bars) and treated (black bars) cohorts. miR-93 and miR-18 were included for negative controls in plasma and liver, respectively. C) ALT and AST plasma levels measured at the end of the experiment. D) qRT-PCR analysis of mRNA of genes involved in fibrosis and RORα target gene (Fgf21) extracted from mice livers. microRNA levels in the plasma were normalized to spiked *C. elegans* miR-39; microRNA levels in the tissues were normalized to RNU6. mRNA levels were normalized to HPRT. Data are presented as error bars=SD. *P<0.05, P<0.01. *P<0.001, ****P<0.0001.

Once it was observed that the RORα activator Compound 1 has significant anti-lipotoxic properties in the liver and remote tissues, reduces weight and has beneficial metabolic properties, we were encouraged to determine the effects of Compound 1 on liver inflammation and fibrosis. The effects of Compound 1 on liver inflammation and fibrosis in the mouse atherogenic diet model have been assessed. After liver inflammation and fibrosis developed at week 3 of diet, animals initiated to receive Compound 1. After 3.5 additional weeks, in which animals received 3 times weekly Compound 1, animals were assessed for numerous endpoints. We confirmed that mature miR-122 increased both in tissue and in plasma following the administration of Compound 1. Treatment with Compound 1 significantly improved biomarkers of liver injury, AST and ALT, in addition to reducing biomarkers of inflammation (Tgfb2 and TgfbR2) and fibrosis (Acta1, Col1A1 and Col3A1).

Example 15

The RORα Agonist, Compound 1, Improves Hepatic Inflammatory Profiles in a Fibrotic Diet Mouse Model.

Figure 12A:
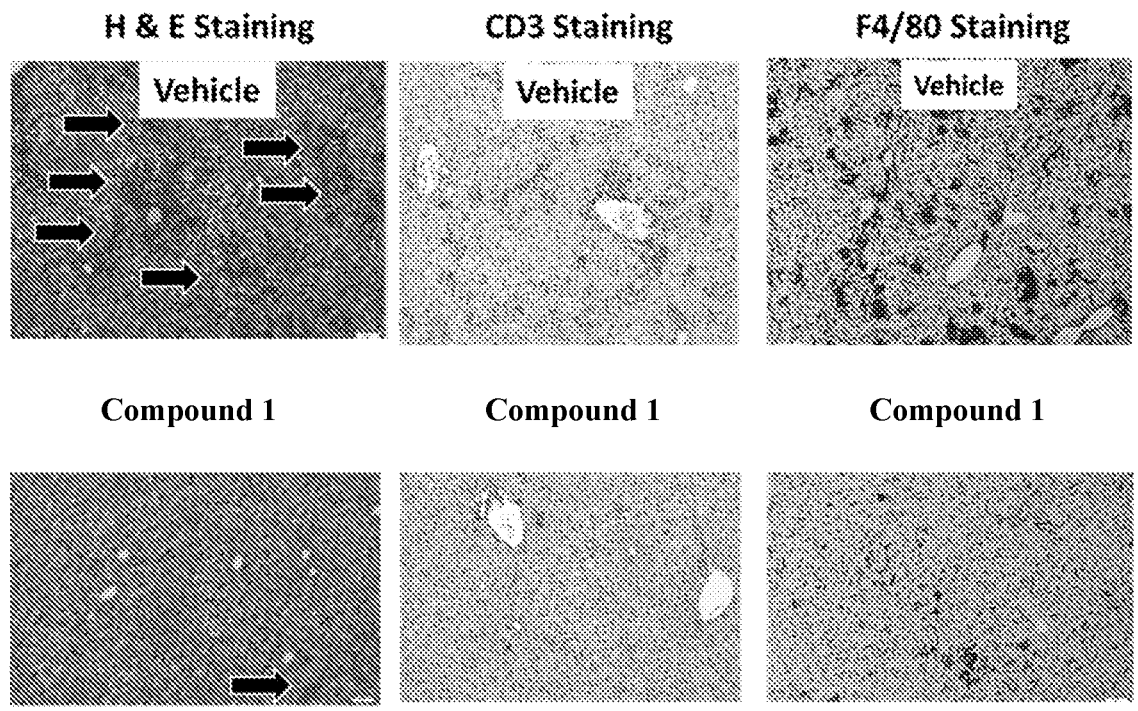
FIG. 12A shows representative microphotographs of H&E, CD3 and F4/80-stained livers taken from saline or Compound 1-treated mice; scale bars represent 10 μm.
Figure 12B:
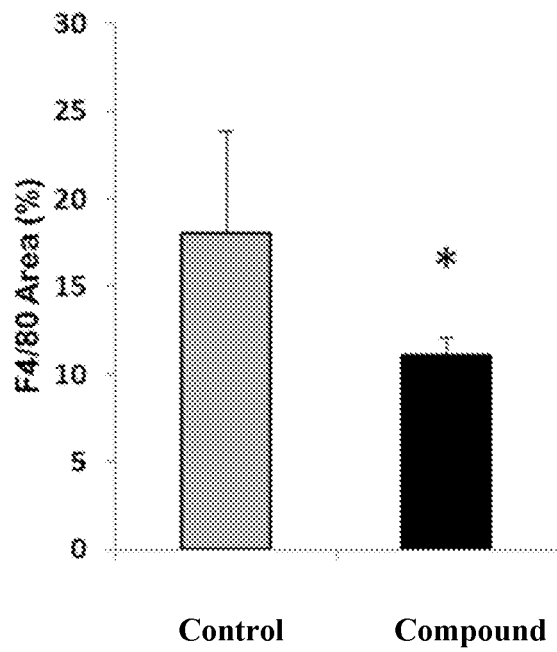
FIG. 12B is a chart showing quantification of positively-stained F4/80 areas using ImageJ.
Figure 13C:
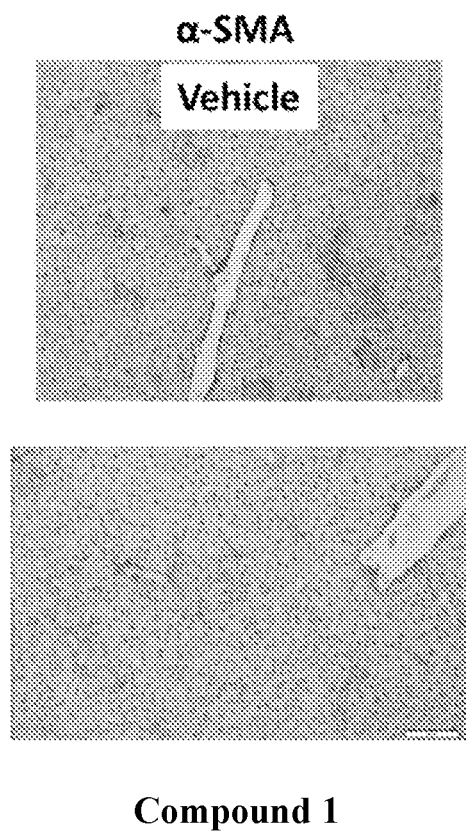
FIGS. 13 A and C are microphotographs of Masson Trichrome (M.T.) and α-SMA stained livers taken from saline or Compound 1-treated mice; scale bars represent 10 μm.
FIGS. 13B and D are graphs showing quantification of positively-stained areas using ImageJ (%). M.T. staining is shown in FIG. 13B and SMA staining is shown in FIG. 13D.
Figure 13D:
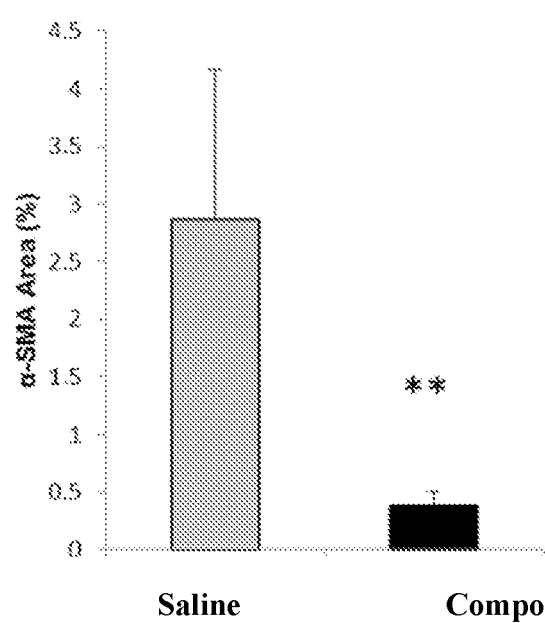

Experimental design: C57BL/6 mice fed for 3 weeks with atherogenic diet (to induce fibrosis) and injected with 15 mg/kg Compound 1 (or saline+DMSO) 3 times a week for 3.5 week (n=8). Representative microphotographs of H&E, CD3, and F4/80-stained livers taken from saline or Compound 1-treated mice are shown in FIG. 12A, where scale bars represent 10 μm. The graphs shown in FIG. 12B show quantification of positively-stained F4/80 areas using ImageJ.

Compound 1-treated mice showed decreased immune infiltrate by H&E staining, decreased T-cell density by CD3 staining and decreased levels of myeloid infiltrate by F4/80 staining. These results demonstrated that Compound 1 exhibits anti-inflammatory effects.

Example 16

The RORα Agonist, Compound 1, Decreases Hepatic Fibrosis in a Fibrotic Diet Mouse Model.

Experimental design: C57BL/6 mice fed for 3 weeks with atherogenic diet (to induce fibrosis) and injected with 15 mg/kg Compound 1 (or saline+DMSO) 3 times a week for 3.5 week (n=8). Results are shown in FIGS. 13A-D.

FIGS. 13A and C are representative microphotographs of Masson Trichrome (M.T.) and α-SMA stained livers taken from saline or Compound 1-treated mice, where scale bars represent 10 μm. FIGS. 13B and D are graphs showing the quantification of positively-stained areas using ImageJ.

Two stains were utilized to evaluate the effects of Compound 1 on liver fibrosis (Masson Trichrome and α-SMA). The untreated cohort exhibited large positive areas using both staining methods, and treatment with compound 1 significantly reduced the fibrotic areas by 5-fold (M.T) and 7-fold (α-SMA). These observations strongly support that Compound 1 exhibits anti-fibrotic activity in this mouse model.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

We claim:

1. A method for treatment of disease selected from the group consisting of non-alcoholic steatohepatitis (NASH), alcoholic steatohepatitis (ASH), non-alcoholic fatty liver disease (NAFLD) comprising administering an effective treatment amount of a compound of Formula A to a patient in need of treatment thereof,

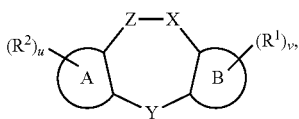

Formula (A)

wherein:
wherein Z is C(O), and X and Y are selected from the group consisting of —NH—, —N(NH$_2$)—, —NH(OH)—, N(C$_{1-10}$ alkyl)-, —N(C$_{3-10}$ cycloalkyl)-, —N(C$_{2-10}$ alkenyl)-, —N(C$_{2-10}$ alkynyl)-, —N(aryl)-, or —N(heteroaryl)

A and B are phenyl;

u and v are independently 0, 1, 2, 3 or 4; with the proviso that at least one of u and v is 1, 2, 3, or 4;

each R$^1$ and R$^2$ are independently R$^3$, OH, OR$^3$, SR$^3$, S(O)R$^3$, SO$_2$R$^3$, C(O)R$^3$, C(O)OR$^3$, OC(O)R$^3$, OC(O)OR$^3$, NH$_2$, NHR$^3$, NHC(O)R$^3$, NR$^3$C(O)R$^3$, NHS(O)$_2$R$^3$, NR$^3$S(O)$_2$R$^3$, NHC(O)OR$^3$, NR$^3$C(O)OR$^3$, NHC(O)NH$_2$, NHC(O)NHR$^3$, NHC(O)N(R$^3$)$_2$, NR$^3$C(O)N(R$^3$)$_2$, C(O)NH$_2$, C(O)NHR$^3$, C(O)N(R$^3$)$_2$, C(O)NHOH, C(O)NHOR$^3$, C(O)NHSO$_2$R$^3$, C(O)NR$^3$SO$_2$R$^3$, SO$_2$NH$_2$, SO$_2$NHR$^3$, SO$_2$N(R$^3$)$_2$, COOH, C(O)H, C(N)NH$_2$, C(N)NHR$^3$, C(N)N(R$^3$)$_2$, C(N)OH, C(N)OCH$_3$, CN, N$_3$, NO$_2$, CF$_3$, CF$_2$CF$_3$, OCF$_3$, OCF$_2$CF$_3$, halo (F, Cl, Br, or I), —CH$_2$-phosphonate, —CH$_2$O-phosphate, CH$_2$P(O)(OH)$_2$, CH$_2$P(O)(OR$^3$)$_2$, CH$_2$P(O)(OR$^3$)(NR$^3$), CH$_2$P(O)(NR$^3$)$_2$, CH$_2$P(O)(OH)(OC$_{1-10}$ alkyl-O—C$_{1-20}$ alkyl), or CH$_2$-cycloSal monophosphate prodrug, wherein the term phosphate includes monophosphate, diphosphate, triphosphate, and stabilized phosphate prodrugs, and the term phosphonate includes the same prodrugs that are present in the phosphate prodrugs, and when R$^1$ and R$^2$ are on adjacent carbon, they can come together to form an saturated or unsaturated alkyl, an aromatic or a heteroaromatic ring each R$^3$ is, independently, aryl, heteroaryl, C$_{3-10}$ cycloalkyl, C$_{3-10}$ cycloalkenyl, heterocycloalkyl, heterocycloalkenyl, C$_{1-10}$ alkyl, C$_{2-10}$ alkenyl or C$_{2-10}$ alkynyl, each of which is unsubstituted or independently substituted with one or more substituents selected from the group consisting of R$^4$, OH, OR$^4$, SR$^4$, S(O)R$^4$, SO$_2$R$^4$, C(O)R$^4$, C(O)OR$^4$, OC(O)R$^4$, OC(O)OR$^4$, NH$_2$, NHR$^4$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, COOH, C(O)H, C(N)NH$_2$, C(N)NHR$^4$, C(N)N(R$^4$)$_2$, C(N)OH, C(N)OCH$_4$, CN, N$_3$, NO$_2$, CF$_3$, CF$_2$CF$_3$, OCF$_3$, OCF$_2$CF$_3$, halo (F, Cl, Br, or I), P(O)(OH)$_2$, P(O)(OR$^4$)$_2$, P(O)(OR$^4$)(NR$^4$), P(O)(NR$^4$)$_2$, P(O)(OH)(OC$_{1-10}$ alkyl-O—C$_{1-20}$ alkyl), cycloSal monophosphate prodrugs, CH$_2$P(O)(OH)$_2$, CH$_2$P(O)(OR$^4$)$_2$, CH$_2$P(O)(OR$^4$)(NR$^4$), CH$_2$P(O)(NR$^4$)$_2$, CH$_2$P(O)(OH)(OC$_{1-10}$ alkyl-O—C$_{1-20}$ alkyl), and CH$_2$-cycloSal monophosphate prodrugs, each R$^4$ are independently selected from aryl, heteroaryl, arylalkyl, alkylaryl, C$_{3-10}$ cycloalkyl, C$_{3-10}$ cycloalkenyl, heterocycloalkyl, heterocycloalkenyl, C$_{1-10}$ alkyl, C$_{2-10}$ alkenyl or C$_{2-10}$ alkynyl, each of which is unsubstituted or independently substituted with one or more substituents selected from the group consisting of R$^5$, OH, OR$^5$, SR$^5$, S(O)R$^5$, SO$_2$R$^5$, C(O)R$^5$, C(O)OR$^5$, OC(O)R$^5$, OC(O)OR$^5$, NH$_2$, NHR$^5$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR⁵, NHC(O)N(R⁵)₂, NR⁵C(O)N(R⁵)₂, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, COOH, C(O)H, C(N)NH₂, C(N)NHR⁵, C(N)N(R⁵)₂, C(N)OH, C(N)OCH₃, CN, N₃, NO₂, CF₃, CF₂CF₃, OCF₃, OCF₂CF₃, halo (F, Cl, Br, or I), P(O)(OH)₂, P(O)(OR⁴)₂, P(O)(OR⁴)(NR⁴), P(O)(NR⁴)₂, P(O)(OH)(OC$_{1-10}$ alkyl-O—C$_{1-20}$ alkyl), and cycloSal monophosphate prodrugs, each R⁵ are independently aryl, heteroaryl, C$_{3-10}$ cycloalkyl, C$_{3-10}$ cycloalkenyl, heterocycloalkyl, heterocycloalkenyl, C$_{1-10}$ alkyl, C$_{2-10}$ alkenyl or C$_{2-10}$ alkynyl, each of which is unsubstituted or independently substituted with one or more substituents selected from the group consisting of R⁶, OH, OR⁶, SR⁶, S(O)R⁶, SO₂R⁶, C(O)R⁶, C(O)OR⁶, OC(O)R⁶, OC(O)OR⁶, NH₂, NHR⁶, NHC(O)R⁶, NR⁶C(O)R⁶, NHS(O)₂R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C(O)N(R⁶)₂, C(O)NH₂, C(O)NHR⁶, C(O)N(R⁶)₂, C(O)NHOH, C(O)NHOR⁶, C(O)NHSO₂R⁶, C(O)NR⁶SO₂R⁶, SO₂NH₂, SO₂NHR⁶, SO₂N(R⁶)₂, COOH, C(O)H, C(N)NH₂, C(N)NHR⁶, C(N)N(R⁶)₂, C(N)OH, C(N)OCH₃, CN, N₃, NO₂, CF₃, CF₂CF₃, OCF₃, OCF₂CF₃, F, Cl, Br, I, P(O)(OH)₂, P(O)(OR⁴)₂, P(O)(OR⁴)(NR⁴), P(O)(NR⁴)₂, P(O)(OH)(OC$_{1-10}$ alkyl-O—C$_{1-20}$ alkyl), and cycloSal monophosphate prodrugs, each R⁶ are independently aryl, heteroaryl, C$_{3-10}$ cycloalkyl, C$_{3-10}$ cycloalkenyl, heterocycloalkyl, heterocycloalkenyl, C$_{1-10}$ alkyl, C$_{2-10}$ alkenyl or C$_{2-10}$ alkynyl, each of which is unsubstituted or independently substituted with one or more substituents selected from the group consisting of C$_{1-10}$ alkyl, C$_{2-10}$ alkenyl, C$_{2-10}$ alkynyl, OH, NH₂, C(O)NH₂, C(O)NHOH, SO₂NH₂, COOH, C(O)H, C(N)NH₂, C(N)OH, C(N)OCH₃, CN, N₃, NO₂, CF₃, CF₂CF₃, OCF₃, OCF₂CF₃, halo (F, Cl, Br, or I), P(O)(OH)₂, P(O)(OR⁴)₂, P(O)(OR⁴)(NR⁴), P(O)(NR⁴)₂, P(O)(OH)(OC$_{1-10}$ alkyl-O—C$_{1-20}$ alkyl), and cycloSal monophosphate prodrugs, or a pharmaceutically-acceptable salt thereof.

2. The method of claim 1, wherein the compound(s) are administered in combination or alternation with a second therapeutic agent.

3. The method of claim 2, wherein the second therapeutic agent is an agent used to treat metabolic disorders.

4. The method of claim 3, wherein the active agent is an anti-diabetic or anti-insulin resistance agent.

5. The method of claim 4, wherein the anti-diabetic or anti-insulin resistance agent is selected from the group consisting of a glitazone, a sulfonylurea, metformin, insulin, an insulin mimetic, a DPP4 inhibitor, a GLP1 receptor agonist, a glucagon receptor antagonist, and an anti-obesity agent.

6. The method of claim 3, wherein the additional active agent is selected from the group consisting of cholesterol biosynthesis inhibitors, squalene epoxidase inhibitors; plasma HDL-raising agents; human peroxisome proliferator activated receptor (PPAR) gamma agonists; PPAR alpha agonists; PPAR dual alpha/gamma agonists; farnesoid X receptor (FXR) modulators; bile acid sequestrants; bile acid transport inhibitors; nicotinic acid, niacinamide; cholesterol absorption inhibitors; acyl-coenzyme A: cholesterol O-acyl transferase (ACAT) inhibitors; selective estrogen receptor modulators; LXR alpha or beta agonists, antagonists or partial agonists; microsomal triglyceride transfer protein (MTP) inhibitors, anti-diabetes agents; SGLT-2 inhibitors, sergliflozin, AVE 2268; Glucokinase activators; anti-obesity agents, growth hormone agonists, adrenergic uptake inhibitors, serotonin reuptake/transporter inhibitors, 5-HT/NA (serotonin/noradrenaline) reuptake inhibitors, dopamine reuptake inhibitors, 5-HT, NA and DA reuptake blockers, steroidal plant extracts, NPY1 or 5 (neuropeptide Y1 or Y5) antagonists, NPY2 (neuropeptide Y2) agonists, MC4 (melanocortin 4) agonists, CCK-A (cholecystokinin-A) agonists, GHSR1a (growth hormone secretagogue receptor) antagonist/inverse agonists, ghrelin antibody, MCH1R (melanin concentrating hormone 1R) antagonists, MCH2R (melanin concentrating hormone 2R) agonist/antagonists, H3 (histamine receptor 3) inverse agonists or antagonists, H1 (histamine 1 receptor) agonists, FAS (Fatty acid synthase) inhibitors, ACC-1 (acetyl-CoA carboxylase-1) inhibitors, β3 (beta adrenergic receptor 3) agonists, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1, 2 or 3 (uncoupling protein-1, 2 or 3) activators, leptin, leptin derivatives, opioid antagonists, orexin antagonists, BRS3 agonists, GLP-1 (glucagons-like peptide-1) agonists, IL-6 agonists, a-MSH agonists, AgRP antagonists, BRS3 (bombesin receptor subtype 3) agonists, 5-HT1B agonists, POMC antagonists, ciliary neurotrophic factor, NN2211, Topiramate, glucocorticoid antagonist, Exendin-4 agonists, serotonin receptor 2C agonists, phosphodiesterase inhibitors, fatty acid transporter inhibitors, dicarboxylate transporter inhibitors, glucose transporter inhibitors, cannabinoid-1 receptor inverse agonists or antagonists, lipase inhibitors; vitamin B6 and pharmaceutically acceptable salts thereof; vitamin B 12; folic acid or a pharmaceutically acceptable salt or ester thereof.

7. The method of claim 3, wherein the additional active agent is an agent that modifies host metabolism.

8. The method of claim 1, wherein one of R¹ and R² is H, —CH₂-phosphonate, —CH₂O-phosphate, wherein the term phosphate includes monophosphate, diphosphate, triphosphate, and stabilized phosphate prodrugs, and the term phosphonate includes the same prodrugs that are present in the phosphate prodrugs.

9. The method of claim 1, wherein one of R¹ and R² is H, —CH₂P(O)(OH)₂, —CH₂P(O)(OH)(OR⁶), —CH₂P(O)(OR⁶)₂, —CH₂P(O)(OR⁶)(NR⁶), —CH₂P(O)(NR⁶)₂, —CH₂P(O)(OH)(OC$_{1-10}$ alkyl-O—C$_{1-20}$ alkyl), or a —CH₂-cycloSal monophosphate prodrug.

10. The method of claim 9, wherein one of R¹ and R² is a phosphonate, a phosphoramidate, a cycloSal monophosphate prodrug, or has the formula —CH₂P(O)(OH)(OC$_{1-10}$ alkyl-O—C$_{1-20}$ alkyl).

11. The method of claim 1, wherein one of R¹ and R² is C(O)NHR⁴, C(O)(NR⁴)₂,

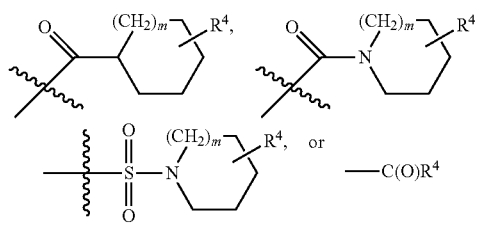

wherein R⁴ is C$_{1-10}$ alkyl, C$_{3-10}$ cycloalkyl, C$_{2-10}$ alkenyl, C$_{2-10}$ alkynyl, C$_{1-10}$ halo alkyl, C$_{1-10}$ alkyl-aryl, or C$_{1-10}$ haloalkyl-aryl and m is 0, 1 or 2.

12. The method of claim 1, wherein one of $R^1$ and $R^2$ is —C(O)—$C_{1-10}$ alkyl, —C(O)-alkylaryl, —C(O)-heterocyclyl-alkylaryl, —C(O)-heterocyclyl-CH$_2$-aryl, —C(O)-heterocyclyl-CF$_2$-aryl, —C(O)-cycloalkyl-alkylaryl, —C(O)NHC$_{1-10}$ alkyl, —C(O)NH-alkylaryl, —C(O)NH-heterocyclyl-alkylaryl, —C(O)NH-heterocyclyl-CF$_2$-aryl, —C(O)NH-cycloalkyl-alkylaryl, —SO$_2$—$C_{1-10}$ alkyl, —SO$_2$-alkylaryl, —SO$_2$-heterocyclyl-alkylaryl, —SO$_2$-heterocyclyl-CF$_2$-aryl, or —SO$_2$-cycloalkyl-alkylaryl.

13. The method of claim 1, wherein the compound of Formula A has the formula:

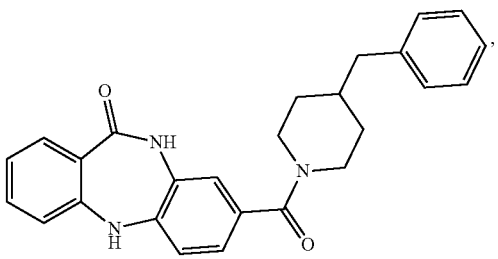

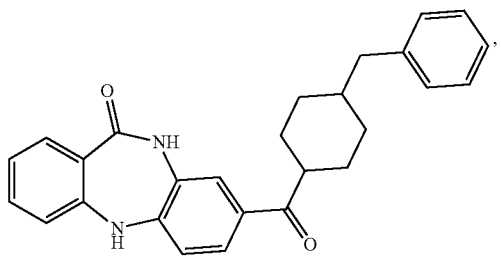

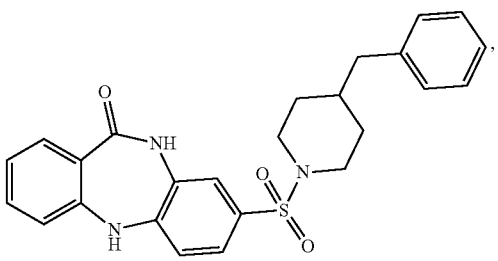

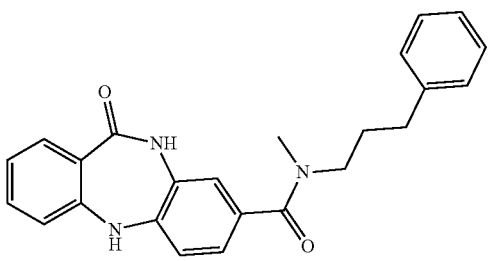

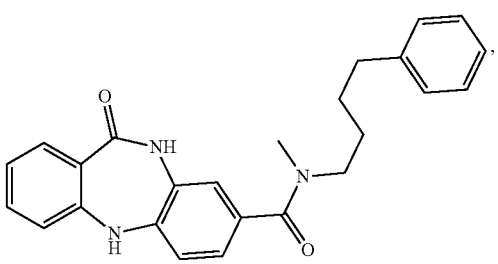

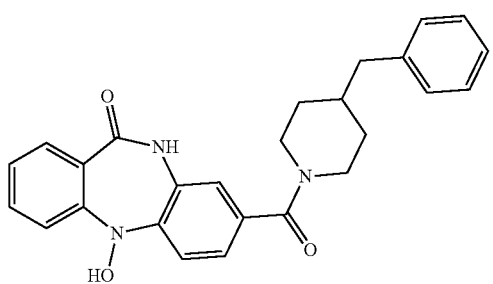

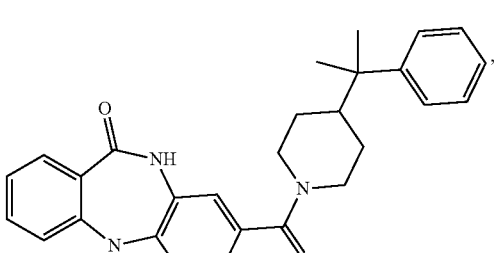

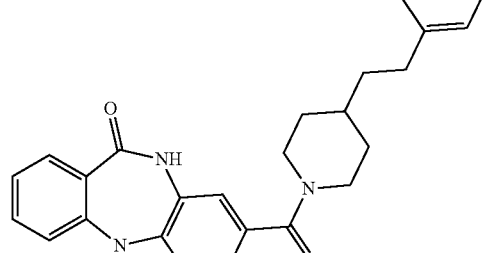

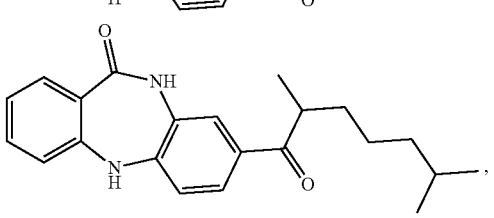

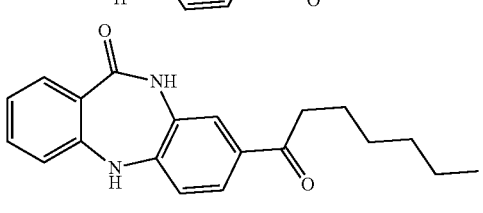

-continued
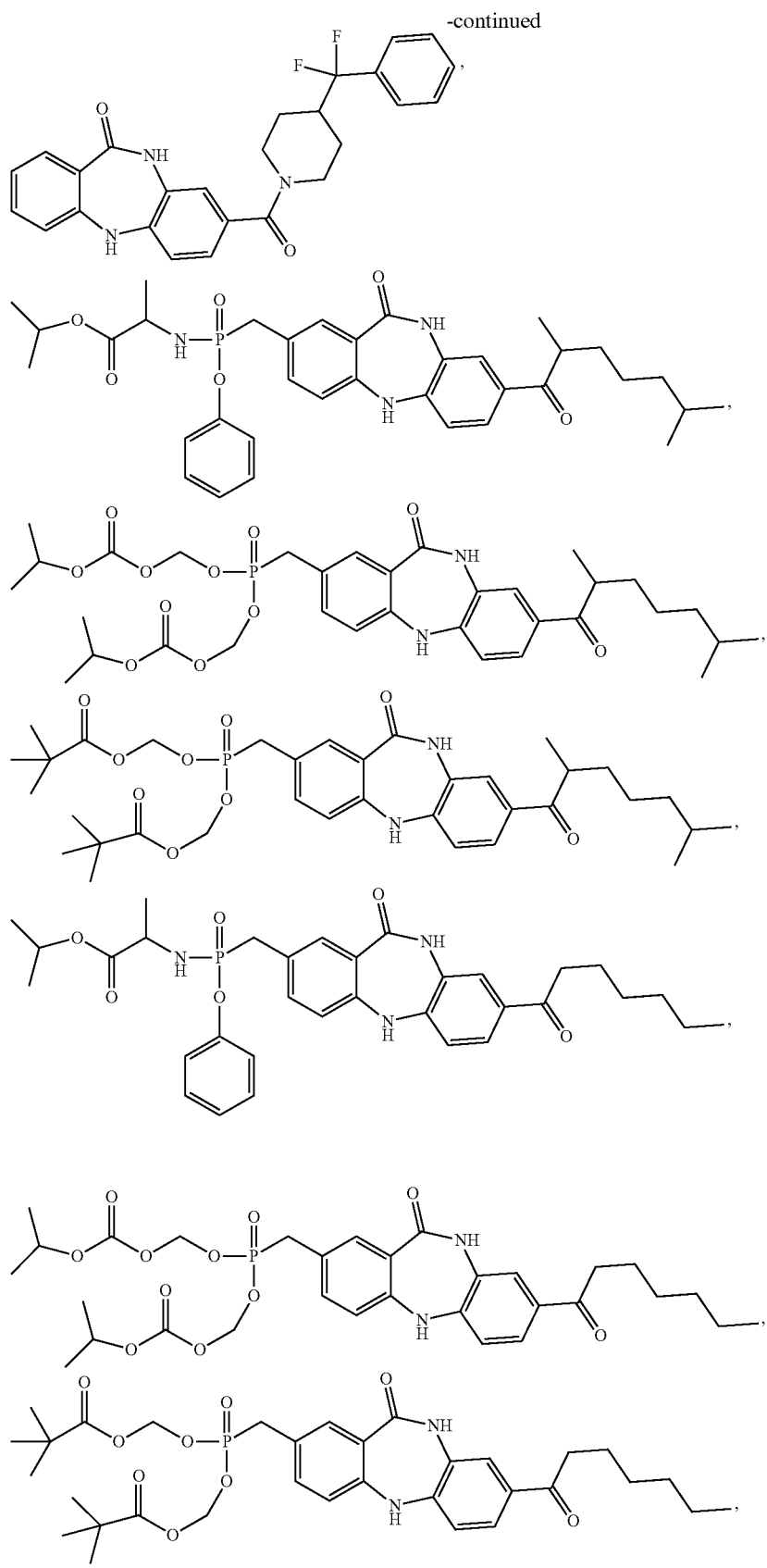
or a pharmaceutically-acceptable salt thereof.

14. The method of claim 1, wherein the compound of Formulas A has the formula:
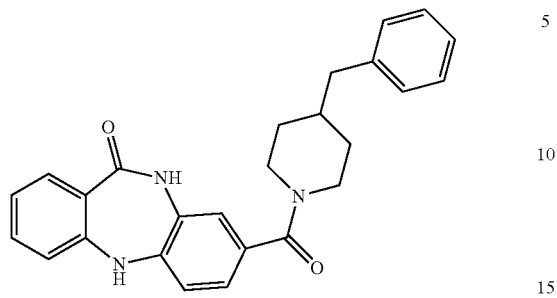
or a pharmaceutically acceptable salt thereof.
* * * * *

SEQUENCE LISTING

```
<160> NUMBER OF SEQ ID NOS: 47

<210> SEQ ID NO 1
<211> LENGTH: 28
<212> TYPE: DNA
<213> ORGANISM: Artificial Sequence
<220> FEATURE:
<223> OTHER INFORMATION: Primer used for Real-Time-PCR

<400> SEQUENCE: 1
gacacgcgta gtcaacatgg tgaaaccc                                       28

<210> SEQ ID NO 2
<211> LENGTH: 41
<212> TYPE: DNA
<213> ORGANISM: Artificial Sequence
<220> FEATURE:
<223> OTHER INFORMATION: Primer used for Real-Time-PCR

<400> SEQUENCE: 2 attgctttt attttttaac tagtccttt tttgaaatgg a                          41

<210> SEQ ID NO 3
<211> LENGTH: 23
<212> TYPE: RNA
<213> ORGANISM: Artificial Sequence
<220> FEATURE:
<223> OTHER INFORMATION: all bases are 2'-O Me-modified nucleotides
      and/or include a phosphorothioate linkage

<400> SEQUENCE: 3
acaaacacca uugucacacu cca                                            23

<210> SEQ ID NO 4
<211> LENGTH: 17
<212> TYPE: RNA
<213> ORGANISM: Artificial Sequence
<220> FEATURE:
<223> OTHER INFORMATION: all bases are 2'-O Me-modified nucleotides
      and/or include a phosphorothioate linkage

<400> SEQUENCE: 4
caccacauac cgcacgg                                                   17

<210> SEQ ID NO 5
<211> LENGTH: 22
<212> TYPE: DNA
<213> ORGANISM: Mouse

<400> SEQUENCE: 5
gtggtttcag caattatcgt gg                                             22

<210> SEQ ID NO 6
<211> LENGTH: 21
<212> TYPE: DNA
<213> ORGANISM: Mouse

<400> SEQUENCE: 6
```

```
gggtccttca gaaacagaga c                                              21

<210> SEQ ID NO 7
<211> LENGTH: 22
<212> TYPE: DNA
<213> ORGANISM: Mouse

<400> SEQUENCE: 7
gcgatgatga accaggttat ga                                             22

<210> SEQ ID NO 8
<211> LENGTH: 24
<212> TYPE: DNA
<213> ORGANISM: Mouse

<400> SEQUENCE: 8
atctcgagca agtctttcag tcct                                           24

<210> SEQ ID NO 9
<211> LENGTH: 26
<212> TYPE: DNA
<213> ORGANISM: Mouse

<400> SEQUENCE: 9
ttcgggaact atgtggagtc actttg                                         26

<210> SEQ ID NO 10
<211> LENGTH: 25
<212> TYPE: DNA
<213> ORGANISM: Mouse

<400> SEQUENCE: 10
cgcaaggctg ccctcaaacc ctcag                                          25

<210> SEQ ID NO 11
<211> LENGTH: 24
<212> TYPE: DNA
<213> ORGANISM: Mouse

<400> SEQUENCE: 11
ccatcaaacg ccattatcac acta                                           24

<210> SEQ ID NO 12
<211> LENGTH: 25
<212> TYPE: DNA
<213> ORGANISM: Mouse

<400> SEQUENCE: 12
cacacaatgg agaactctag cacaa                                          25

<210> SEQ ID NO 13
<211> LENGTH: 21
<212> TYPE: DNA
<213> ORGANISM: Mouse

<400> SEQUENCE: 13
gggtgatcct cttccacgag a                                              21

<210> SEQ ID NO 14
<211> LENGTH: 20
<212> TYPE: DNA
<213> ORGANISM: Mouse

<400> SEQUENCE: 14
```
aggggcacca caccettatc                                          20

<210> SEQ ID NO 15
<211> LENGTH: 21
<212> TYPE: DNA
<213> ORGANISM: Mouse

<400> SEQUENCE: 15
gggcgcaatg tcgagaacat g                                        21

<210> SEQ ID NO 16
<211> LENGTH: 21
<212> TYPE: DNA
<213> ORGANISM: Mouse

<400> SEQUENCE: 16
ctggcaggac ctccatcatt c                                        21

<210> SEQ ID NO 17
<211> LENGTH: 20
<212> TYPE: DNA
<213> ORGANISM: Mouse

<400> SEQUENCE: 17
agacaagaac cccaacatcc                                          20

<210> SEQ ID NO 18
<211> LENGTH: 21
<212> TYPE: DNA
<213> ORGANISM: Mouse

<400> SEQUENCE: 18
caaaggtgtc aaatgggaag g                                        21

<210> SEQ ID NO 19
<211> LENGTH: 22
<212> TYPE: DNA
<213> ORGANISM: Mouse

<400> SEQUENCE: 19
caagttttgc gatgtgagac tg                                       22

<210> SEQ ID NO 20
<211> LENGTH: 23
<212> TYPE: DNA
<213> ORGANISM: Mouse

<400> SEQUENCE: 20
ccgtctccag agtaatgttc ttg                                      23

<210> SEQ ID NO 21
<211> LENGTH: 21
<212> TYPE: DNA
<213> ORGANISM: Mouse

<400> SEQUENCE: 21
ctctgtgggt accttgatgc c                                        21

<210> SEQ ID NO 22
<211> LENGTH: 20
<212> TYPE: DNA
<213> ORGANISM: Mouse

-continued

```
<400> SEQUENCE: 22
ggaagaccct gaactctgcc                                              20

<210> SEQ ID NO 23
<211> LENGTH: 20
<212> TYPE: DNA
<213> ORGANISM: Mouse

<400> SEQUENCE: 23
caaatcctgg gtgtcaaagc                                              20

<210> SEQ ID NO 24
<211> LENGTH: 20
<212> TYPE: DNA
<213> ORGANISM: Mouse

<400> SEQUENCE: 24
catgggcttc agactggtac                                              20

<210> SEQ ID NO 25
<211> LENGTH: 22
<212> TYPE: DNA
<213> ORGANISM: Mouse

<400> SEQUENCE: 25
tccgagcaga gatcttcagg aa                                           22

<210> SEQ ID NO 26
<211> LENGTH: 22
<212> TYPE: DNA
<213> ORGANISM: Mouse

<400> SEQUENCE: 26
tgcaaccacc actcattctg ag                                           22

<210> SEQ ID NO 27
<211> LENGTH: 21
<212> TYPE: DNA
<213> ORGANISM: Mouse

<400> SEQUENCE: 27
gtgaagagga agacagcaca g                                            21

<210> SEQ ID NO 28
<211> LENGTH: 21
<212> TYPE: DNA
<213> ORGANISM: Mouse

<400> SEQUENCE: 28
gcccattcca accattactc c                                            21

<210> SEQ ID NO 29
<211> LENGTH: 22
<212> TYPE: DNA
<213> ORGANISM: Mouse

<400> SEQUENCE: 29
catggttcct aagggatgag ag                                           22

<210> SEQ ID NO 30
<211> LENGTH: 21
<212> TYPE: DNA
<213> ORGANISM: Mouse
```

<400> SEQUENCE: 30
ccccagtgtc cttacagagt g                                              21

<210> SEQ ID NO 31
<211> LENGTH: 19
<212> TYPE: DNA
<213> ORGANISM: Mouse

<400> SEQUENCE: 31
gtgcccagag tggatgtct                                                 19

<210> SEQ ID NO 32
<211> LENGTH: 20
<212> TYPE: DNA
<213> ORGANISM: Mouse

<400> SEQUENCE: 32
cataaagggt catcgtggct                                                20

<210> SEQ ID NO 33
<211> LENGTH: 19
<212> TYPE: DNA
<213> ORGANISM: Mouse

<400> SEQUENCE: 33
ttgagtccgt ctttgccag                                                 19

<210> SEQ ID NO 34
<211> LENGTH: 21
<212> TYPE: DNA
<213> ORGANISM: Mouse

<400> SEQUENCE: 34
gaagtctctg aagctgatgg g                                              21

<210> SEQ ID NO 35
<211> LENGTH: 22
<212> TYPE: DNA
<213> ORGANISM: Mouse

<400> SEQUENCE: 35
ttgccttgcg tgtttgatat tc                                             22

<210> SEQ ID NO 36
<211> LENGTH: 25
<212> TYPE: DNA
<213> ORGANISM: Mouse

<400> SEQUENCE: 36
tcacttctac tcttgctatc tttcg                                          25

<210> SEQ ID NO 37
<211> LENGTH: 20
<212> TYPE: DNA
<213> ORGANISM: Mouse

<400> SEQUENCE: 37
cccagaatcc caaccacaag                                                20

<210> SEQ ID NO 38
<211> LENGTH: 21
<212> TYPE: DNA

<213> ORGANISM: Mouse

<400> SEQUENCE: 38
ctgtagccca cgtcgtagca a					21

<210> SEQ ID NO 39
<211> LENGTH: 21
<212> TYPE: DNA
<213> ORGANISM: Mouse

<400> SEQUENCE: 39
ctggcaccac tagttggttg t					21

<210> SEQ ID NO 40
<211> LENGTH: 22
<212> TYPE: DNA
<213> ORGANISM: Unknown
<220> FEATURE:
<223> OTHER INFORMATION: Primer used for Real-Time-PCR

<400> SEQUENCE: 40
tggagtgtga caatggtgtt tg				22

<210> SEQ ID NO 41
<211> LENGTH: 22
<212> TYPE: DNA
<213> ORGANISM: Unknown
<220> FEATURE:
<223> OTHER INFORMATION: Primer used for Real-Time-PCR

<400> SEQUENCE: 41
tggcagtgtc ttagctggtt gt				22

<210> SEQ ID NO 42
<211> LENGTH: 23
<212> TYPE: DNA
<213> ORGANISM: Unknown
<220> FEATURE:
<223> OTHER INFORMATION: Primer used for Real-Time-PCR

<400> SEQUENCE: 42
taaggtgcat ctagtgcaga tag				23

<210> SEQ ID NO 43
<211> LENGTH: 22
<212> TYPE: DNA
<213> ORGANISM: Unknown
<220> FEATURE:
<223> OTHER INFORMATION: Primer used for Real-Time-PCR

<400> SEQUENCE: 43
tagcttatca gactgatgtt ga				22

<210> SEQ ID NO 44
<211> LENGTH: 21
<212> TYPE: DNA
<213> ORGANISM: Unknown
<220> FEATURE:
<223> OTHER INFORMATION: Primer used for Real-Time-PCR

<400> SEQUENCE: 44
cattattact tttggtacgc g					21

<210> SEQ ID NO 45
<211> LENGTH: 23

```
<212> TYPE: DNA
<213> ORGANISM: Unknown
<220> FEATURE:
<223> OTHER INFORMATION: Primer used for Real-Time-PCR

<400> SEQUENCE: 45
caaagtgctg ttcgtgcagg tag                                           23

<210> SEQ ID NO 46
<211> LENGTH: 22
<212> TYPE: DNA
<213> ORGANISM: Unknown
<220> FEATURE:
<223> OTHER INFORMATION: Primer used for Real-Time-PCR

<400> SEQUENCE: 46
cgcaaggatg acacgcaaat tc                                            22

<210> SEQ ID NO 47
<211> LENGTH: 22
<212> TYPE: DNA
<213> ORGANISM: Caenorhabditis elegans

<400> SEQUENCE: 47
tcaccgggtg taaatcagct tg                                            22
```